US007387887B2

(12) United States Patent
Wittwer et al.

(10) Patent No.: US 7,387,887 B2
(45) Date of Patent: Jun. 17, 2008

(54) NUCLEIC ACID MELTING ANALYSIS WITH SATURATION DYES

(75) Inventors: Carl T Wittwer, Salt Lake City, UT (US); Luming Zhou, Salt Lake City, UT (US); Virginie E. Dujols, Sandy, UT (US); Joseph A. Holden, Salt Lake City, UT (US); Carlynn Willmore-Payne, Salt Lake City, UT (US)

(73) Assignees: University of Utah Research Foundation, Salt Lake City, UT (US); Idaho Technology, Inc., Salt Lake City, UT (US)

( * ) Notice: Subject to any disclaimer, the term of this patent is extended or adjusted under 35 U.S.C. 154(b) by 327 days.

(21) Appl. No.: 10/827,890

(22) Filed: Apr. 20, 2004

(65) Prior Publication Data

US 2005/0233335 A1    Oct. 20, 2005

(51) Int. Cl.
*C12P 19/34* (2006.01)
*C12Q 1/68* (2006.01)
*C07H 21/02* (2006.01)
*C07D 293/00* (2006.01)

(52) U.S. Cl. ........................ 435/91.2; 435/6; 435/91.1; 435/975; 536/23.1; 548/100

(58) Field of Classification Search ..................... None
See application file for complete search history.

(56) References Cited

U.S. PATENT DOCUMENTS

| | | | |
|---|---|---|---|
| 4,229,526 A * | 10/1980 | Ohlschlager | ................ 430/583 |
| 4,563,417 A * | 1/1986 | Albarella et al. | .............. 435/6 |
| 5,066,584 A * | 11/1991 | Gyllensten et al. | ......... 435/91.2 |
| 5,436,134 A | 7/1995 | Haugland et al. | |
| 5,563,037 A | 10/1996 | Sutherland et al. | |
| 5,639,609 A * | 6/1997 | Kruse-Mueller et al. | ........ 435/6 |
| 5,658,751 A | 8/1997 | Yue et al. | |
| 5,853,989 A * | 12/1998 | Jeffreys et al. | ................ 435/6 |
| 5,871,908 A | 2/1999 | Henco et al. | |
| 6,174,670 B1 * | 1/2001 | Wittwer et al. | ................ 435/6 |
| 6,437,141 B2 | 8/2002 | Randall et al. | |
| 6,506,568 B2 | 1/2003 | Shriver et al. | |
| 2003/0157507 A1 | 8/2003 | Lipsky et al. | |

FOREIGN PATENT DOCUMENTS

| | | |
|---|---|---|
| EP | 1298490 A2 * | 4/2003 |
| WO | WO 00/66664 | 11/2000 |
| WO | WO 02/26891 | 4/2002 |

OTHER PUBLICATIONS

New England Biolabs 1998/99 Catalog (NEB Catalog).*
Higuchi et al. ("Simultaneous amplification and detection of specific DNA sequences" Biotechnology (N Y). Apr. 1992;10(4):413-7).*
Zipper et al. "Investigations on DNA intercalation and surface binding by SYBR Green I, its structure determination and methodological implications" Nucleic Acids Res. Jul. 12, 2004;32(12);e103.*
Stratagene ("Gene Characterization Kits" 1988).*
Kanony et al. ("Photobleaching of asymmetric cyanines used for fluorescence imaging of single DNA molecules" J Am Chem Soc. Aug. 22, 2001;123(33):7985-95).*
Statagene ("Gene Characterization Kits" 1988).*
Lebaron et al. ("Comparison of blue nucleic acid dyes for flow cytometric enumeration of bacteria in aquatic systems" Appl Environ Microbiol. May 1998;64(5):1725-30).*
Abrams ES, et al., Genomics 1990; 7: 463-75.
Aktipis S, et al., Biochemistry 1975; 14: 326-31.
Aoshima T. Et al., Clin Chem 2000; 46: 119-22.
Crockett, A.O. and C.T. Wittwer, Anal. Biochem. 2001; 290: 89-97.
Deichmeister MV, et al, "Structur of quaternary salts of 4-methylpyrimidine," Khim. Geteroltiskl. Soedin., Sb. 1: Azotsoderzhashchie Geterotsikly (1967). SciFinder Abstract.
Douthart RJ, et al., Biochemistry, 1973; 12: 214-20.
Germer S, et al., Genome Research 2000; 10: 258-266.
Germer S, et al., Genome Research 1999; 9: 72-79.
Gundry CN, et al., Genetick TEsting, 1999; 3: 365-70.
Hermann M, et al., Clin Chem 2000; 46: 425-28.
Hlghsmith WE, et al., Electrophoresis 1999; 20: 1186-94.
Higuchi, R, et al., Biotechnology 1992; 10: 413-17.
Hladnik U, et al., Clin Exp Med. 2002; 2: 105-08.
Ishiguro, T., et al. Anal. Biochem 1995; 229: 207-213.
Lay MJ, et al., Clin. Chem 1997; 43: 2262-67.
Lipsky RH, et al., Clin Chem 2001; 47: 635-44.
Liu, W, et al. Anal. Biochem 2002; 302: 52-59.
Marziliano N, et al., Clin Chem 2000; 46: 423-25.
Nataraj AJ, et al., Electrophoresis 1999; 20: 1177-85.
Orita O, et al., Proc Natl Acad Sci USA 1989; 86: 2766-70.
Pirulli D, et al., Clin Chem 2000; 46: 1842-44.
Press WH, et al., eds. Numerical recipes in C, 2nd ed. New York: Cambridge University Press, 1992: 650-55.
Ririe KM, et al. Anal. Biochem 1997; 245: 154-60.
SantaLucia J., Jr., Biochemistry 1996; 35: 3555-62.
Tanriverdi S, et al., J Clin Microbiol. 2002; 40: 3237-44.
Taylor GR, et al., Genet Anal 1999; 14: 181-86.
Tseng, BY, et al., Anal. Biochem 1997; 245: 207-12.
Venter JC, et al., Science 2001; 291: 1304-51.
Von Ahsen N, et al., Clin Chem 2001; 47: 1331-32.
Von Ahsen N, et al. Clin Chem 2001; 47: 1956-61.
Wartell RM, et al., J Chromatogr A 1998; 806: 169-85.
Wetmur JG, Crit Rev Giochem Mol Biol 1991; 26: 227-59.
Wittwer CT, et al., BioTechniques 1997; 22: 130-38.
Wittwer CT, et al., BioTechniques 1997; 22: 176-81.
Xiao W, et al., Hum Mutat 2001; 17: 439-74.

* cited by examiner

*Primary Examiner*—Kenneth R. Horlick
*Assistant Examiner*—Christopher M. Babic
(74) *Attorney, Agent, or Firm*—Homer W. Faucett, III; Doreen J. Gridley; Ice Miller LLP

(57) ABSTRACT

Methods are provided for nucleic acid analysis wherein a target nucleic acid is mixed with a dsDNA binding dye to form a mixture. Optionally, an unlabeled probe is included in the mixture. A melting curve is generated for the target nucleic acid by measuring fluorescence from the dsDNA binding dye as the mixture is heated. Dyes for use in nucleic acid analysis and methods for making dyes are also provided.

9 Claims, 45 Drawing Sheets

SEQUENCE LISTING

<160> NUMBER OF SEQ ID NOS: 51

<210> SEQ ID NO 1
<211> LENGTH: 20
<212> TYPE: DNA
<213> ORGANISM: Homo sapiens

<400> SEQUENCE: 1

```
ggcaccatta aagaaaatat                                              20

<210> SEQ ID NO 2
<211> LENGTH: 18
<212> TYPE: DNA
<213> ORGANISM: Homo sapiens

<400> SEQUENCE: 2
tcatcatagg aaacacca                                                18

<210> SEQ ID NO 3
<211> LENGTH: 20
<212> TYPE: DNA
<213> ORGANISM: Homo sapiens

<400> SEQUENCE: 3
acacaactgt gttcactagc                                              20

<210> SEQ ID NO 4
<211> LENGTH: 20
<212> TYPE: DNA
<213> ORGANISM: Homo sapiens

<400> SEQUENCE: 4
caacttcatc cacgttcacc                                              20

<210> SEQ ID NO 5
<211> LENGTH: 14
<212> TYPE: DNA
<213> ORGANISM: Homo sapiens

<400> SEQUENCE: 5
ccagctccgg gaga                                                    14

<210> SEQ ID NO 6
<211> LENGTH: 21
<212> TYPE: DNA
<213> ORGANISM: Homo sapiens

<400> SEQUENCE: 6
catacaggat ggttaacatg g                                            21

<210> SEQ ID NO 7
<211> LENGTH: 21
<212> TYPE: DNA
<213> ORGANISM: Homo sapiens

<400> SEQUENCE: 7
agaatataca cttctgctta g                                            21

<210> SEQ ID NO 8
<211> LENGTH: 17
<212> TYPE: DNA
<213> ORGANISM: Homo sapiens

<400> SEQUENCE: 8
tatcactata tgcatgc                                                 17

<210> SEQ ID NO 9
<211> LENGTH: 28
<212> TYPE: DNA
<213> ORGANISM: Homo sapiens

<400> SEQUENCE: 9
```

```
gaaaccggcc tctgctgggg agaagcaa                                              28

<210> SEQ ID NO 10
<211> LENGTH: 28
<212> TYPE: DNA
<213> ORGANISM: Homo sapiens

<400> SEQUENCE: 10
gaaaccggcc tctgctgggg agaagcaa                                              28

<210> SEQ ID NO 11
<211> LENGTH: 28
<212> TYPE: DNA
<213> ORGANISM: Homo sapiens

<400> SEQUENCE: 11
gaaaccggcc tctgctgggg agaagcaa                                              28

<210> SEQ ID NO 12
<211> LENGTH: 28
<212> TYPE: DNA
<213> ORGANISM: Homo sapiens

<400> SEQUENCE: 12
gaaaccggcc tctgctgggg agaagcaa                                              28

<210> SEQ ID NO 13
<211> LENGTH: 24
<212> TYPE: DNA
<213> ORGANISM: Homo sapiens

<400> SEQUENCE: 13
tgttggtccc aattgtctcc cctc                                                  24

<210> SEQ ID NO 14
<211> LENGTH: 23
<212> TYPE: DNA
<213> ORGANISM: Homo sapiens

<400> SEQUENCE: 14
agccgcgccg tggaagaggg tcg                                                   23

<210> SEQ ID NO 15
<211> LENGTH: 23
<212> TYPE: DNA
<213> ORGANISM: Homo sapiens

<400> SEQUENCE: 15
agccgcgccg tggaagaggg tcg                                                   23

<210> SEQ ID NO 16
<211> LENGTH: 18
<212> TYPE: DNA
<213> ORGANISM: Homo sapiens

<400> SEQUENCE: 16
ggccggggtc actcaccg                                                         18

<210> SEQ ID NO 17
<211> LENGTH: 18
<212> TYPE: DNA
<213> ORGANISM: Homo sapiens
```

```
<400> SEQUENCE: 17
cccgaggttg gtcggggc                                                   18

<210> SEQ ID NO 18
<211> LENGTH: 18
<212> TYPE: DNA
<213> ORGANISM: Homo sapiens

<400> SEQUENCE: 18
cccgaggttg gtcggggc                                                   18

<210> SEQ ID NO 19
<211> LENGTH: 20
<212> TYPE: DNA
<213> ORGANISM: Homo sapiens

<400> SEQUENCE: 19
atcaggtgag gcgccccgtg                                                 20

<210> SEQ ID NO 20
<211> LENGTH: 20
<212> TYPE: DNA
<213> ORGANISM: Homo sapiens

<400> SEQUENCE: 20
atcaggtgag gcgccccgtg                                                 20

<210> SEQ ID NO 21
<211> LENGTH: 17
<212> TYPE: DNA
<213> ORGANISM: Homo sapiens

<400> SEQUENCE: 21
accaggctct acagtaa                                                    17

<210> SEQ ID NO 22
<211> LENGTH: 17
<212> TYPE: DNA
<213> ORGANISM: Homo sapiens

<400> SEQUENCE: 22
gttaaatgca tcagaag                                                    17

<210> SEQ ID NO 23
<211> LENGTH: 20
<212> TYPE: DNA
<213> ORGANISM: Artificial
<220> FEATURE:
<223> OTHER INFORMATION: Primer for PCR amplification of engineered
      plasmid.

<400> SEQUENCE: 23
gatatttgaa gtctttcggg                                                 20

<210> SEQ ID NO 24
<211> LENGTH: 20
<212> TYPE: DNA
<213> ORGANISM: Artificial
<220> FEATURE:
<223> OTHER INFORMATION: Primer for PCR amplification of engineered
      plasmid.

<400> SEQUENCE: 24
taagagcaac actatcataa                                                 20
```

<210> SEQ ID NO 25
<211> LENGTH: 14
<212> TYPE: DNA
<213> ORGANISM: Artificial
<220> FEATURE:
<223> OTHER INFORMATION: Probe for detecting SNP of engineered plasmid.
<220> FEATURE:
<221> NAME/KEY: variation
<222> LOCATION: (7)..(7)
<223> OTHER INFORMATION: SNP location.

<400> SEQUENCE: 25
caatgaatat ttat                                                        14

<210> SEQ ID NO 26
<211> LENGTH: 16
<212> TYPE: DNA
<213> ORGANISM: Artificial
<220> FEATURE:
<223> OTHER INFORMATION: Probe for detecting SNP of engineered plasmid.
<220> FEATURE:
<221> NAME/KEY: variation
<222> LOCATION: (8)..(8)
<223> OTHER INFORMATION: SNP location

<400> SEQUENCE: 26
tcaatgaata tttatg                                                      16

<210> SEQ ID NO 27
<211> LENGTH: 18
<212> TYPE: DNA
<213> ORGANISM: Artificial
<220> FEATURE:
<223> OTHER INFORMATION: Probe for detecting SNP of engineered plasmid.
<220> FEATURE:
<221> NAME/KEY: variation
<222> LOCATION: (9)..(9)
<223> OTHER INFORMATION: SNP location.

<400> SEQUENCE: 27
ttcaatgaat atttatga                                                    18

<210> SEQ ID NO 28
<211> LENGTH: 20
<212> TYPE: DNA
<213> ORGANISM: Artificial
<220> FEATURE:
<223> OTHER INFORMATION: Probe for detecting SNP of engineered plasmid.
<220> FEATURE:
<221> NAME/KEY: variation
<222> LOCATION: (10)..(10)
<223> OTHER INFORMATION: SNP Location.

<400> SEQUENCE: 28
attcaatgaa tatttatgac                                                  20

<210> SEQ ID NO 29
<211> LENGTH: 22
<212> TYPE: DNA
<213> ORGANISM: Artificial
<220> FEATURE:
<223> OTHER INFORMATION: Probe for detecting SNP of engineered plasmid.
<220> FEATURE:
<221> NAME/KEY: variation
<222> LOCATION: (11)..(11)
<223> OTHER INFORMATION: SNP Location.

<400> SEQUENCE: 29

```
<210> SEQ ID NO 30
<211> LENGTH: 24
<212> TYPE: DNA
<213> ORGANISM: Artificial
<220> FEATURE:
<223> OTHER INFORMATION: Probe for detecting SNP of engineered plasmid.
<220> FEATURE:
<221> NAME/KEY: variation
<222> LOCATION: (12)..(12)
<223> OTHER INFORMATION: SNP location.

<400> SEQUENCE: 30
ggattcaatg aatatttatg acga                                          24

<210> SEQ ID NO 31
<211> LENGTH: 26
<212> TYPE: DNA
<213> ORGANISM: Artificial
<220> FEATURE:
<223> OTHER INFORMATION: Probe for detecting SNP of engineered plasmid.
<220> FEATURE:
<221> NAME/KEY: variation
<222> LOCATION: (13)..(13)
<223> OTHER INFORMATION: SNP location.

<400> SEQUENCE: 31
gggattcaat gaatatttat gacgat                                        26

<210> SEQ ID NO 32
<211> LENGTH: 28
<212> TYPE: DNA
<213> ORGANISM: Artificial
<220> FEATURE:
<223> OTHER INFORMATION: Probe for detecting SNP of engineered plasmid.
<220> FEATURE:
<221> NAME/KEY: variation
<222> LOCATION: (14)..(14)
<223> OTHER INFORMATION: SNP location.

<400> SEQUENCE: 32
ggggattcaa tgaatattta tgacgatt                                      28

<210> SEQ ID NO 33
<211> LENGTH: 30
<212> TYPE: DNA
<213> ORGANISM: Artificial
<220> FEATURE:
<223> OTHER INFORMATION: Probe for detecting SNP of engineered plasmid.
<220> FEATURE:
<221> NAME/KEY: variation
<222> LOCATION: (15)..(15)
<223> OTHER INFORMATION: SNP location.

<400> SEQUENCE: 33
gggggattca atgaatattt atgacgattc                                    30

<210> SEQ ID NO 34
<211> LENGTH: 20
<212> TYPE: DNA
<213> ORGANISM: Homo sapiens

<400> SEQUENCE: 34
acatagtttc ttacctcttc                                               20

<210> SEQ ID NO 35
<211> LENGTH: 21
```

(first line continued from previous page:)

gattcaatga atatttatga cg                                            22

```
<212> TYPE: DNA
<213> ORGANISM: Homo sapiens

<400> SEQUENCE: 35
acttctaatg atgattatgg g                                              21

<210> SEQ ID NO 36
<211> LENGTH: 22
<212> TYPE: DNA
<213> ORGANISM: Homo sapiens

<400> SEQUENCE: 36
tgtgcctttc aaattcagat tg                                             22

<210> SEQ ID NO 37
<211> LENGTH: 20
<212> TYPE: DNA
<213> ORGANISM: Homo sapiens

<400> SEQUENCE: 37
cagcaaatgc ttgctagacc                                                20

<210> SEQ ID NO 38
<211> LENGTH: 30
<212> TYPE: DNA
<213> ORGANISM: Homo sapiens

<400> SEQUENCE: 38
taaagaaaat atcatctttg gtgtttccta                                     30

<210> SEQ ID NO 39
<211> LENGTH: 28
<212> TYPE: DNA
<213> ORGANISM: Homo sapiens
<220> FEATURE:
<221> NAME/KEY: misc_feature
<222> LOCATION: (14)..(14)
<223> OTHER INFORMATION: n is g or t

<400> SEQUENCE: 39
caatatagtt cttngagaag gtggaatc                                       28

<210> SEQ ID NO 40
<211> LENGTH: 20
<212> TYPE: DNA
<213> ORGANISM: Homo sapiens

<400> SEQUENCE: 40
gatgctctgc ttctgtactg                                                20

<210> SEQ ID NO 41
<211> LENGTH: 23
<212> TYPE: DNA
<213> ORGANISM: Homo sapiens

<400> SEQUENCE: 41
gcctaaacat ccccttaaat tgg                                            23

<210> SEQ ID NO 42
<211> LENGTH: 22
<212> TYPE: DNA
<213> ORGANISM: Homo sapiens

<400> SEQUENCE: 42
```
ctctccagag tgctctaatg ac                                       22

<210> SEQ ID NO 43
<211> LENGTH: 21
<212> TYPE: DNA
<213> ORGANISM: Homo sapiens

<400> SEQUENCE: 43
gcccctgttt cataactgac c                                        21

<210> SEQ ID NO 44
<211> LENGTH: 21
<212> TYPE: DNA
<213> ORGANISM: Homo sapiens

<400> SEQUENCE: 44
cggccatgac tgtcgctgta a                                        21

<210> SEQ ID NO 45
<211> LENGTH: 21
<212> TYPE: DNA
<213> ORGANISM: Homo sapiens

<400> SEQUENCE: 45
ctccaatggt gcaggctcca a                                        21

<210> SEQ ID NO 46
<211> LENGTH: 20
<212> TYPE: DNA
<213> ORGANISM: Homo sapiens

<400> SEQUENCE: 46
tctcctccaa cctaatagtg                                          20

<210> SEQ ID NO 47
<211> LENGTH: 19
<212> TYPE: DNA
<213> ORGANISM: Homo sapiens

<400> SEQUENCE: 47
ggactgtcaa gcagagaat                                           19

<210> SEQ ID NO 48
<211> LENGTH: 22
<212> TYPE: DNA
<213> ORGANISM: Homo sapiens

<400> SEQUENCE: 48
atctttggtg tttcctatga tg                                       22

<210> SEQ ID NO 49
<211> LENGTH: 26
<212> TYPE: DNA
<213> ORGANISM: Homo sapiens

<400> SEQUENCE: 49
ctcagttttc ctggattatg cctggc                                   26

<210> SEQ ID NO 50
<211> LENGTH: 18
<212> TYPE: DNA
<213> ORGANISM: Artificial
<220> FEATURE:
<223> OTHER INFORMATION: Primer for amplifying region on engineered

```
                          -continued
      plasmid.

<400> SEQUENCE: 50
tctgctctgc ggctttct                                              18

<210> SEQ ID NO 51
<211> LENGTH: 23
<212> TYPE: DNA
<213> ORGANISM: artificial
<220> FEATURE:
<223> OTHER INFORMATION: Primer for amplifying region on engineered
      plasmid.

<400> SEQUENCE: 51
cgaagcagta aagctcttg gat                                         23
```

NUCLEIC ACID MELTING ANALYSIS WITH SATURATION DYES

FIELD OF THE INVENTION

The present invention relates to double stranded nucleic acid binding dyes and methods of performing nucleic acid analysis in the presence of a double-stranded nucleic acid binding dye.

BACKGROUND OF THE INVENTION

Methods for analyzing DNA sequence variation can be divided into two general categories: 1) genotyping for known sequence variants and 2) scanning for unknown variants. There are many methods for genotyping known sequence variants, and single step, homogeneous, closed tube methods that use fluorescent probes are available (Lay M J, et al., Clin. Chem 1997;43:2262-7). In contrast, most scanning techniques for unknown variants require gel electrophoresis or column separation after PCR. These include single-strand conformation polymorphism (Orita O, et al., Proc Natl Acad Sci USA 1989; 86:2766-70), heteroduplex migration (Nataraj A J, et al., Electrophoresis 1999;20:1177-85), denaturing gradient gel electrophoresis (Abrams E S, et al., Genomics 1990;7:463-75), temperature gradient gel electrophoresis (Wartell R M, et al., J Chromatogr A 1998; 806:169-85), enzyme or chemical cleavage methods (Taylor G R, et al., Genet Anal 1999;14:181-6), as well as DNA sequencing. Identifying new mutations by sequencing also requires multiple steps after PCR, namely cycle sequencing and gel electrophoresis. Denaturing high-performance liquid chromatography (Xiao W, et al., Hum Mutat 2001;17:439-74) involves injecting the PCR product into a column.

Recently, homogeneous fluorescent methods have been reported for mutation scanning. SYBR® Green I (Molecular Probes, Eugene, Oreg.) is a-double strand-specific DNA dye often used to monitor product formation (Wittwer C T, et al., BioTechniques 1997;22:130-8) and melting temperature (Ririe K M, et al., Anal. Biochem 1997;245:154-60) in real-time PCR. The presence of heterozygous single base changes have been detected in products up to 167 bp by melting curve analysis with SYBR® Green I (Lipsky R H, et al., Clin Chem 2001;47:635-44). However, subsequent to amplification and prior to melting analysis, the PCR product was purified and high concentrations of SYBR® Green I were added. The concentration of SYBR® Green I used for detection in this method inhibits PCR (Wittwer C T, et al., BioTechniques 1997;22:130-1, 134-8); thus, the dye was added after amplification. A dye that could be used to detect the presence of genetic variation including heterozygous single base changes and could be added prior to PCR would be desirable.

Single nucleotide polymorphisms (SNPs) are by far the most common genetic variations observed in man and other species. In these polymorphisms, only a single base varies between individuals. The alteration may cause an amino acid change in a protein, alter rates of transcription, affect mRNA spicing, or have no apparent effect on cellular processes. Sometimes when the change is silent (e.g., when the amino acid it codes for does not change), SNP genotyping may still be valuable if the alteration is linked to (associated with) a unique phenotype caused by another genetic alteration.

There are many methods for genotyping SNPs. Most use PCR or other amplification techniques to amplify the template of interest. Contemporaneous or subsequent analytical techniques may be employed, including gel electrophoresis, mass spectrometry, and fluorescence. Fluorescence techniques that are homogeneous and do not require the addition of reagents after commencement of amplification or physical sampling of the reactions for analysis are attractive. Exemplary homogeneous techniques use oligonucleotide primers to locate the region of interest and fluorescent labels or dyes for signal generation. Illustrative PCR-based methods are completely closed-tubed, using a thermostable enzyme that is stable to DNA denaturation temperature, so that after heating begins, no additions are necessary.

Several closed-tube, homogeneous, fluorescent PCR methods are available to genotype SNPs. These include systems that use FRET oligonucleotide probes with two interacting chromophores (adjacent hybridization probes, TaqMan probes, Molecular Beacons, Scorpions), single oligonucleotide probes with only one fluorophore (G-quenching probes, Crockett, A. O. and C. T. Wittwer, Anal. Biochem. 2001;290:89-97 and SimpleProbes, Idaho Technology), and techniques that use a dsDNA dye instead of covalent, fluorescently-labeled oligonucleotide probes. The dye techniques are attractive because labeled oligonucleotide probes are not required, allowing for reduced design time and cost of the assays.

Two techniques for SNP typing using dsDNA dyes have been published. Allele-specific amplification in the presence of dsDNA dyes can be used to genotype with real-time PCR (Germer S, et al., Genome Research 2000;10:258-266). In the method of the Germer reference, two allele-specific primers differ at their 3'-base and differentially amplify one or the other allele in the presence of a common reverse primer. While no fluorescently-labeled oligonucleotides are needed, genotyping requires three primers and two wells for each SNP genotype. In addition, a real-time PCR instrument that monitors fluorescence each cycle is necessary.

The other dye-based method does not require real-time monitoring, needs only one well per SNP genotype, and uses melting analysis (Germer, S, et. al., Genome Research 1999;9:72-79). In this method, allele-specific amplification is also used, requiring three primers, as with the previous Germer method. In addition, one of the primers includes a GC-clamp tail to raise the melting temperature of one amplicon, allowing differentiation by melting temperature in one well. Fluorescence is monitored after PCR amplification, and real-time acquisition is not required.

SUMMARY OF THE INVENTION

In one aspect of the present invention, a method is provided that requires only a standard PCR mixture, including reagents, primers, and the simple addition prior to PCR of a "saturating" double-stranded (ds) DNA binding dye or a novel dsDNA binding dye according to this disclosure. For purposes of this disclosure, a "saturating" dye is a dye that does not significantly inhibit PCR when present at concentrations that provide maximum fluorescence signal for an amount of dsDNA typically generated by PCR in the absence of dye, illustratively about 10 ng/μL. Although the dyes are identified by their compatibility with PCR at near saturating concentrations, it is understood that the dyes can be used at much lower concentrations. During or subsequent to amplification, the dyes may be used to distinguish heteroduplexes and homoduplexes by melting curve analysis in a similar fashion to when labeled primers are used. The identification of heteroduplexes and homoduplexes may be used for a variety of analyses, including mutation scanning and genotyping. The term "scanning" refers to the process in which a nucleic acid fragment is compared to a reference nucleic acid fragment to detect the presence of any difference in sequence. A positive answer indicating the presence of a sequence difference may not necessarily reflect the exact nature of the sequence variance or its position on the nucleic acid fragment. The term "genotyping" includes the detection and determination of known nucleic acid sequence variances, including but not limited to, SNPs, base deletions, base insertions, sequence duplications, rearrangements, inversions, base methylations, the number of short tandem repeats; and in the case of a diploid genome, whether the genome is a homozygote or a heterozygote of the sequence variance, as well as the cis/trans positional relationship of two or more sequence variances on a DNA strand (haplotyping). Optionally, one or more unlabeled probes may be added to the mixture at any time prior to melting curve analysis.

The term "unlabeled probe" refers to an oligonucleotide or polynucleotide that is not covalently linked to a dye and that is configured to hybridize perfectly or partially to a target sequence. The dye that is present in the mixture is free to bind to or disassociate from the unlabeled probe, particularly as the probe hybridizes to and melts from the target sequence. The terms "oligonucleotide" and "polynucleotide" as used herein include oligomers and polymers of natural or modified monomers or linkages including deoxyribonucleosides, ribonucleosides, protein nucleic acid nucleosides, and the like that are capable of specifically binding to a target polynucleotide by base-pairing interactions. Optionally, the unlabeled probe may be modified with one or more non-fluorescent moieties, such as but not limited to non-fluorescent minor-groove binders, biotin, spacers, linkers, phosphates, base analogs, non-natural bases, and the like.

In another aspect of this invention, various dsDNA binding dyes are identified. The dsDNA binding dyes of the present invention are capable of existing at sufficiently saturating conditions with respect to the DNA during or after amplification, while minimizing the inhibition of PCR. For example, at maximum PCR-compatible concentrations, the dsDNA binding dye has a percent saturation of at least 50%. In other embodiments, the percent saturation is at least 80%, and more particularly, at least 90%. In yet other embodiments, the percent saturation is at least 99%. It is understood that the percent saturation is the percent fluorescence compared to fluorescence of the same dye at saturating concentrations, i.e. the concentration that provides the highest fluorescence intensity possible in the presence of a predetermined amount of dsDNA. Illustratively, the predetermined amount of dsDNA is 100 ng/10 µL which is the amount of DNA produced at the end of a typical PCR at plateau. It is further understood that dye preparations may contain impurities that inhibit amplification. Such impurities should be removed prior to a determination of the percent saturation. It is also understood that the measurement of fluorescence intensity for percent saturation is performed at the wavelength that is well matched for the detection of dye bound to dsDNA, and if possible, not at wavelengths that will detect high background fluorescence from free dye or secondary forms of dye binding which may occur at a high dye-to-bp ratio (e.g. binding of dye to the dsDNA-dye complex or to single-stranded nucleic acids).

In yet another aspect of the present invention, the dsDNA binding dye has greater than 50% saturation at maximum PCR-compatible concentrations, and has excitation/emission spectra that would not suggest compatibility with standard real-time PCR instruments. "Standard" instruments for real-time PCR analysis have an excitation range of about 450-490 nm and an emission detection range of about 510-530 nm. It has been found that certain "blue" dyes are compatible with these systems, although their excitation/emission spectra would suggest otherwise. Thus, in this aspect of the invention a method is provided for analysis during or subsequent to PCR using a standard real-time PCR instrument and a dsDNA binding dye having an excitation maximum in the range of 410-465 nm, more particularly in the range of 430-460 nm, and having an emission maximum in the range of 450-500 nm, more particularly in the range of 455-485 nm, as measured in PCR buffer in the presence of dsDNA. Suitable instrumentation may use the excitation/detection ranges above, or may be modified according to the excitation/emission maxima of the dyes. Suitable ranges for detection of the "blue" dyes of this invention as well as for detection of traditional dyes such as fluorescein and SYBR® Green I may include 440-470 nm for excitation and 500-560 for detection. It is noted that while many of these dyes are suitable for use with standard real-time PCR instruments and melting instrumentation, adjustment of the optics to better match the excitation/emission spectra of these dyes may further improve their sensitivity for use in quantitative or qualitative amplification analysis.

In yet another aspect of this invention, scanning or genotyping is performed by melting curve analysis in the presence of one or more unlabeled probes and a double-stranded binding dye. The melting curve analysis may take place during or subsequent to amplification, or in the absence of amplification. The dye may be a saturating dye or a novel dye according to this disclosure.

While the examples provided herein are directed to melting curve analysis, it is understood that the dyes of the present invention can be used for a variety of real-time quantitative PCR analyses, including quantification of the nucleic acid, determination of initial concentration, testing for the presence of a nucleic acid, multiplexing with labeled probes, and other PCR-based methods.

Furthermore, while reference is made to PCR, other methods of amplification may be compatible with the dyes of this invention. Such suitable procedures include strand displacement amplification (SDA); nucleic acid sequence-based amplification (NASBA); cascade rolling circle amplification (CRCA), Q beta replicase mediated amplification; isothermal and chimeric primer-initiated amplification of nucleic acids (ICAN); transcription-mediated amplification (TMA), and the like. Asymmetric PCR may also be used. Therefore, when the term PCR is used, it should be understood to include variations on PCR and other alternative amplification methods. Amplification methods that favor amplification of one strand over the other are particularly well suited for melting curve analysis using unlabeled probes.

Moreover, while reference is made to amplification, it is understood that the melting curve analysis of the present invention may be performed on nucleic acid samples that have been obtained without amplification.

Additionally, it is understood that the dsDNA binding dyes include intercalators, as well as other dyes that bind to nucleic acids, as long as the dye differentially binds to double-stranded and single-stranded nucleic acids, or otherwise produces a differential signal based on the quantity of double-stranded nucleic acid.

Thus, in one embodiment of this invention, novel dyes are presented. The novel dyes, which may or may not be saturating dyes, may be used during or subsequent to amplification, or may be used during melting curve analysis in the presence or absence of amplification. Illustratively, the novel dyes have the formula:

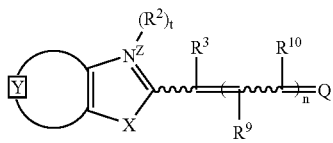

wherein
the moiety

Y represents an optionally-substituted fused monocyclic or polycyclic aromatic ring or an optionally-substituted fused monocyclic or polycyclic nitrogen-containing heteroaromatic ring;

X is oxygen, sulfur, selenium, tellurium or a moiety selected from $C(CH_3)_2$ and $NR^1$, where $R^1$ is hydrogen or $C_{1-6}$ alkyl;

$R^2$ is selected from the group consisting of $C_{1-6}$ alkyl, $C_{3-8}$ cycloalkyl, aryl, aryl($C_{1-2}$ alkyl), hydroxyalkyl, alkoxyalkyl, aminoalkyl, mono and dialkylaminoalkyl, trialkylammoniumalkyl, alkylenecarboxylate, alkylenecarboxamide, alkylenesulfonate, optionally substituted cyclic heteroatom-containing moieties, and optionally substituted acyclic heteroatom-containing moieties;

t=0 or 1;

Z is a charge selected from 0 or 1;

$R^3$, $R^9$, and $R^{10}$ are each independently selected from the group consisting of hydrogen, $C_{1-6}$ alkyl, and arylcarbonyl;

n=0,1,or2; and

Q is an heterocycle selected from the group of structures consisting of:

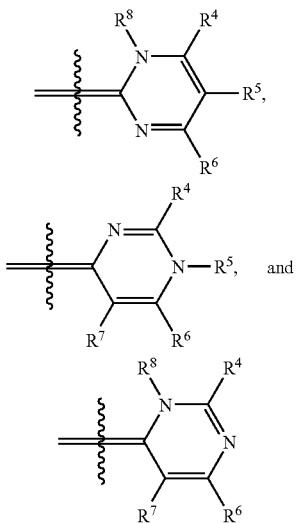

wherein $R^4$, $R^5$, $R^6$, $R^7$, and $R^8$ are independently selected from the group consisting of hydrogen, halogen, alkyl, cycloalkyl, heteroalkyl, heterocycloalkyl, alkenyl, polyalkenyl, alkynyl, polyalkynyl, alkenylalkynyl, aryl, heteroaryl, alkoxy, alkylthio, arylcarbonylthio, cycloheteroalkylcarbonylthio, dialkylaminoalkylcarbonylthio, dialkylamino, cycloalkylthio, cycloheteroalkylthio, trialkylammoniumalkylthio, and nucleosidylthio, each of which may be optionally substituted; an acyclic heteroatom-containing moiety, a cyclic heteroatom-containing moiety, a BRIDGE-DYE, and a reactive group, each of which optionally includes a quaternary ammonium moiety.

Illustratively, in one embodiment at least one of $R^4$, $R^5$, $R^6$, $R^7$, and $R^8$ is selected from the group consisting of arylcarbonylthio, cycloheteroalkylcarbonylthio, dialkylaminoalkylcarbonylthio, cycloalkylthio, cycloheteroalkylthio, trialkylammoniumalkylthio, and nucleosidylthio, each of which may be optionally substituted. In another embodiment, the dye is selected from the group consisting of N7, O7, P7, Q7, R7, S7, T7, U7, V7, W7, X7, Z7, K8, P8, T8, W8, X8, Z8, A9, C9, G9,I9, J9, K9, L9, M9, N9, O9, P9, Q9, R9, and A10. In one method, these dyes are used in PCR amplification. In another method, these dyes are used with a target nucleic acid and an unlabeled probe in melting curve analysis. These dyes may be used with various other methods described herein.

In a further embodiment of this invention, a method is provided for nucleic acid analysis comprising the steps of mixing a target nucleic acid with a saturating dsDNA binding dye and at least one unlabeled probe configured to hybridize to a portion of the target nucleic acid, to form a mixture, allowing the unlabeled probe to hybridize to the target nucleic acid to form a probe/target duplex, generating a melting curve for the probe/target duplex by measuring fluorescence from the dsDNA binding dye as the mixture is heated, and analyzing the shape of the melting curve. Illustratively, the shape of the melting curve may be analyzed by generating a derivative melting curve, illustratively by analyzing the shape and location of one or more melting peaks on the derivative melting curve. The analysis optionally may take place during or subsequent to amplification of the target nucleic acid. The saturating dyes described above or other saturating dyes may be used for this method.

In yet another embodiment of this invention, a kit is provided for analyzing a target nucleic acid, the kit comprising an unlabeled probe configured to hybridize at least partially to the target nucleic acid, and a saturating dsDNA binding dye. Optionally, the kit may include other components, illustratively a thermostable polymerase and oligonucleotide primers configured for amplifying the target nucleic acid.

In a further embodiment of this invention, a method of detecting mutations in the c-kit gene is provided comprising providing an amplification mixture comprising a nucleic acid sample, one or more pairs of primers configured for amplifying a locus of the c-kit gene, a thermostable polymerase, and a saturating dsDNA binding dye, amplifying the nucleic acid sample to generate an amplicon, melting the amplicon to generate a melting curve, and analyzing the shape of the melting curve. Illustratively, the primers include any or all of the primers selected from the group consisting of GATGCTCTGCTTCTGTACTG (SEQ ID NO. 40) and GCCTAAACATCCCCTTAAATTGG (SEQ ID NO. 41); CTCTCCAGAGTGCTCTAATGAC (SEQ ID NO. 42) and AGCCCCTGTTTCATACTGACC (SEQ ID NO. 43); CGGCCATGACTGTCGCTGTAA (SEQ ID NO. 44) and CTCCAATGGTGCAGGCTCCAA (SEQ ID NO. 45); and TCTCCTCCAACCTAATAGTG (SEQ ID NO. 46) and GGACTGTCAAGCAGAGAAT (SEQ ID NO. 47).

In still another embodiment, a method for nucleic acid analysis is provided, comprising the steps of mixing a target nucleic acid with a saturating dsDNA binding dye to form a mixture, generating a melting curve for the target nucleic acid by measuring fluorescence from the dsDNA binding dye as the mixture is heated, including in the mixture a second nucleic acid configured to hybridize with a portion of the target nucleic acid, the second nucleic acid being smaller than the target nucleic acid and having a melting temperature different from the target nucleic acid, and allowing the second nucleic acid to hybridize to the portion of the target nucleic acid, melting the second nucleic acid from the first nucleic acid, and analyzing the shape of the melting curve. In one embodiment, the second nucleic acid is an unlabeled probe that may be added prior to or subsequent to generating the melting curve for the target nucleic acid, whereas in another embodiment, the second nucleotide is a smaller amplicon illustratively that may be produced in a single mixture with amplification of the target nucleic acid.

An additional embodiment of the invention is a method of PCR analysis comprising the steps of mixing a dsDNA binding dye with a sample comprising an unknown initial quantity of a target nucleic acid and primers configured for amplifying the target nucleic acid, to form a mixture, amplifying the target nucleic acid in the presence of the dsDNA binding dye, monitoring fluorescence of the dsDNA binding dye throughout a temperature range during a plurality of amplification cycles to generate a plurality of melting curves, and using the melting curves to quantify the initial quantity of the target nucleic acid. Unlabeled probes and/or saturating dyes may be used during amplification.

Additional features of the present invention will become apparent to those skilled in the art upon consideration of the following detailed description of illustrative embodiments.

BRIEF DESCRIPTION OF THE DRAWINGS

FIG. 5A shows the cystic fibrosis map in which the position of an optional label on a primer is marked (star), FIG. 5B shows genotyping using a labeled primer, FIG. 5C shows genotyping using dye S5, and FIG. 5D shows an attempt to genotype using SYBR® Green I (Homozygotes: _.._wt, ___F508del; Heterozygotes: _.._F508del, _.._I507del, ....F508C).

FIG. 12A shows raw data obtained from high resolution melting of quadruplicate samples of each genotype; FIG. 12B shows normalized high resolution melting curves of the quadruplicate samples of the six genotypes; FIG. 12C shows temperature-shifted, normalized, high resolution melting curves of the quadruplicate samples of the six genotypes. The samples were temperature shifted to overlay the curves between 5 and 10% fluorescence; FIG. 12D shows fluorescence difference curves obtained from the data of FIG. 12C. Each difference curve was obtained by subtracting each sample from the normal (AA) curve to obtain the difference data. While quadruplicate samples were run, due to overlap, fewer than four samples appear in some instances.

FIG. 16A shows the full melting curve and FIG. 16B shows an enlarged portion (shown in square in 16A) with the designation of genotype, and designation of individuals in parentheses.

FIG. 18A shows the results of amplification with various ratios of primers (........symmetric (0.5

μM of each primer); ·····symmetric (no template control); ___(light) 0.05 μM sense primer and 0.5 μM reverse primer; ___(heavy) 0.5 μM sense primer and 0.05 μM reverse primer; ____(light) 0.5 μM sense primer and 0.025 μM reverse primer; ____(heavy) 0.025 PM sense primer and 0.5 μM reverse primer; _._(light) 0.5 μM sense primer and 0.01 μM reverse primer; _.._(heavy) 0.01 μM sense primer and 0.5 μM reverse primer).

FIG. 21A shows derivative melting curves for each of the four homozygotes using dye D6 FIG. 21B shows derivative melting curves for the A homozygote and the A/G, A/T, and A/C heterozygotes using dye D6; FIG. 21C shows derivative melting curves for the A homozygote and the A/G, A/T, and A/C heterozygotes using SYBR® Green I; and FIG. 21D shows derivative melting curves for the A homozygote and the G/T, C/G, and C/T heterozygotes using dye D6.

FIGS. 25 A-B are melting curves for a PCR amplicon that includes the cystic fibrosis G542X locus, in which the samples were simultaneously scanned for the mutation by amplicon melting and genotyped by probe melting.

FIGS. 28 A-D show analyses of fluorescence data obtained during each cycle of PCR.

FIG. 29 shows a heterozygous SNP (___normal,____GIST 1), FIG. 30 shows a homozygous 12 bp deletion/SNP (___normal,____GIST 2), FIG. 31 shows a heterozygous tandem duplication (36 bp) (___normal,____GIST 3), and FIG. 32 shows a heterozygous deletion (54 bp) (___normal,____GIST 4).

DETAILED DESCRIPTION

Figure 5A:
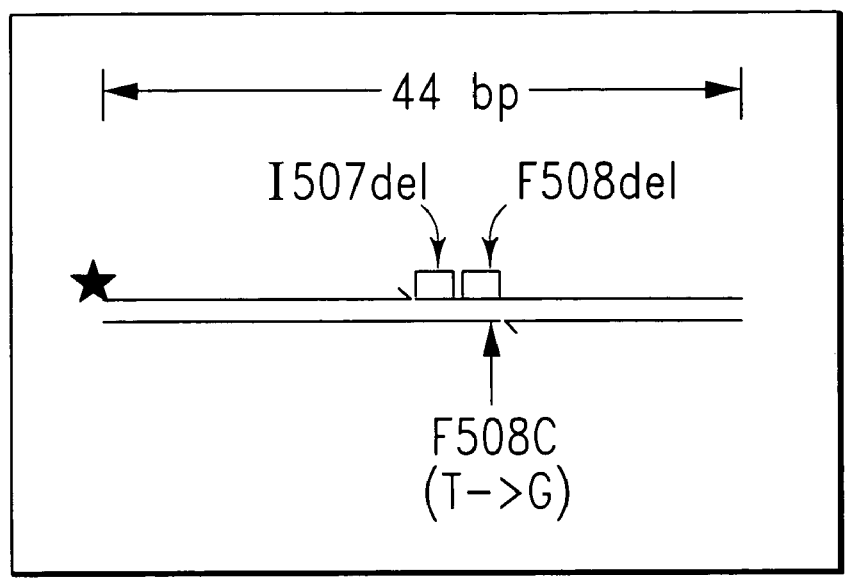
FIGS. 5A-D show a comparison of genotyping methods.

SYBR® Green I is a dye extensively used for melting analysis as it shows a large change in fluorescence during PCR (Wittwer C T, et al., BioTechniques 1997;22:130-1, 134-8; Wittwer C T, et al., Real-Time PCR. In: Persing D, et al., eds. Diagnostic Molecular Microbiology: Principles and Applications. ASM Press, 2004: in press). SYBR® Green I was first used in melting analysis to distinguish different PCR products that differed in Tm by 2° C. or more (Ririe K M, et al., Anal Biochem 1997;245:154-160). Subsequently, SYBR® Green I was used to identify deletions (Aoshima T, et al., Clin Chem 2000;46:119-22), genotype dinucleotide repeats (Marziliano N, et al., Clin Chem 2000;46:423-5), and identify various sequence alterations (Lipsky R H, et al., Clin Chem 2001;47:635-44; Pirulli D, et al., Clin Chem 2000;46:1842-4; Tanriverdi S, et al., J Clin Microbiol. 2002;40:3237-44; Hladnik U, et al., Clin Exp Med. 2002; 2:105-8). However, the Tm difference between genotypes can be small and may challenge the resolution of current instruments. Indeed, it has been suggested that SYBR® Green I, "should not be used for routine genotyping applications" (von Ahsen N, et al., Clin Chem 2001;47:1331-1332). Melting curve genotyping with commonly used double-strand-specific DNA dyes can result an increased Tm with broadening of the melting transition (Douthart R J, et al., Biochemistry 1973;12:214-20), and compression of the Tm difference between genotypes (FIG. 5D). These factors lower the potential of SYBR® Green I for genotype discrimination.

Heterozygous DNA is made up of four different single strands that can create two homoduplex and two heteroduplex products when denatured and cooled. Theoretically, all four products have different Tms and the melting curve should be a composite of all four double-stranded to single-stranded transitions. However, double-strand-specific DNA dyes may redistribute during melting (Aktipis S, et al., Biochemistry 1975;14:326-31), causing release of the dye from low melting heteroduplexes and redistribution to higher melting homoduplexes. Because SYBR® Green I is not saturating at concentrations compatible with PCR (Wittwer C T, et al., BioTechniques 1997;22:130-1, 134-8; FIG. 9), such redistribution is plausible and consistent with the absence of a heteroduplex transition (FIG. 5D).

The dyes of the present invention can be used for genotyping and scanning applications. When only one PCR product is amplified and the sequence is homozygous, only homoduplexes are formed. With the dyes of the present invention, Tm differences between different homoduplex genotypes are not compressed (FIG. 5C), and clear differentiation between genotypes is possible, even for SNPs. The dyes of the present invention can also identify and distinguish multiple products present in a reaction, illustratively homoduplexes generated from amplification of multiple loci or multiple targets that are homozygous. In contrast, most of the time only a few products can be observed with SYBR® Green I, presumably due to dye redistribution (see FIG. 7A).

When one or more heterozygous targets are amplified, heteroduplex products are readily observable with the dyes of the present invention. The ability to detect and identify heteroduplexes is particularly useful for detecting heterozygous genotypes as well as for scanning unknown mutations. This is not possible with conventional dsDNA dyes used in real-time PCR, such as SYBR® Green I, SYBR® Gold, and ethidium bromide, where heteroduplex products are not observable.

Figure 2:
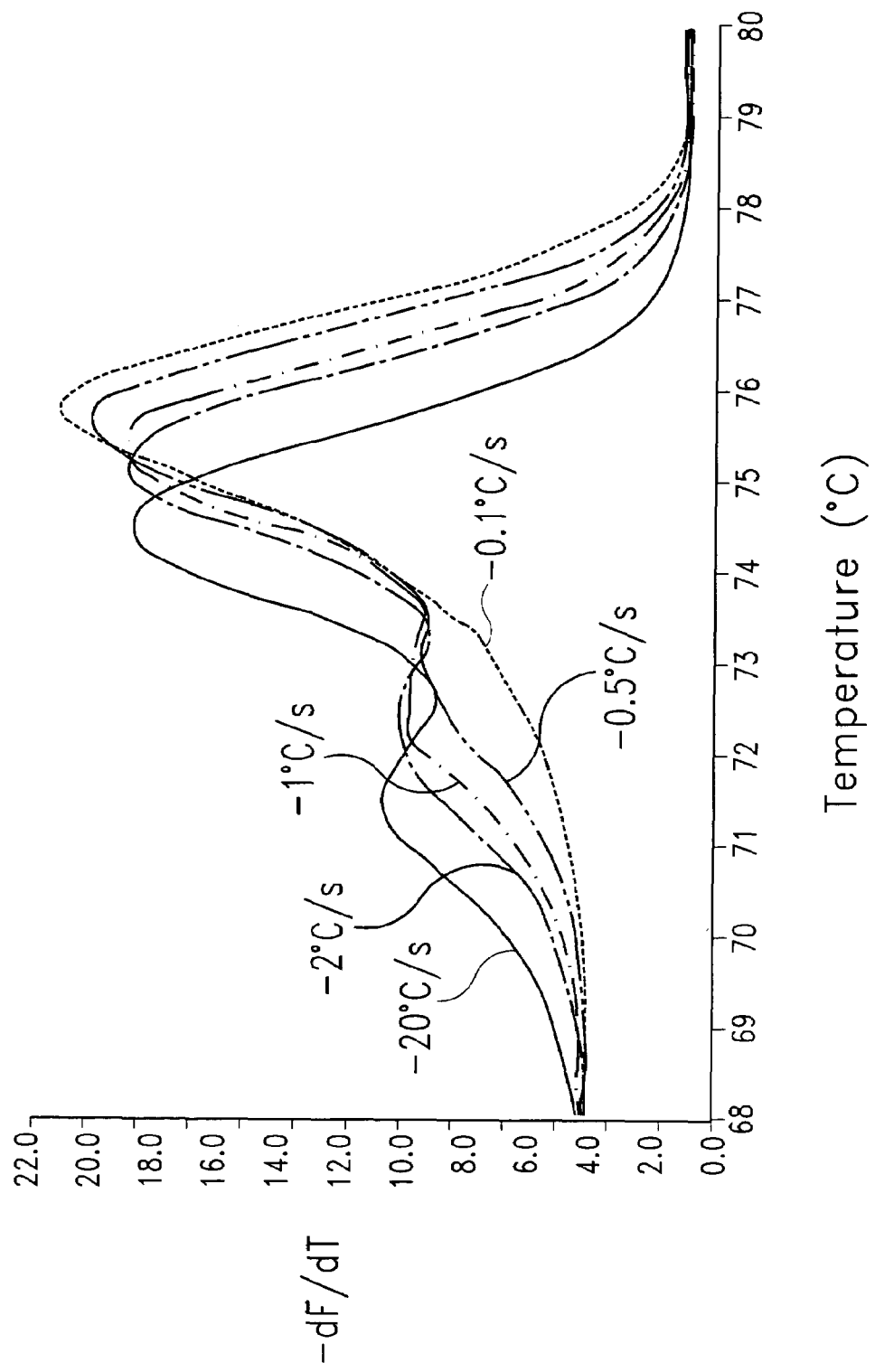
FIG. 2 shows the effect of cooling rates prior to melting analysis on the detection of heteroduplexes.

Heteroduplex strands may re-associate with their perfect complement and form homoduplexes during melting. Because the concentration of products at the end of PCR is high, this re-association happens rapidly. Re-association can be minimized by limiting the time the products are near their melting temperatures, particularly between the Tms of the heteroduplex and homoduplex products. In addition to strand re-association during melting, the selective hybridization of a strand to either its perfect match, or to its mismatched complementary strand, is influenced by cooling rates. Under conditions presented herein, heteroduplex formation is most favored by rapid cooling and often disappears at rates slower than −0.1° C./s (FIG. 2). This is in contrast to denaturing HPLC techniques, where cooling rates are much slower (−0.01 to about −0.02° C./s), yet heteroduplexes are efficiently formed (Xiao W, et al., Hum Mutat 2001;17:439-74). Perhaps the relative rates of homoduplex and heteroduplex formation are strongly dependent on product size, and the results obtained using small amplicons may not be typical for the larger products more commonly used in dHPLC.

The discrimination between homozygous genotypes can be improved by melting at slower rates, at the expense of greater analysis time. One source of potential error in melting curve genotyping is the effect of DNA concentration on Tm. Using a random 100 bp amplicon of 50% GC content under PCR conditions, the difference in Tm between products at 0.05 µM and 0.5 µM is about 0.7° C. (von Ahsen N, et al., Clin Chem 2001;47:1956-61; Wetmur J G, Crit Rev Biochem Mol Biol 1991;26:227-59). This change can be important when the Tms of different homozygous genotypes are very close. However, different PCR samples tend to plateau at the same product concentration, so post-amplification concentration differences are usually minimal. Also, it may be possible to estimate amplicon concentrations by real-time fluorescence and adjust the Tms for even greater genotyping precision. Alternatively, asymmetric PCR may be used to limit automatically the final concentration of PCR product.

With the dyes of the present disclosure, it is possible to distinguish all single base heterozygotes from homozygotes. In the detection of heterozygotes, the absolute melting temperature and the influence of DNA concentration are not as important as with methods involving differentiation between homozygous genotypes. Heteroduplexes affect the shape of the melting curve, particularly at the "early," low temperature portion of the transition. Different melting curves can be temperature matched by translating the X-axis to superimpose the "late," high temperature portion of the transition. The presence or absence of heteroduplexes can then be inferred with greater accuracy. Thus, even in samples obtained without PCR amplification, attention to DNA concentration may not be crucial.

Whatever the precision of the instrument, some genotypes will be nearly identical in Tm. One way to detect homozygous variants with the same Tm is to mix the variants together. The resulting heteroduplexes will melt at lower temperatures than the homoduplexes, displayed as a drop in the normalized melting curves before the major melting transition.

Figure 7A:
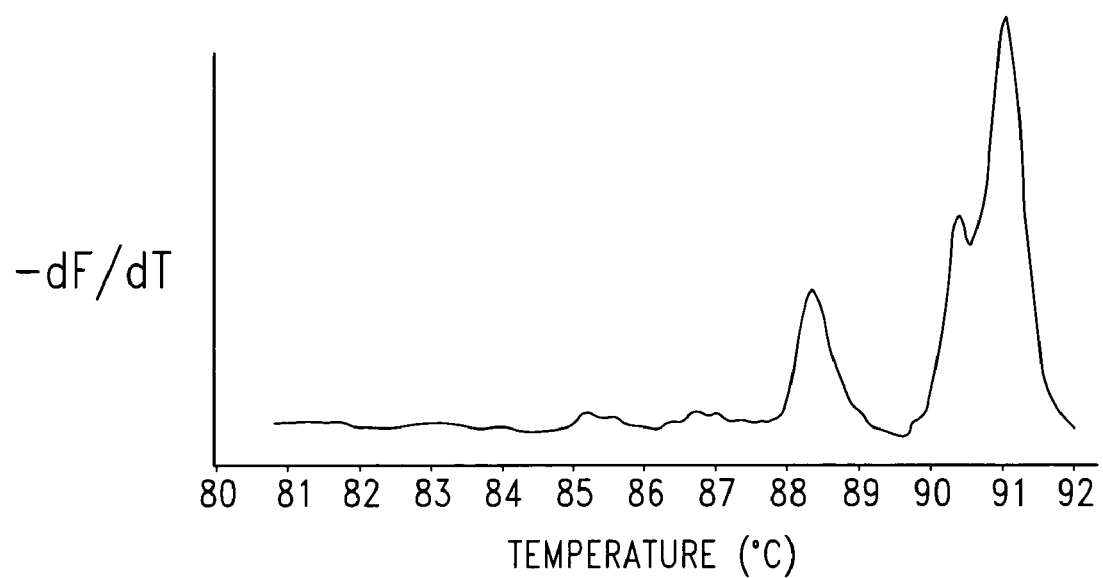
FIGS. 7A-B shows derivative melting curves of DNA mixtures using SYBR® Green I (FIG. 7A) and dye S5 (FIG. 7B).
Figure 7B:
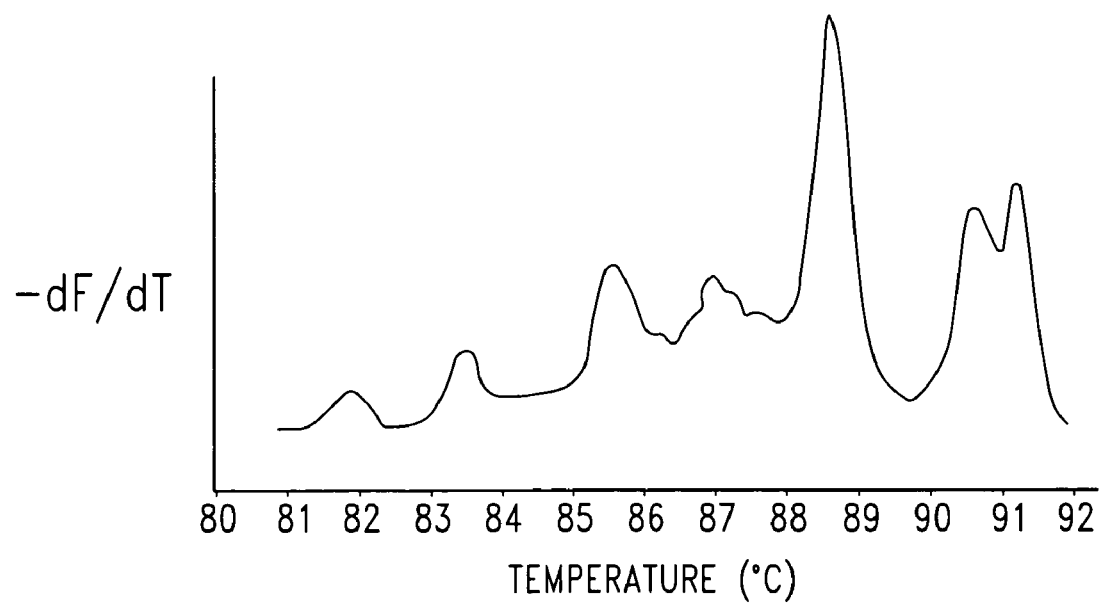

Thus, using presently available PCR amplification devices, the dyes of the present invention can identify heteroduplexes in melting curve transitions that cannot currently be identified using SYBR® Green I. One possible reason why SYBR® Green I cannot easily identify low melting transitions is shown in FIG. 7A. When several DNA fragments of increasing stability are present, the low temperature peaks are very small with SYBR® Green I compared to dyes such as dye S5 (structure shown in Example 1). During melting, SYBR® Green I may be released from low temperature duplexes, only to attach to duplexes that melt at higher temperatures. This causes each successive peak to be higher than the last, with the lowest temperature peaks being very small, if observable at all. As seen in FIG. 7B, low temperature melting products are easily detected with dye S5, but not by SYBR® Green I.

The advantages of using dye S5 have led to identification of other dsDNA dyes that are compatible with PCR and are suited for genotyping at PCR-compatible concentrations. Many of the dyes useful in the methods of the present invention belong to a family of cyanines. Cyanine dyes are those dyes containing one or more divalent moieties "—C(R)=" arranged in a chain that link two nitrogen containing heterocycles. The group "R" may be hydrogen or any carbon substituent, and is illustratively hydrogen or alkyl, including $C_{1-6}$ alkyl, which may be optionally substituted. It is understood that in cyanine dyes where there is more than one divalent moiety "—C(R)=" each "R" may be selected independently. Such cyanine dyes may be monomers or dimers, as further defined by the illustrative general formulae herein described. Many cyanine variants, illustratively dyes in which the divalent moiety is =N—, —C(R)=N—, or the like, are also well suited. In addition to cyanine dyes, it is contemplated herein that other families of dsDNA binding dyes are also useful in the PCR reaction mixtures, methods, and compositions described herein, including but not limited to phenanthridinium intercalators and phenanthroline-based metallointercalators.

Illustrative dyes useful in the present PCR reaction and melting curve mixtures, methods, and compositions include, PO-PRO™-1, BO-PRO™-1, SYTO® 43, SYTO® 44, SYTO® 45, SYTOX® Blue, POPO™-1, POPO™-3, BOBO™-1, BOBO™-3, LO-PRO™-1, JO-PRO™-1, YO-PRO®-1, TO-PRO®-1, SYTO® 11, SYTO® 13, SYTO® 15, SYTO® 16, SYTO® 20, SYTO® 23, TOTO™-3, YOYO®-3 (Molecular Probes, Inc., Eugene, Oreg.), GelStar® (Cambrex Bio Science Rockland Inc., Rockland, Me.), thiazole orange (Aldrich Chemical Co., Milwaukee, Wis.) and various novel dyes described herein.

Illustrative cyanine dyes for use in the PCR reaction mixtures, methods, and compositions described herein also include monomers or dimers of unsymmetrical cyanines having pyridinium, pyrimidinium, quinolinium, isoquinolinium, or purinium core structures, and those generally described by Formula I:

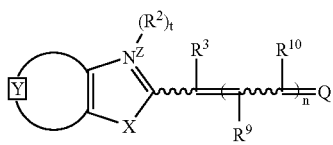

Formula I wherein
the moiety

Y represents an optionally-substituted fused mono or polycyclic aromatic or nitrogen-containing heteroaromatic ring;

X is oxygen, sulfur, selenium, tellurium, or a group selected from $C(CH_3)_2$ and $NR^1$, where $R^1$ is hydrogen or alkyl, including $C_{1-6}$ alkyl and $C_{2-6}$ alkyl;

$R^2$ is alkyl, including $C_{1-6}$ alkyl and $C_{2-6}$ alkyl, cycloalkyl, including $C_{3-8}$ cycloalkyl, aryl, arylalkyl, including aryl ($C_{1-3}$ alkyl), hydroxyalkyl, alkoxyalkyl, aminoalkyl, mono and dialkylaminoalkyl, trialkylammoniumalkyl, alkyl and arylcarbonyl, alkyl and arylcarboxamide, alkyl and arylsulfonyl, alkylenecarboxylate, alkylenecarboxamide, alkylenesulfonate, alkylenesulfonic acid, and the like, a cyclic heteroatom-containing moiety, or an acyclic heteroatom-containing moiety, each of which may be optionally substituted; illustrative heteroatom-containing moieties include optionally substituted heteroalkyl, including methoxymethyl, ethoxyethyl, and the like, heterocyclyl, including piperidinyl, and the like, alkyl and arylsulfonates, including methylsulfonate, 4-chlorophenylsulfonate, and the like, alkoxy, including methoxy, ethoxy, and the like, amino, including methylamino, dimethylamino, and the like, carbonyl derivatives, including alkyl and aryl carbonyl, alkylaminocarbonyl, alkoxycarbonyl, and the like, heteroalkenyl, including alkenylaminoalkyl, alkenyloxyalkyl, alkylaminoalkenyl, alkyloxyalkenyl, alkylideneaminoalkyl, and the like, heteroallyl, esters, amines, amides, phosphorus-oxygen, and phosphorus-sulfur bonds; and including heteroatom-containing moieties as described in U.S. Pat. No. 5,658,751 and PCT Publication No. WO 00/66664; the disclosures of each are herein incorporated in their entirety by reference;

t=0 or 1;

Z is a charge selected from 0 or 1;

$R^3$, $R^9$, and $R^{10}$ are each independently selected from hydrogen, alkyl, including $C_{1-6}$ alkyl and $C_{2-6}$ alkyl, and arylcarbonyl;

n=0, 1,or2;and

Q is a heterocycle, such as a pyridinium, a pyrimidinium, a quinolinium, or a purinium, each of which may be optionally substituted.

The term "alkyl" as used herein generally refers to a linear or optionally branched hydrocarbon moiety comprising from 1 to about 12 carbon atoms, illustratively including but not limited to methyl (Me), ethyl, propyl, butyl, dodecyl, 4-ethylpentyl, and the like.

The term "cycloalkyl" as used herein generally refers to a linear or optionally branched hydrocarbon moiety, at least a portion of which forms one or two rings, comprising from 3 to about 14 carbon atoms, illustratively including but not limited to cyclopropyl, cyclopentyl, cyclohexyl, 4-methylcyclohexyl, 2,3-dimethylcyclopentyl, 3,5-dimethylcyclohexylethyl, and the like.

The term "aryl" as used herein generally refers to a cyclic aromatic moiety, illustratively including but not limited to phenyl (Ph), naphthyl, furyl, thienyl, pyrrolo, pyrazolo, isoxazolyl, isothiazolyl, oxazolyl, thiazolyl, pyridinyl, pyridazinyl, pyrimidinyl, pyrazinyl, quinolinyl, isoquinolinyl, quinoxalinyl, quinazalinyl, and the like.

The term "optionally substituted" as used herein generally refers to the optional replacement of one or more hydrogen atoms or lone electron pairs present on the parent group, including those present on carbon, nitrogen, oxygen, or sulfur atoms, with a substituent, such as halo; hydroxy; amino; nitro; thio; sulfonate; alkyl, cycloalkyl, haloalkyl, halocycloalkyl; alkoxy, cycloalkoxy, haloalkoxy; monoalkyl and dialkylamino; trialkylammonium; aminoalkyl; monoalkyl and dialkylaminoalkyl; trialkylammoniumalkyl; trialkylammoniumalkylthio; alkylthio; cycloalkylthio, cycloheteroalkylthio, nucleosidylthio; alkyl, haloalkyl, cycloalkyl, and arylcarbonyl; arylcarbonylthio, cycloheteroalkylcarbonylthio, dialkylaminoalkylcarbonylthio; alkyl, haloalkyl, cycloalkyl, and arylcarbonyloxy; alkyl, haloalkyl, cycloalkyl, and arylsulfonyl; and carboxyl derivatives, such as carboxylic acids, esters, and amides. It is appreciated that the replacement of proximal hydrogen atoms, including geminal and vicinal hydrogens, may be such that the substituents replacing those proximal hydrogens are taken together to form a spiro ring or a fused ring, respectively.

It is appreciated that each of the above described terms may be used in combination in chemically relevant ways to refer to other moieties, such as arylalkyl referring to an aryl group as defined herein linked to an alkyl group as defined herein to form structures including, but not limited to, benzyl, phenethyl, picolinyl, 3,5-dimethoxypicolin-4-yl, and the like.

It is appreciated that the cyanine dye structures described herein may contain chiral centers. In those cases, all stereoisomers are understood to be included in the description of these cyanine dye structures, unless otherwise indicated. Such stereoisomers include pure optically active isomers, racemic mixtures, and mixtures of diastereomers containing any relative amount of one or more stereoisomeric configurations.

It is also appreciated that the cyanine dye structures described herein may contain geometric centers. In those cases, all geometric isomers are understood to be included in the description of the cyanine dye structures, unless otherwise indicated. Such geometric isomers include cis, trans, E and Z isomers, either in pure form or in various mixtures of geometric configurations. It is also understood that depending upon the nature of the double bond contained in the cyanine dye structures, such double bond isomers may interconvert between cis and trans, or between E and Z configurations depending upon the conditions, such as solvent composition, solvent polarity, ionic strength, and the like.

It is further appreciated that when the charge Z is greater than 0, several resonance structures of the compounds of Formula I may exist. Illustratively, the charge Z may be formally localized on the nitrogen atom as depicted in Formula I, or alternatively, the charge may be localized on the heterocycle Q. Resonance structures of the charged compounds of Formula I may be depicted by rearranging the double bond-single bond configuration of compounds of Formula I, such as the illustrative structures:

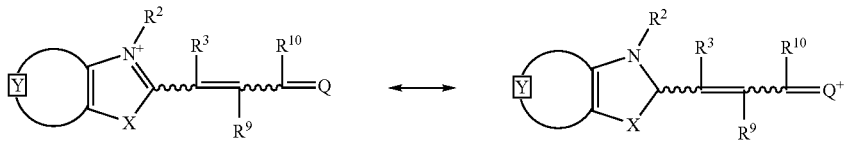

wherein

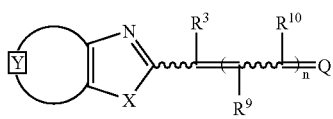,

X, $R^2$, $R^3$, $R^9$, $R^{10}$, and Q, are as defined for Formula I, and t=1, Z=1, and n=1. The cyanine dye compounds described herein include any of the several possible resonance structures. It is understood that the location of the formal charge and, hence, the favored resonance structure, is influenced by the nature of the moieties

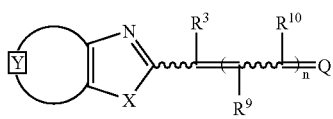,

X, $R^2$, $R^3$, $R^9$, $R^{10}$, and Q.

It is also understood that when compounds of Formula I carry a net charge, such as where Z is 1, or where there is present on the compounds of Formula I a charged substituent, such as an ammonium group, or a sulfonic acid group, these compounds of Formula I are accompanied by a counter ion. Any monovalent, divalent, or polyvalent counter ion is included in the description of the cyanine dye structures contained herein. Illustrative counter-ions include negatively charged counter ions such as iodide, chloride, bromide, hydroxide, oxide, acetate, trifluoroacetate, monophosphate, diphosphate, triphosphate, and the like, and positively charged counter ions such as lithium, sodium, potassium, cesium, ammonium, polyalkylammonium, and the like. Such counter ions may arise from the synthetic methods used, the purification protocol, or other ion exchange processes.

It is believed that the nature or type of counter ion does not appear to influence the functionality of the cyanine dyes described herein. It is appreciated that when the dyes described herein are dissolved in solvents or other media used to practice the PCR reaction mixtures, methods, and compositions described herein, the accompanying counter ion may exchange with other counter ions that are present in the solvents or other media. Such additional counter ions may be solvent ions, salts, buffers, and/or metals.

It is appreciated that the group $R^2$ may be virtually any group that arises from the nucleophilic reaction between the parent compound of Formula I, where t=Z=0:

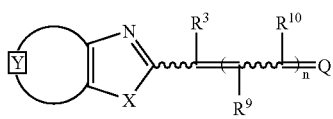

and a compound having the formula $R^2$-L, wherein L is a suitable leaving group, and $R^2$ is as defined above. Illustratively, $R^2$ is an optionally substituted alkyl, acyl, aryl, sulfonic acid, or sulfonyl group, each of which may be optionally substituted. Illustrative leaving groups L include, but are not limited to halides, such as chloride and bromide, acylates, such as acetate, formate, and trifluoroacetate, sulfonates, such as methylsulfonate, trifluoromethylsulfonate, and tolylsulfonate, sulfates, such as methylsulfate, and the like.

In one illustrative embodiment, Q is an heterocycle such as, but not limited to:

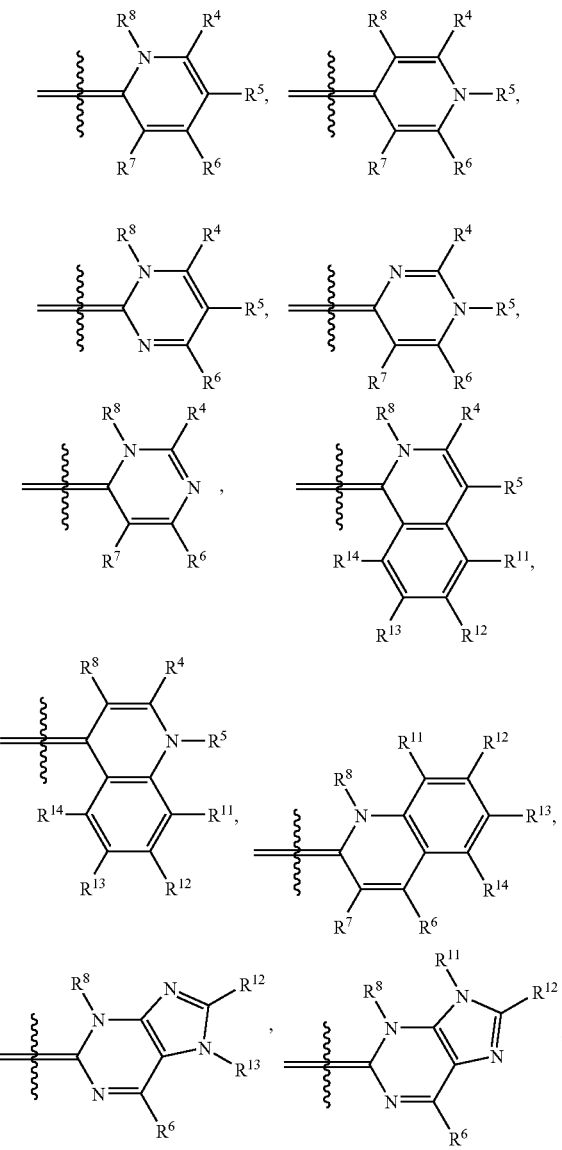

-continued

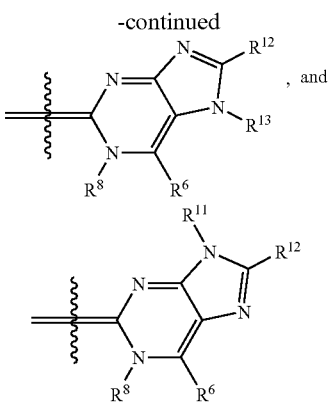
, and wherein $R^4$, $R^5$, $R^6$, $R^7$, $R^8$, $R^{11}$, $R^{12}$, $R^{13}$, and $R^{14}$ are each independently selected from the group consisting of hydrogen, halogen, amino, alkyl, haloalkyl, alkoxy, haloalkoxy, alkylsulfonyl, haloalkylsulfonyl, arylsulfonyl, formyl, alkylcarbonyl, arylcarbonyl, carboxylic acid derivatives, monoalkylamino, dialkylamino, trialkylammonium, dialkylaminoalkyl, trialkylammoniumalkyl, trialkylammoniumalkylthio, cycloalkyl, heteroalkyl, heterocycloalkyl, alkenyl, polyalkenyl, alkynyl, polyalkynyl, alkenylalkynyl, aryl, heteroaryl, alkoxy, alkylthio, arylthio, arylcarbonylthio, cycloheteroalkylcarbonylthio, dialkylaminoalkylcarbonylthio, dialkylamino, cycloalkylthio, cycloheteroalkylthio, nucleosidylthio, each of which may be optionally substituted, piperidino, piperazino, each of which may be optionally substituted with alkyl, amino, mono or dialkylaminoalkyl, trialkylammoniumalkyl, or may be optionally quaternized on the nitrogen with an alkyl group.

In another illustrative embodiment, one of $R^4$, $R^5$, $R^6$, $R^7$, $R^8$, $R^{11}$, $R^{12}$, $R^{13}$, and $R^{14}$ is an heteroatom-containing moiety, as described in U.S. Pat. No. 5,658,751. In another illustrative embodiment, one of $R^4$, $R^5$, $R^6$, $R^7$, $R^8$, $R^{11}$, $R^{12}$, $R^{13}$, and $R^{14}$ is a reactive group, including but not limited to halogens, hydroxy, alkoxides, amines, carboxylic acids, halides, alcohols, aldehydes, thiols, alkyl, and arylthiols, alkyl and arylsulfonyls, succinimidyl esters, ketones, and isothiocyanates that may be used to attach moieties to the dye core structure, illustratively through the formation of carbon-carbon bonds, amines, amides, ethers, thioethers, disulfides, ketones, thioureas, and Schiff bases. In another illustrative embodiment, one of $R^4$, $R^5$, $R^6$, $R^7$, $R^8$, $R^{11}$, $R^{12}$, $R^{13}$, and $R^{14}$ is a BRIDGE-DYE having the formula:

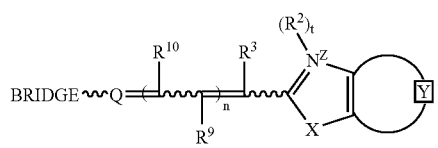

wherein $\boxed{Y}$,

X, $R^2$, t, Z, $R^3$, $R^9$, $R^{10}$, Q, and n are as defined for Formula I, and BRIDGE is a single covalent bond, or a covalent linkage that is linear or branched, cyclic or heterocyclic, saturated or unsaturated, having 1-16 non-hydrogen atoms such as carbon, nitrogen, phosphate, oxygen, and sulfur, such that the linkage contains any combination of alkyl, ether, thioether, amine, ester, or amide bonds; single, double, triple, or aromatic carbon-carbon bonds; phosphorus-oxygen, phosphorus-sulfur, nitrogen-nitrogen, or nitrogen-oxygen bonds; or aromatic or heteroaromatic bonds. It is appreciated that in some embodiments, this dimeric structure is symmetrical about BRIDGE, and in other embodiments, this dimeric structure is unsymmetrical about BRIDGE, wherein for example, any of $\boxed{Y}$, X, $R^2$, t, Z, $R^3$, $R^9$, $R^{10}$, and n are each independently selected in each occurrence on each side of BRIDGE.

Illustrative dyes for use in the present invention also include cyanine dyes of Formula I having a pyridinium or pyrimidinium core structure wherein X is oxygen or sulfur; the moiety $\boxed{Y}$ represents an optionally-substituted fused benzo, optionally-substituted fused naphthaleno, optionally-substituted fused pyridino, optionally-substituted fused pyrimidino, optionally-substituted fused quinolino, and the like; n=0 or 1; t=0 or 1; $R^2$ is alkyl, such as methyl and ethyl, optionally substituted aryl, such as phenyl or tolyl, an alkylenesulfonate, such as propylenesulfonic acid, or alkylsulfonyl, such as $CH_3(CH_2)_mSO_2$, where m is 0, 1, 2, or 3; and Q is an heterocycle selected from the group of structures consisting of:

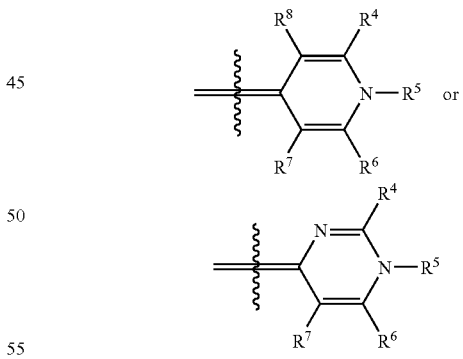

wherein $R^4$ is hydrogen, alkoxy, including methoxy, ethoxy, propyloxy, and the like; alkylthio, including methylthio, ethylthio, and the like; heterocyclylalkyl, including optionally substituted piperidinyl, pyrrolidinyl, piperazinyl, and the like; or heterocyclylalkyl including a charged group, including 4,4-dimethylpiperazinium-1-yl, and the like; or a reactive group, including halo, hydroxy, alkoxy, thio, alkyl and arylthio, alkyl and arylsulfonyl, amino, formyl, alkyl and arylcarbonyl, carboxyl derivatives, and the like;

$R^5$ is $C_{1-6}$ alkyl, including methyl, ethyl, butyl, sec-butyl, isobutyl, and the like; optionally substituted phenyl; or $(CH_2)_3N^+(Me)_3$; and $R^6$, $R^7$, and $R^8$ are each independently hydrogen or methyl.

Illustrative dyes for use herein also include cyanine dyes of Formula I having a pyridinium or pyrimidinium core structure wherein X is oxygen or sulfur; the moiety $$Y$$

represents an optionally-substituted fused benzo, forming an optionally substituted benzoxazolium or benzthiazolium ring, or an optionally-substituted fused naphtho, forming an optionally substituted naphthoxazolium or naphthothiazolium ring; n=0 or 1; t=0 or 1; $R^2$ is alkyl, such as methyl, aryl, such as phenyl or tolyl, an alkylenesulfonate, such as propylenesulfonic acid, or alkylsulfonyl, such as $CH_3(CH_2)_m SO_2$, where m is 0, 1, 2, or 3; and Q is a 4-pyridinium or 4-pyrimidinium heterocycle.

Illustrative dyes for use herein also include cyanine dyes useful in the PCR reaction mixtures, methods, and compositions described herein with quinolinium core structures, and generally described by Formula II:

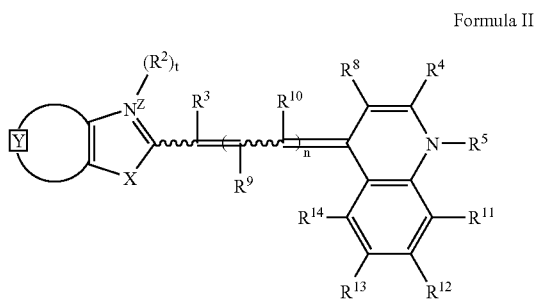

Formula II wherein
the moiety $$Y$$

represents an optionally-substituted fused mono or polycyclic aromatic or nitrogen-containing heteroaromatic ring;

X is oxygen, sulfur, or a group selected from $C(CH_3)_2$, and $NR^1$, where $R^1$ is hydrogen or $C_{1-6}$ alkyl;

$R^2$ is alkyl, including $C_{1-6}$ alkyl and $C_{2-6}$ alkyl, cycloalkyl, including $C_{3-8}$ cycloalkyl, aryl, arylalkyl, an alkylenesulfonate, a cyclic heteroatom-containing moiety, or an acyclic heteroatom-containing moiety, each of which may be optionally substituted;

t=0 or 1;

Z is a charge selected from 0 or 1;

$R^3$, $R^9$, and $R^{10}$ are each independently selected from hydrogen and alkyl, including $C_{1-6}$ alkyl;

n=0, 1, or 2; and $R^4$, $R^5$, $R^8$, $R^{11}$, $R^{12}$, $R^{13}$, and $R^{14}$ are as described herein for Formula I, providing that $R^4$ is a moiety with a molecular weight of less than about 115, or illustratively a molecular weight of less than about 105.

Illustrative dyes for use in the present invention also include cyanine dyes of Formula II wherein the moiety $$Y$$

represents an optionally-substituted fused benzo, thereby forming a benzoxazolium or benzthiazolium ring; X is oxygen or sulfur; n=0 or 1; t=0 or 1; $R^2$ is methyl;

$R^4$ is hydrogen, $C_{1-6}$ alkyl, including methyl, or optionally-substituted phenyl;

$R^5$ is $C_{1-6}$ alkyl, including methyl, or optionally-substituted phenyl;

$R^8$ is hydrogen, and $R^{11}$, $R^{12}$, $R^{13}$, and $R^{14}$ are hydrogen or alkoxy, including methoxy.

In other embodiments, dyes for use in the present invention also illustratively include cyanine dyes of Formula II wherein the moiety $$Y$$

represents an optionally-substituted heterocycle, including 1-methylpyrido and 3-bromo-1-methylpyrido; X is oxygen or sulfur; n=0 or 1; t=z=0;

$R^4$ is hydrogen or $C_{1-6}$ alkyl, including methyl;

$R^5$ is $C_{1-6}$ alkyl, including methyl, optionally-substituted phenyl or heteroalkyl, including heteroalkyl having a charged group such as the group —$(CH_2)_3N(Me)_3$;

$R^8$ is hydrogen; and $R^{11}$, $R^{12}$, $R^{13}$, and $R^{14}$ are hydrogen, alkyl, including methyl, or alkoxy, including methoxy.

In another embodiment, two compounds of Formula I are taken together to form a dimer. The two compounds are linked to each other by replacing one of the substituents $R^4$, $R^5$, $R^6$, $R^7$, $R^8$, $R^{11}$, $R^{12}$, $R^{13}$, and $R^{14}$, as defined above, present on each of the compounds of Formula I with a single divalent linker. Illustratively, two compounds of Formula I are taken together to form a dimer, where the two $R^5$ substituents present on the two compounds of Formula I are replaced with a single divalent linker. It is appreciated that both symmetrical and unsymmetrical dimers of Formula I compounds are contemplated herein. In the case of unsymmetrical dimers of compounds of Formula I, it is understood that such asymmetry may arise by forming dimers from compounds of Formula I having different substitution patterns, or having different heterocycles Q. Further, such asymmetry may arise by forming dimers from compounds of Formula I where different substituents are replaced with the divalent linker, such as illustratively replacing $R^5$ on a first compound of Formula I and replacing $R^8$ on a second compound of Formula I with the divalent linker.

In another embodiment, two compounds of Formula II are taken together to form a dimer. The two compounds are linked to each other by replacing one of the substituents $R^4$, $R^5$, $R^8$, $R^{11}$, $R^{12}$, $R^{13}$, and $R^{14}$, as defined above, present on each of the compounds of Formula II with a single divalent linker. Illustratively, two compounds of Formula II are taken together to form a dimer, where the two $R^5$ substituents present on the two compounds of Formula II are replaced with a single divalent linker. It is appreciated that both symmetrical and unsymmetrical dimers of Formula II compounds are contemplated herein. In the case of unsymmetrical dimers of compounds of Formula II, it is understood that such asymmetry may arise by forming dimers from compounds of Formula II having different substitution patterns, or having different heterocycles Q. Further, such asymmetry may arise by forming dimers from compounds of Formula II where different substituents are replaced with the divalent linker, such as illustratively replacing $R^5$ on a first compound of Formula II and replacing $R^8$ on a second compound of Formula II with the divalent linker.

The dimeric cyanine dye structures formed by compounds of Formula I may also be represented by Formula III:

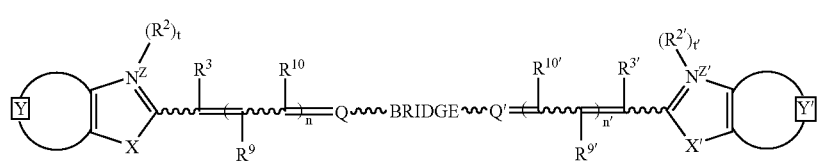

Formula III wherein the moieties

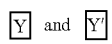

each represent an independently selected optionally-substituted fused mono or polycyclic aromatic or nitrogen-containing heteroaromatic ring;

X and X' are each independently selected from oxygen, sulfur, selenium, tellurium, or a group selected from $C(CH_3)_2$, $NR^1$, or $NR^{1'}$, where $R^1$ and $R^{1'}$ are each independently hydrogen or $C_{1-6}$ alkyl;

$R^2$ and $R^{2'}$ are each independently selected from alkyl, including $C_{1-6}$ alkyl, cycloalkyl, including $C_{3-8}$ cycloalkyl, aryl, arylalkyl, including aryl($C_{1-2}$ alkyl), a cyclic heteroatom-containing moiety, or an acyclic heteroatom-containing moiety, each of which may be optionally substituted;

t=0 or 1;

t'=0 or 1;

Z and Z' are each a charge independently selected from 0 or 1;

$R^3$, $R^9$, $R^{10}$, $R^{3'}$, $R^{9'}$, and $R^{10'}$ are each independently selected from hydrogen and alkyl, including $C_{1-6}$ alkyl;

n=0, 1, or 2;

n'=0, 1, or 2;

BRIDGE is a divalent linker comprising 2 to about 30 divalent units selected from alkylene, heteroalkylene, alkylamindiyl, alkylalkylammoniumdiyl, and the like, such as $(CH_2)_p$, $(CH_2)_pN^+Me_2(CH_2)_q$, $(CH_2)_pN^+Me_2(CH_2)_qN^+Me_2(CH_2)_r$, and the like, where p, q, and r are each independently selected from 1, 2, and 3; and Q and Q' are heterocycles, each independently selected from the group of structures consisting of:

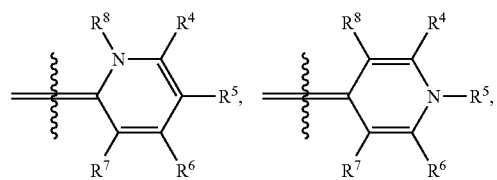

-continued

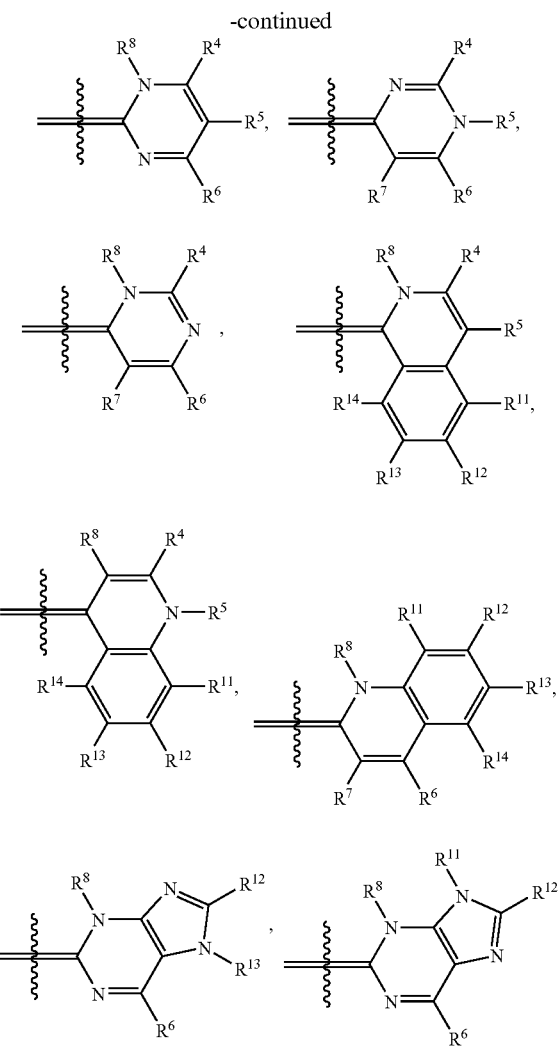

-continued

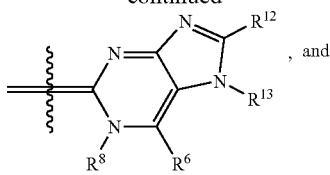

, and

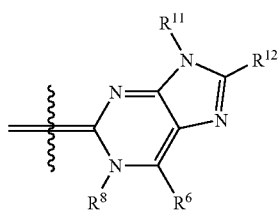

wherein $R^4$, $R^5$, $R^6$, $R^7$, $R^8$, $R^{11}$, $R^{12}$, $R^{13}$, and $R^{14}$ are in each occurrence in compounds of Formula III independently selected from the group consisting of hydrogen, halogen, amino, alkyl, haloalkyl, alkoxy, haloalkoxy, alkylsulfonyl, haloalkylsulfonyl, arylsulfonyl, formyl, alkylcarbonyl, arylcarbonyl, carboxylic acid derivatives, monoalkylamino, dialkylamino, trialkylammonium, dialkylaminoalkyl, trialkylammoniumalkyl, trialkylammoniumalkylthio, cycloalkyl, heteroalkyl, heterocycloalkyl, alkenyl, polyalkenyl, alkynyl, polyalkynyl, alkenylalkynyl, aryl, heteroaryl, alkoxy, alkylthio, arylthio, arylcarbonylthio, cycloheteroalkylcarbonylthio, dialkylaminoalkylcarbonylthio, dialkylamino, cycloalkylthio, cycloheteroalkylthio, nucleosidylthio, each of which may be optionally substituted, piperidino, piperazino, each of which may be optionally substituted with alkyl, amino, mono or dialkylaminoalkyl, trialkylammoniumalkyl, or may be optionally quaternized on the nitrogen with an alkyl group.

Illustrative cyanine dyes useful in the present PCR reaction mixtures, methods, and compositions also include, but are not limited to, S5, PO-PRO™-1, BO-PRO™-1, SYTO® 43, SYTO® 44, SYTO® 45, SYTOX® Blue, POPO™-1, POPO™-3, BOBO™-1, BOBO™-3, and other dyes having the general Formulae IV:

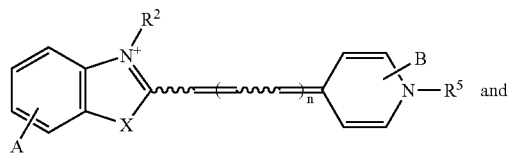

Formula IVa

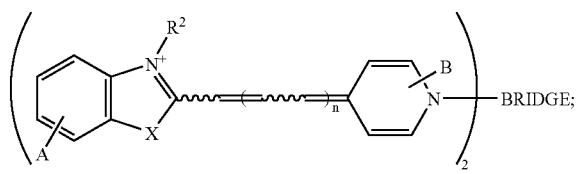

Formula IVb and various novel dyes presented in Example 1, and other dyes having the general Formulae V:

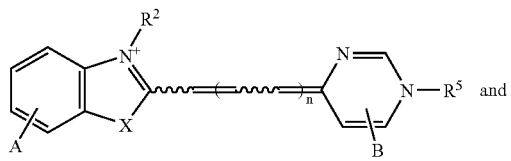

Formula Va

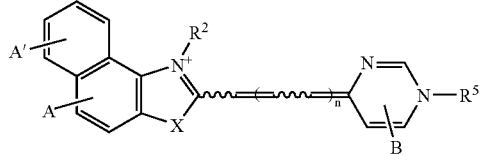

Formula Vb wherein n is 0, 1, or 2; $R^2$ is alkyl, hydroxyalkyl, alkoxyalkyl, aminoalkyl, mono and dialkylaminoalkyl, trialkylammoniumalkyl, alkylenecarboxylate, alkylenecarboxamide, alkylenesulfonate, and the like; $R^5$ is alkyl, hydroxyalkyl, alkoxyalkyl, aminoalkyl, mono or dialkylaminoalkyl, trialkylammoniumalkyl, alkylenecarboxylate, alkylenecarboxamide, alkylenesulfonate, optionally substituted phenyl, and the like; X is oxygen or sulfur; A, A', and B each represent one or more independently selected optional substituents, such as alkyl, halo, amino, haloalkyl, alkoxy, haloalkoxy, alkyl and arylsulfonyl, haloalkylsulfonyl, alkyl and arylthio, formyl, alkyl and arylcarbonyl, carboxyl derivatives, mono and dialkylamino, trialkylammonium, dialkylaminoalkyl, trialkylammoniumalkyl, trialkylammoniumalkylthio, cycloalkyl, heteroalkyl, heterocycloalkyl, alkenyl, polyalkenyl, alkynyl, polyalkynyl, alkenylalkynyl, aryl, heteroaryl, arylcarbonylthio, cycloheteroalkylcarbonylthio, dialkylaminoalkylcarbonylthio, dialkylamino, cycloalkylthio, cycloheteroalkylthio, nucleosidylthio, or a heterocycle including pyrrolidino, piperidino, piperazino, each of which may be optionally substituted with alkyl, amino, mono or dialkylaminoalkyl, trialkylammoniumalkyl or may be optionally quaternized on the nitrogen with an alkyl group, and the like; and BRIDGE is a divalent linker having the formula $(CH_2)_pN^+Me_2(CH_2)_q$, where p and q are independently 2 or 3, which includes the divalent linker $(CH_2)_3N^+Me_2(CH_2)_3$. It is understood that when these dyes have a net charge, they are accompanied by one or more counter ions, such as counter anions including halide, alkanoate, phosphate, and the like, and counter cations including lithium, sodium, potassium, cesium, ammonium, and the like.

Other illustrative dyes for use herein include, but are not limited to YO-PRO®-1, TO-PRO®-1, SYTO® 11, SYTO® 13, SYTO® 15, SYTO® 16, SYTO® 20, SYTO® 23, TOTO™-3, YOYO®-3 (Molecular Probes, Inc.), GelStar® (Cambrex Bio Science Rockland Inc., Rockland, Me.), thiazole orange (Aldrich), and other dyes having the general Formulae VI:

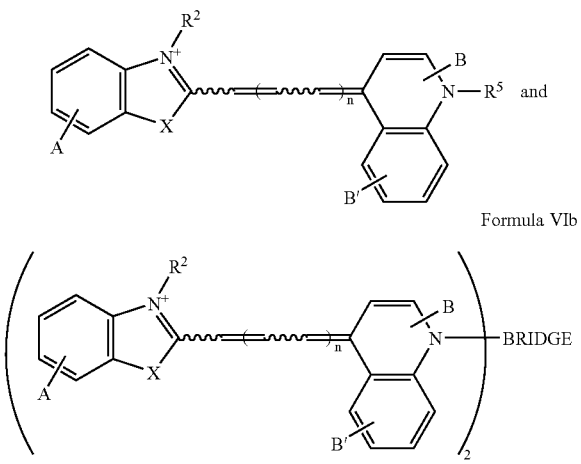

Formula VIa

Formula VIb wherein n is 0, 1, or 2; $R^2$ is alkyl, hydroxyalkyl, alkoxyalkyl, aminoalkyl, mono and dialkylaminoalkyl, trialkylammoniumalkyl, alkylenecarboxylate, alkylenecarboxamide, alkylenesulfonate, and the like; $R^5$ is alkyl, hydroxyalkyl, alkoxyalkyl, aminoalkyl, mono or dialkylaminoalkyl, trialkylammoniumalkyl, alkylenecarboxylate, alkylenecarboxamide, alkylenesulfonate, optionally substituted phenyl, and the like; X is oxygen or sulfur; A, B, and B' each represent one or more independently selected optional substituents, such as alkyl, halo, amino, mono and dialkylamino, pyrrolidino, piperidino, piperazino, phenyl, hydroxy, alkoxy, thio, and alkylthio, trialkylammoniumalkylthio, cycloalkyl, heteroalkyl, heterocycloalkyl, alkenyl, polyalkenyl, alkynyl, polyalkynyl, alkenylalkynyl, aryl, heteroaryl, arylcarbonylthio, cycloheteroalkylcarbonylthio, dialkylaminoalkylcarbonylthio, dialkylamino, cycloalkylthio, cycloheteroalkylthio, nucleosidylthio, each of which may be optionally substituted with alkyl, amino, mono or dialkylaminoalkyl, trialkylammoniumalkyl, and the like; and BRIDGE is a divalent linker having the formula $(CH_2)_p N^+Me_2(CH_2)_q$, where p and q are independently 2 or 3, which includes the divalent linker $(CH_2)_3N^+Me_2(CH_2)_3$. It is understood that when these dyes have a net charge, they are accompanied by one or more counter ions, such as counter anions including halide, alkanoate, phosphate, and the like, and counter cations including lithium, sodium, potassium, cesium, ammonium, and the like.

Initial results have indicated that S5, PO-PRO™-1, JO-PRO™-1, BO-PRO™-1, G5, H5, S5, D6, E6, P6, R6, Y6, Z6, N7, O7, P7, Q7, R7, T7, V7, Z7, G8, L8, P8, T8, V8, W8, Z8, A9, C9, G9, I9, J9, K9, L9, M9, N9, O9, and P9 are quite promising dyes for heteroduplex detection. There are several surprising characteristics of these dyes. First, they do not significantly inhibit PCR at 50% saturation. In fact, saturation levels fairly close to 100% are compatible with PCR with most of these dyes. Secondly, although some of the dyes emit in the blue range, they are compatible with use in the fluorescein channel of a variety of currently available instruments. Adjustment of the optics to better match the excitation/emission spectra of these dyes may further improve their sensitivity for use in quantitative or qualitative amplification analysis.

It is understood that the above cyanine dyes are illustrative, and other cyanine dyes may be useful in the presently-described methods.

Some quinolinium-based unsymmetrical cyanines such as, but not limited to, SYBR® Green I, SYTOX® Green, SYTO® 14, SYTO® 21, SYTO® 24, SYTO® 25, TOTO™-1 and YOYO®-1 have not proven useful for heteroduplex detection or for the detection of multiple products in a closed-tube system. When the dye is a monomer of a quinolinium-based cyanine, it is possible that bulky substitutions on the carbon next to the nitrogen of the quinolonium ring (position equivalent to $R^4$) interfere with the dye's ability to function in the methods of the present invention. Bulky substitutions are, for example, long-chain branched hetero-atom-containing aliphatic or aromatic moieties substituted with branched-chain aliphatic moieties that are larger than MW of about 105. This restriction, however, does not apply to any of the pyridinium or pyrimidinium cyanines mentioned earlier. In the case of quinolinium-based cyanine dimers, the distance between the left and right ring systems, as defined by the divalent fragment:

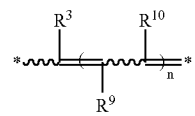

also appears to affect functionality. Functionality may be determined by heteroduplex detection, as taught herein in Example 1. Other dyes previously described as useful in real-time monitoring of PCR, such as SYBR® Gold, Pico Green, and ethidium bromide have also been shown to be ineffective in heteroduplex detection in a closed-tube PCR system.

The dyes for use in the present invention may be used in a dye-based method for SNP genotyping, requiring only two unlabeled oligonucleotide primers and one well for each SNP genotype, and not requiring real-time PCR. A dsDNA dye is used such that heterozygotes are identified by the presence of heteroduplexes that alter the shape of the post-amplification melting curve. Different homozygous genotypes are differentiated by their Tm difference, or alternately by mixing a known homozygous DNA sample with the unknown and looking for heteroduplexes. Illustratively, PCR primer design is greatly simplified because very short amplicons can be used, preferably immediately flanking the SNP. Such short amplicons also amplify very efficiently, reduce the risk of amplifying alternate targets, and allow very rapid thermal cycling.

The design of PCR primers is not an exact science, and often trial and error is necessary. Although some rules for PCR primer design are generally accepted, the validity of these rules has not been tested. Because the effect of different genotypes on melting curves is greater with short amplicons, short amplicons are preferred ($\leq 100$ bp), and the shortest possible amplicons are often best ($\leq 50$ bp). Therefore, to design primers for genotyping with dsDNA dyes, one illustratively starts with each flanking primer right next to the SNP position. That is, the amplicon length will be the length of primer 1, plus the length of primer 2, plus the length of the region that needs to be tested (the length of an SNP is 1). For efficient amplification, the melting temperature (Tm) of the two primers should be nearly the same. Convenient Tms for primers may be 50 to 70 degrees C. Primers with the highest Tm illustratively will allow the fastest thermal cycling, while primers with lower Tm are generally less expensive and produce the shortest amplicons, resulting in greater genotyping differences. Primer lengths between 12 and 30 bases are usually used. Illustratively, each primer is built away from the SNP until the calculated Tm is closest to the desired Tm. Methods for Tm calculation are well known in the art (e.g. Clin. Chem. 2001;47:1956-61). In general, the primer lengths will not be the same when the Tms are matched as closely as possible. For example, the primer lengths used in the Factor V SNP assay (FIG. 1) are 17 and 24 bases long both with a calculated matched Tm near 62° C.

Thermal cycling parameters for amplification can be very short because little primer extension is required for such short amplicons. After an initial denaturation of genomic DNA before thermal cycling, denaturation and annealing temperatures do not need to be held, and the extension time can be 10 s or less. It is even possible to reduce the programmed extension time to zero, allowing each cycle to be performed in less than 20 s. Alternately, an extension time of 1 s can be used. Because the amplicon is so short, large amounts of polymerase are not required (<0.6 Units per 10 µl may be used).

Thus, the following illustrative steps may be followed for SNP genotyping according to the present invention:

1. Choose a target Tm and start with the 3' end of each primer right next to the SNP position. Optionally, one primer may be shifted slightly away from the SNP position to avoid 3' complementarity between primers to decrease the risk of primer dimer formation.

2. Design each primer outward until the calculated Tm is as close as possible to the target Tm.

3. Rapidly thermal cycle the sample in the presence of PCR reagents and a dsDNA dye that allows heteroduplex detection.

4. Form heteroduplexes by rapid cooling at a rate of at least −0.1° C./s, preferably at least −2° C./s, and most preferably at least −5° C./s after denaturation.

5. Heat at 0.1 to 0.5° C./s and acquire a melting curve.

6. If the amplification fails, move the 3'-end of one of the primers out 1 base and repeat all steps until successful.

Figure 4A:
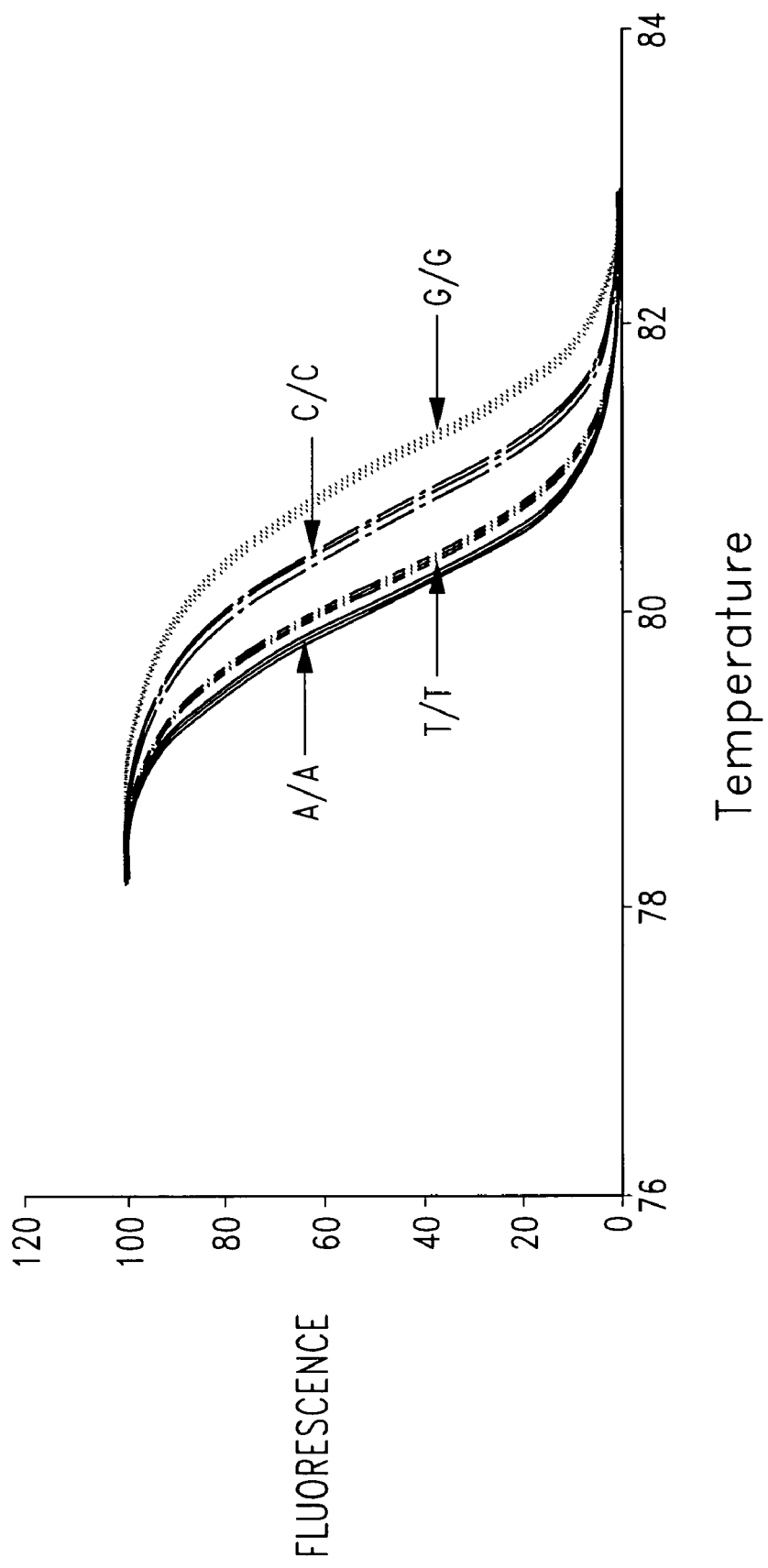
FIGS. 4A-B are normalized, high resolution melting curves of all possible SNP genotypes at one position using an engineered plasmid. Three samples of each genotype were analyzed and included four homozygotes (FIG. 4A, ___A/A, _._,T/T, _.._C/C, ........G/G) and six heteroduplexes (FIG. 4B, _._A/T, _..._A/C, ........C/T, _.._A/G, ___G/T, _..._C/G).

In an illustrated example, all heterozygotes can be detected by the effect of the heteroduplexes on the melting curve (FIG. 4). In addition, 4 out of 6 homozygous differences (A vs C, A vs G, C vs T, and G vs T) are very easily distinguished by Tm shifts (FIG. 4, arrows). However, to distinguish A vs T homozygotes or C vs G homozygotes, high resolution melting is often necessary, and in some cases, homozygotes cannot be differentiated even with the high resolution melting currently available. When the frequency of SNPs in the human genome is considered, in 84% of SNPs it is easy to distinguish the homozygotes (A vs C, A vs G, C vs T, and G vs T), while 16% are more difficult (A vs T and C vs G). Indeed, in 4% of cases (one quarter of 16%), stability calculations using nearest neighbor analysis indicates identical stabilities because of symmetry of neighboring bases. Exact frequencies are given in Table 1 where SNPs are classified according to which homoduplexes and heteroduplexes are produced. In the cases where it is difficult to differentiate homozygotes, an unlabeled probe may be preferred for complete, robust genotyping.

TABLE 1[a]

| Class | SNP Heterozygote (frequency)[b] | Homoduplex Matches (# of Tms) | Heteroduplex Mismatches (# of Tms) |
|---|---|---|---|
| 1 | C vs T or G vs A (0.675) | C::G and A::T (2) | C::A and T::G (2 or 1)[c] |
| 2 | C vs A or G vs T (0.169) | C::G and A::T (2) | C::T and A::G (2 or 1)[c] |
| 3 | C vs G (0.086) | C::G (2 or 1)[c] | C::C and G::G (2) |
| 4 | T vs A (0.070) | A::T (2 or 1)[c] | T::T and A::A (2) |

[a]SNP heterozygotes are specified with the alternate bases separated by "vs", for example C vs T indicates that one allele has a C and the other a T at the same position on the same strand. There is no bias for one allele over the other, that is, C vs T is equivalent to T vs C. Base pairing (whether matched or mismatched) is indicated by a double colon and is not directional. That is, C::G indicates a C::G base pair without specifying which base is on which strand.
[b]The human SNP frequencies were taken from the Kwok data set as reported in Venter JC, et al. The sequence of the human genome. Science 2001; 291: 1304-51).
[c]The number of predicted thermodynamic duplexes depends on the nearest neighbor symmetry around the base change. One quarter of time, nearest neighbor symmetry is expected, that is, the position of the base change will be flanked on each side by complementary bases. For example, if a C vs G SNP is flanked by an A and a T on the same strand, nearest neighbor symmetry occurs and only one homoduplex Tm is expected.

Alternatively, in the cases where differentiation of homozygotes is difficult, a sample of a known homozygous genotype may be mixed in roughly equal amounts with the unknown genotype either before or after amplification. The mixture is amplified (if not previously amplified), denatured, and melted. If the genotypes are the same, the melting curve of the mixture will be the same as the melting curve of the known homozygous genotype. If the genotypes are different, heteroduplexes will be produced and identified by an altered shape of the melting curve.

Illustratively, small amplicons or unlabeled probes may be used when genotyping for known sequence variants, while large amplicons may be preferred when scanning for unknown variants. Multiplexing of amplicons may also be used. For example, if a smaller segment within a large amplicon is known to carry a sequence variant of interest, then both the smaller segment and the full-length amplicon can be amplified and melted in one reaction. The melting data from the large amplicon will provide mutation scanning information, while the melting data from the smaller segment may provide genotyping information. Amplification of both the larger and the smaller amplicon can be performed simultaneously, or by a biphasic PCR which amplifies the larger amplicon in the first phase, and the smaller amplicon(s) in the second phase, or vice versa. This biphasic PCR can be achieved by designing the Tm and amount of each of the primers in a way that, by adjusting the annealing temperatures of the two phases, preferential amplification of the different amplicons occur. When the signal from the larger amplicon is expected to overwhelm or mask the signal from the shorter amplicon, this biphasic technique can be used to adjust the final amount of each of the amplicons to circumvent such a problem.

Simultaneous scanning and genotyping can also be performed in a single PCR when one or more unlabeled probes are included. Both the product melting transition and the probe melting transitions are analyzed. Illustratively, the full length PCR product melting transition is first analyzed to detect any heteroduplexes present. Any sequence difference within the amplicon should be detected by this scanning analysis. If a sequence variant is detected by scanning, the melting transition(s) of the unlabeled probe(s) present reveal the genotype for each probe's locus. Because the probes are smaller than the whole PCR product, genotyping with unlabeled probes is more specific than whole amplicon genotyping, and all SNP changes at the probe locus can be genotyped.

EXAMPLE 1

Dye Synthesis

Unsymmetrical cyanine dyes can be prepared by a general method that attaches the benzazolium portion of the molecule to the pyridinium (or quinolinium, pyrimidinium, purinium) portion through one or more "—C(R)=" groups. As described in U.S. Pat. No. 5,436,134 and references cited therein, the number of "—C(R)=" groups is determined by the specific synthetic reagents used in the synthesis. In the synthesis of monomethine dyes ($R^3$=H, n=0) such as dye S5, a combination of reagents is used in which the methine carbon atom results from either A on the benzazolium salt or B on the pyridinium salt being methyl and the other of A or B being a reactive leaving group that is typically methylthio, methylsulfonyl, or chloro, but which can be any leaving group that provides sufficient reactivity to complete the reaction. One possible way to prepare dye S5 and other similar dyes may be as follows:

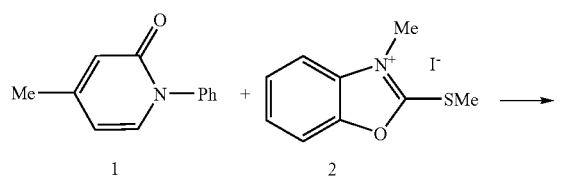

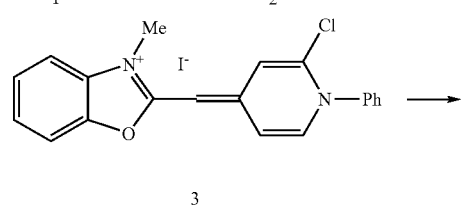

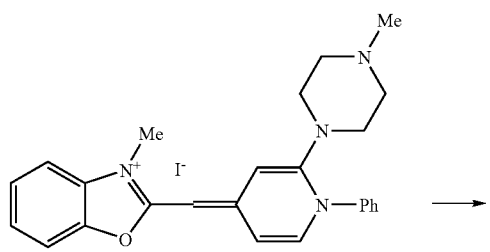

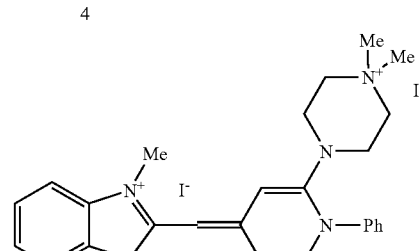

The starting material, Compound 1 is prepared by heating 4-methyl-2-pyridinone (Aldrich) to reflux with copper powder, potassium carbonate and iodobenzene for 48 hours. The reaction is cooled to room temperature, partitioned between water and ethyl acetate, filtered, and the organic layer is dried over magnesium sulfate. The crude product is purified on a silica gel column, eluting with 1:1 ethyl acetate/hexanes to yield Compound 1.

Another starting material, Compound 2, is prepared by adding 2-(methylthio)benzoxazole to methyl iodide in DMF and heating in a sealed tube at 150° C. for one hour to obtain Compound 2, as the iodide salt.

A mixture of Compound 1, phosphorous oxychloride, and a catalytic amount of DMF in methylene chloride is heated to reflux for 24 hours. The mixture is cooled to room temperature and another volume of methylene chloride is added, followed by Compound 2 and one equivalent of triethylamine. The mixture is stirred at room temperature for 6 hours. A solid is separated by filtration and purified using a silica gel column eluting with a mixture of ethyl acetate/chloroform/methanol. The purified compound is then redissolved in methanol and added to an excess of sodium iodide in water. Compound 3 is isolated by filtration as the iodide salt and dried in vacuo.

Compound 3 is then mixed with 1-methylpiperazine in 1,2-dichloroethane and heated at 55° C. for 2 hours. The resulting product (Compound 4) is then quaternized by adding an excess of methyl iodide and Proton Sponge (Aldrich), and is expected to yield dye S5 (Compound 5) as the diiodide salt.

Additionally, certain embodiments of dyes having the following pyrimidinium core structure have been prepared:

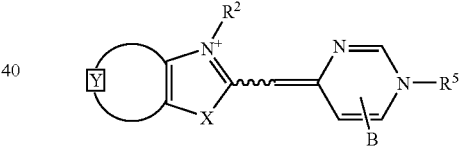

wherein

Y,

X, $R^2$, $R^3$, and $R^5$ are as defined herein for Formula I, and B is as defined in Formulae V.

While there are many ways of preparing dyes having this formula, one method is as follows:

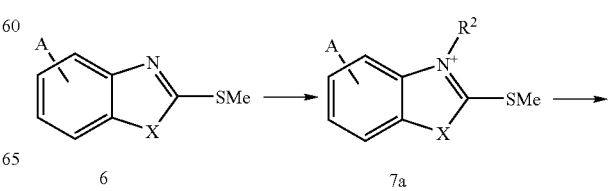

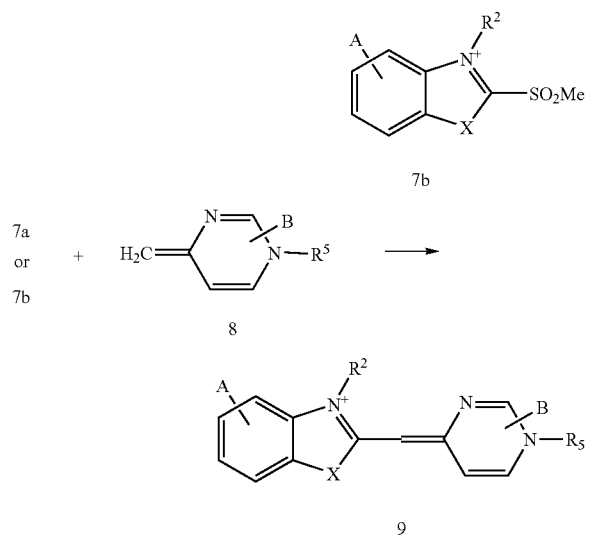

where compounds 6 are commercially available, or may be prepared by conventional methods. Compounds 7a are prepared by alkylation of 6 at N(3) using alkylating agents such as alkyl halides, alkylsulfates, and the like, under neutral or basic conditions, including alkyllithiums, aromatic and aliphatic amines, $K_2CO_3$, and the like. Similarly, compounds 7a are prepared by arylation of 6 at N(3) by aromatic coupling reactions of aromatic halides, boronates, and the like, which are catalyzed by metal compounds, such as copper, palladium, platinum, and like catalysts. Compounds 7b are prepared from compounds 7a by conventional oxidation, such as reactions using hydrogen peroxide, peroxy acids, including m-CPBA, and the like. In some cases, compounds 7a or compounds 7b are commercially available. Compounds 8 are commercially available or are prepared illustratively by condensation of appropriately substituted 1,3-diones and ureas or thioureas. Further, compounds 8 having a thiol, alkoxy, or primary/secondary amine at C(2) may be modified illustratively by reacting with alkylhalides, alkoxyhalides, or any reactant with a good leaving group under neutral conditions. Compounds 9 may be prepared by reacting compounds 7 and compounds 8 under basic conditions, as described herein.

Exemplary compounds having this formula were prepared as herein described, purified by HPLC using triethylamine-ammonium acetate as the mobile phase, and isolated as their corresponding acetate salts. These exemplary compounds are illustrated in Table 2.

TABLE 2

| Dye | Y | X | $R^2$ | $R^5$ | B |
|---|---|---|---|---|---|
| G5 | (phenyl) | S | Ph | $H_2C-CH_2-N^+(Me)_2-CH_2-Me$ | H |
| H5 | $F_2CH-S(O)_2$-phenyl | S | Me | $H_2C-CH_2-N^+(Me)_2-CH_2-Me$ | H |
| I5 | Me-phenyl | S | $H_2C-CH_2-CH_2-SO_3^-$ | $H_2C-CH_2-N^+(Me)_2-CH_2-Me$ | H |
| K5 | Cl-phenyl | S | Me | $H_2C-CH_2-N^+(Me)_2-CH_2-Me$ | H |
| L5 | $O_2N$-phenyl | S | — | $H_2C-CH_2-N^+(Me)_2-CH_2-Me$ | H |
| D6 | (naphthyl) | S | Me | $H_2C-CH_2-N^+(Me)_2-CH_2-Me$ | H |

TABLE 2-continued

| Dye | Y | X | R² | R⁵ | B |
|-----|---|---|----|----|---|
| E6 | phenyl | O | Me | H₂C-CH₂-N⁺(Me)(Me)Me | H |
| P6 | Cl-phenyl | S | H₂C-CH₂-CH₂-SO₃⁻ | H₂C-CH₂-N⁺(Me)(Me)Me | H |
| R6 | Me₃⁺N-phenyl | S | Me | H₂C-CH₂-N⁺(Me)(Me)Me | H |
| Y6 | naphthyl | O | Me | H₂C-CH₂-N⁺(Me)(Me)Me | H |
| Z6 | naphthyl | S | Me | H₂C-CH₂-N⁺(Me)(Me)Me | H |
| F7 | phenyl | S | Me | Ph | 2-[4-(N,N-dimethylpiperazine)]<br>6-Me |
| N7 | phenyl | S | Me | Ph | 2-[S-CH₂CH₂CH₂-N⁺(Me)(Me)Me]<br>6-Me |
| O7 | phenyl | S | Me | Ph | 2-[S—C(O)-4-pyridine)]<br>6-Me |
| P7 | phenyl | S | Me | Ph | 2-[S-(1-bicyclo[2.2.1]heptane)]<br>6-Me |
| Q7 | phenyl | S | Me | Ph | 2-[S-(4-(N-methyl-piperadine))]<br>6-Me |
| R7 | naphthyl | S | Me | Ph | 2-S-CH₂CH₂CH₂-N⁺(Me)(Me)Me<br>6-Me |

TABLE 2-continued
| Dye | Y | X | R² | R⁵ | B |
|---|---|---|---|---|---|
| S7 |  | S | Me | Ph | 2-[S—C(O)-4-pyridine)]<br>6-Me |
| T7 | 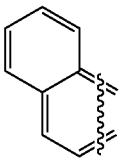 | S | Me | Ph | 2-[S-(C(O)-4-PhNO₂)]<br>6-Me |
| U7 | 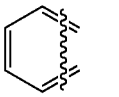 | S | Me | Ph | 2-SMe<br>6-Me |
| V7 | 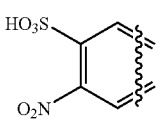 | S | Me | Ph | 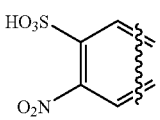 |
| W7 | 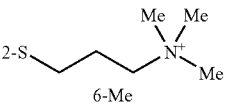 | S | None | Ph | 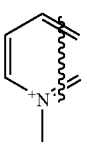 |
| X7 | 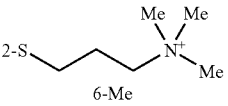 | S | Me | Ph | 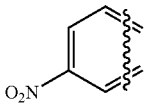 |
| Z7 | 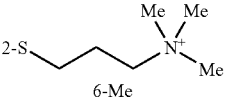 | S | Me | Ph | 2-SCH₃<br>6-Me |
| C8 | 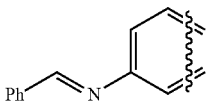 | S | Me | Ph | 2-NH₂<br>6-Me |
| E8 |  | S | Me | Ph | 2-OH<br>6-Me |
| G8 |  | S | Me | Ph | 2-SCH₃<br>6-Me |
| K8 | 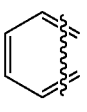 | S | 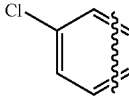 | Ph | 2-SCH₃<br>6-Me |
| L8 | 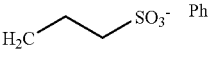 | S | None | Ph | 2-SCH₃<br>6-Me |

TABLE 2-continued

| Dye | Y | X | R² | R⁵ | B |
|---|---|---|---|---|---|
| M8 | phenyl | S | Me | Ph | 2-[S-(2-pyrimidine)]<br>6-Me |
| N8 | phenyl | S | Me | Ph | 2-SMe<br>6-Ph |
| O8 | phenyl | S | Me<br>R³=C(O)Ph | H₂C-CH₂-N⁺(Me)₃ | H |
| P8 | phenyl | S | Me | Ph | 2-S-benzyl<br>6-Me |
| T8 | phenyl | S | Me | Ph | 2-[S—(C(O)—Ph)]<br>6-Me |
| V8 | naphthyl | S | Me | Ph | 2-SCH₃<br>6-Me |
| W8 | phenyl | S | Ph | Ph | 2-SCH₃<br>6-Me |
| X8 | 4-nitrophenyl | S | Me | Ph | 2-SCH₃<br>6-Me |
| Z8 | phenyl | S | Me | 1-Naphthyl | 2-SCH₃<br>6-Me |
| A9 | phenyl | S | Me | Ph | 2-[S-(5'-deoxyAdenosine)]<br>6-Me |
| C9 | 3-phthalimidophenyl | S | Me | Ph | 2-S-CH₂CH₂CH₂-N⁺(Me)₃<br>6-Me |
| G9 | 3-chlorophenyl | S | H₂C-CH₂-SO₃⁻ | Ph | 2-SCH₃<br>6-Me |
| I9 | phenyl | S | Me | Ph | 2-S—C(O)—CH₂—NMe₂<br>6-Me |

TABLE 2-continued

| Dye | Y | X | R² | R⁵ | B |
|---|---|---|---|---|---|
| J9 | benzo | S | Me | Ph | 2-[S—(C(O)-4-(N-methylpiperazine))]<br>6-Me |
| K9 | benzo | S | Me | Ph | 2-[S—C(O)-4-morpholine)]<br>6-Me |
| L9 | benzo | S | Me | Ph | 2-[S—(C(O)-4-(N,N-dimethylaniline))]<br>6-Me |
| M9 | benzo | S | Me | Ph | 2-[S—C(O)-2-pyrazine)]<br>6-Me |
| N9 | benzo | S | Me | Ph | 2-[S—C(O)-6-benzopyrazine)]<br>6-Me |
| O9 | benzo | S | Me | Ph | 2-[S—(C(O)-5-(1-methyl-1,2,3-benzotriazole))]<br>6-Me |
| P9 | benzo | S | Me | Ph | 2-[S—(C(O)—C₆F₅)]<br>6-Me |
| Q9 | N-methyl pyridinium | O | None | Ph | 2-SCH₃<br>6-Me |
| R9 | N-methyl pyridinium | O | None | Ph | 2-S—(CH₂)₃—N⁺(Me)₃<br>6-Me |
| A10 | benzo | S | Me | Ph | 2-(CH₂)₃—N⁺(Me)₃<br>6-Me |

Compound D6 was prepared by first reacting 4-methylpyrimidine with (3-bromopropyl)trimethylammonium bromide in acetonitrile at reflux The resulting product (compound A6) in acetonitrile was reacted with 3-methyl-2-methylsulfonylbenzothiazolium iodide (available from Aldrich) in the presence of anhydrous pyridine and triethylamine, or in chloroform:methanol (10:1) and an excess of triethylamine. The reaction was carried out either at reflux, or at room temperature.

Compound E6 was prepared according to the general procedure used to prepare compound D6 from 3-methyl-2-methylsulfonylbenzoxazolium iodide (prepared by reacting 2-methylsulfonylbenzoxazole with dimethylsulfate) and compound A6.

Compound G5 was prepared according to the general procedure used to prepare compound D6 from 2-methylthio-3-phenylbenzothiazolium (Aldrich) and compound A6.

Compound H5 was prepared according to the general procedure used to prepare compound D6 from 5-difluoromethylsulfonyl-3-methyl-2-methylthiobenzothiazolium methylsulfate (prepared by reacting 5-difluoromethylsulfonyl-2-methylthiobenzothiazole, available from Aldrich, with dimethylsulfate) and compound A6.

Compound P6 was prepared according to the general procedure used to prepare compound D6 from 5-chloro-2-(methylthio)-3-(3-sulfopropyl)-benzothiazolium hydroxide (Aldrich) and compound A6.

Compound R6 was prepared according to the general procedure used to prepare compound D6 from 6-amino-3-methyl-2-methylthiobenzothiazolium methylsulfate (prepared by reacting 6-amino-2-methylthiobenzothiazole, available from Aldrich, with dimethylsulfate) and compound A6.

Compound Y6 was prepared according to the general procedure used to prepare compound D6 from 3-methyl-2-methylsulfonylnaphtho[1,2-d]oxazolium methylsulfate (prepared by reacting 2-methylsulfonylnaphtho[1,2-d]oxazole, available from Chem Bridge Product List, San Diego, Calif., with dimethylsulfate) and compound A6.

Compound Z6 was prepared according to the general procedure used to prepare compound D6 from 3-methyl-2-methylsulfonylnaphtho[1,2-d]thiazolium methylsulfate (prepared by reacting 2-methylsulfonylnaphtho[1,2-d]thiazole, available from Specs, Rijswijk, The Netherlands, with dimethylsulfate) and compound A6.

Compound G8 was prepared by heating a solution of N-phenylthiourea and 2,4-pentanedione in HCl/EtOH at reflux. The resulting pyrimidinthione was reacted with 3-methyl-2-methylsulfonylbenzothiazolium iodide in the presence of triethylamine in chloroform/methanol (10:1) at reflux overnight to give compound G8.

Compounds G5, I5, K5, L5, F7, N7, O7, P7, Q7, R7, S7, T7, U7, V7, W7, X7, Z7, C8, E8, K8, L8, M8, N8, O8, P8, T8, V8, W8, X8, Z8, A9, C9, G9, I9, J9, K9, L9, M9, N9, O9, P9, Q9, R9, and A10 may be prepared by similar methods described above. These dyes are dsDNA binding dyes whose fluorescence changes upon binding to dsDNA. It is expected that many of these dyes would be useful for detection of heteroduplexes.

The pyrimidinium-based cyanine dyes described herein, illustratively G5, H5, I5, K5, L5, D6, E6, P6, R6, Y6, Z6, F7, N7, O7, P7, Q7, R7, S7, T7, U7, V7, W7, X7, Z7, C8, E8, G8, K8, L8, M8, N8, O8, P8, T8, V8, W8, X8, Z8, A9, C9, G9, I9, J9, K9, L9, M9, N9, O9, P9, Q9, R9, and A10 are novel. The results of using some of these dyes in the detection of heteroduplexes are summarized in Table 3. In general, dyes that inhibit PCR at levels below 50% saturation do not detect heterozygotes well. PCR methods and heteroduplex detection are as discussed in the following examples.

TABLE 3

| Dye | Ex/Em[1] | Maximum PCR compatible % Sat[2] | % Het[3] |
| --- | --- | --- | --- |
| G5 | 442-458/475 | 100% | 20.0% |
| H5 | 444/459 | 100% | 22.5% |
| S5 | 450/469 | >99% | 20.5% |
| D6 | 457/471 | 92% | 23.3% |
| E6 | 425/454 | >99% | 15.0% |
| P6 | 464/490 | 100% | 21.0% |
| R6 | 453/470 | >90% | 15.0% |
| Y6 | 439/477-515 | 100% | 21.0% |
| Z6 | 469/494-526 | 100% | 13.4% |
| N7 | 458/474 | >100% | 22.0% |
| O7 | ***[4] | >70% | 21.2% |
| P7 | ***[4] | >70% | 21.5% |
| Q7 | 453/471 | >70% | 20.7% |
| T7 | 453/471 | >70% | 21.2% |
| G8 | 453/471 | >100% | 19.7% |
| L8 | 470-490/490-520 | >70% | 2.3% |
| P8 | 453/471 | >70% | 17.7% |

TABLE 3-continued

| Dye | Ex/Em[1] | Maximum PCR compatible % Sat[2] | % Het[3] |
| --- | --- | --- | --- |
| T8 | 453/471 | >70% | 24.0% |
| V8 | 469/494-526 | >70% | 21.4% |
| W8 | 453/471 | >70% | 27.5% |
| Z8 | 453/471 | >70% | 22.7% |
| A9 | ***[4] | 100% | 23.0% |
| I9 | ***[4] | 100% | 20.9% |
| J9 | ***[4] | 100% | 22.4% |
| K9 | ***[4] | 100% | 22.3% |
| L9 | ***[4] | 100% | 21.3% |

[1]Excitation maxima (Ex) and emission maxima (Em) obtained in a fluorimeter using 2.5 μM bp (100 ng/60 μl)of dsDNA and dye at maximum PCR compatible concentration in PCR buffer (3 mM MgCl$_2$, 50 mM Tris, pH 8.3, 200 μM each dNTP, 500 μg/ml BSA). Some dyes have a range due to the broad emission or excitation peak.
[2]Maximum amount of dye that can be present in a PCR mixture that allows amplification without significant inhibition, expressed as percentage of fluorescence compared to fluorescence of the same dye at saturating concentration, i.e. the concentration that provides the highest fluorescence intensity possible, all in the presence of 15 μM bp DNA (100 ng dsDNA/10 μl) and PCR buffer.
[3]Percentage peak area of the heteroduplex signature peak as measured with 420-490 nm excitation and 450-530 nm detection optics, using the del F508 heterozygote melting curve obtained at a heating ramp of 0.3° C./s. The amplicon used in this set of experiments were 57 bp long generated by primers GGCACCATTAAAGAAAATAT (SEQ ID NO. 1) and TCTGTATCTATATTCATCATAGG (SEQ ID NO. 24) Maximum % obtained was recorded.
[4]Spectral data not available.

EXAMPLE 2

PCR Protocol

Labeled and unlabeled oligonucleotides were obtained from IT Biochem (Salt Lake City, Utah), Qiagen Operon (Alameda, Calif.), or Synthegen (Houston, Tex.). PCR was performed in 10 μl volumes in a LightCycler® (Roche Applied Systems, Indianapolis, Ind.) with programmed transitions of 20° C./s unless otherwise indicated. The amplification mixture included 50 ng of genomic DNA as template, 200 μM of each dNTP, 3 mM MgCl$_2$, 100 mM 2-amino-2-methyl-1,3-propanediol, pH 8.8, 0.04 U/μl Taq polymerase (Roche), 500 μg/ml bovine serum albumin, and 0.5 μM of each primer unless indicated otherwise. Genotyped human genomic DNA was obtained from prior studies (Gundry CN, et al., Genetic Testing, 1999;3:365-70; Herrmann M, et al., Clin Chem 2000;46:425-8) or from Coriell Cell Repositories (Camden, N.J.). Dye S5 was included in the PCR reaction at 10 μM unless otherwise indicated. When SYBR® Green I was used as the indicator, a 1:10,000 final dilution from the Molecular Probes stock was used. The dye is added before PCR, amplification performed, and the melting transition of the amplicon is monitored on the LightCycler® or by high resolution melting analysis. Different homozygotes are distinguished by amplicon melting temperature (Tm). Heterozygotes are identified by low temperature melting of heteroduplexes that broaden the overall melting transition. Melting analysis requires about 1 min and no sample processing is needed after PCR.

To study the sensitivity of dye S5, SYBR® Green I, and other dsDNA binding dyes, polymorphisms in Factor V Leiden, cystic fibrosis (F508del, F508C, I507del, I506V), and HTR2A (T102C) genes were analyzed. In addition, engineered plasmids were used to systematically study all possible single base changes. Heteroduplexes produced by amplification of heterozygous DNA were best detected by rapid cooling (at least −2° C./s) of denatured products, followed by rapid heating during melting analysis (0.2 to 0.4° C./s). All heterozygotes were distinguished from homozygotes by a broader melting transition. Different homozygotes could often be distinguished by their Tm. Homozygous G to C base changes could not reproducibly be distinguished, even with high resolution analysis, without mixing homozygotes. The amplicons varied in length from 44 to 331 bp.

While the dyes S5, D6, Z6 and N7 are used in the Examples provided herein, it is understood that other dyes according to this invention may be used.

EXAMPLE 3

Melting Curve Analysis

Melting analysis was performed on the LightCycler® immediately after cycling, or subsequently on either the high-resolution melting instrument HR-1 (Idaho Technology, Salt Lake City, Utah) or the LightTyper® (Roche Applied Systems, Indianapolis, Ind.). However, it is understood that melting curve analysis may be performed in the absence of amplification. When the LightCycler® was used, the samples were first heated to 94° C., cooled to 60° C. at a program setting of −20° C./s, then melted at 0.2° C./s with continuous acquisition of fluorescence. For melting in one of the other instruments, the samples were first amplified in the LightCycler®, then heated momentarily in the LightCycler® to 94° C. and rapidly cooled (program setting of −20° C./s) to 40° C., unless stated otherwise. The LightCycler® capillaries were then transferred one at a time to the high-resolution instrument and heated at 0.3° C./s unless otherwise stated. The HR-1 is a single sample instrument that surrounds one LightCycler® capillary with an aluminum cylinder. The system is heated by Joule heating through a coil wound around the outside of the cylinder. Sample temperature is monitored with a thermocouple also placed within the cylinder and converted to a 24-bit digital signal. Fluorescence is monitored by epi-illumination of the capillary tip (Wittwer C T, et al., BioTechniques 1997;22: 176-81) that is positioned at the bottom of the cylinder and also converted to a 24-bit signal (it is noted that some of the examples used an earlier 16-bit HR-1 prototype). Approximately 50 data points are acquired for every ° C. Standard optics were used on all instruments unless otherwise noted.

In some cases it is advantageous not to denature the product after PCR before melting curve acquisition. For example, when the goal is to type the number of repeat sequences (e.g. STRs, VNTRs), amplification may be stopped at the extension step during the exponential phase of the reaction before plateau, and then melting analysis is performed. This way, homoduplex extension products can be analyzed. In repeat typing, homoduplex products can be more informative than heteroduplex products, especially since many different heteroduplex products may form from different alignment of the repeats. In some cases, it may be helpful to obtain both a homoduplex melting curve (without prior denaturation) and a heteroduplex melting curve (with denaturation and the formation of all possible duplex combinations). The difference between these two melting curves gives a measure of the extent of heteroduplexes that can be formed, using the same sample as the "homoduplex control".

Melting data were analyzed with custom software written in LabView. Fluorescence vs temperature plots were normalized between 0 and 100 percent by first defining linear baselines before and after the melting transition of each sample. Within each sample, the fluorescence of each acquisition was calculated as the percent fluorescence between the top and bottom baselines at the acquisition temperature. In some cases, derivative melting curve plots were calculated from the Savitsky-Golay polynomials at each point (Press W H, et al., eds. Numerical recipes in C, $2^{nd}$ ed. New York: Cambridge University Press, 1992:650-5). Savitsky-Golay analysis used a second-degree polynomial and a data window including all points within a 1° C. interval. Peak areas and melting temperatures were obtained by using non-linear least squares regression to fit multiple Gaussians. In some cases, the X-axis for each normalized melting curve was translated so that the tracings overlapped within a certain fluorescence range. This "temperature shifting" corrects for any minor inter-run temperature variation and increases the ability to distinguish heterozygotes from homozygotes. The difference between genotypes can also be magnified by plotting the fluorescence difference between genotypes at each temperature.

EXAMPLE 4

Single Nucleotide Polymorphism Genotyping with Dye S5: Genotyping the Factor V Leiden Mutation A 43 bp amplicon was formed from primers 18 and 24 bases in length, immediately flanking the location of the factor V Leiden mutation. Both primers had an estimated Tm of 62° C. The samples were cycled 35 times with the following protocol: 94° C. with no hold, 60° C. with no hold, and 72° C. with a 10 s hold. After amplification, the samples were heated momentarily in the LightCycler® to 94° C., cooled rapidly (program setting of −20° C./s) to 60° C., and PCR products melted at 0.2° C./s with continuous fluorescence acquisition.

Figure 1:
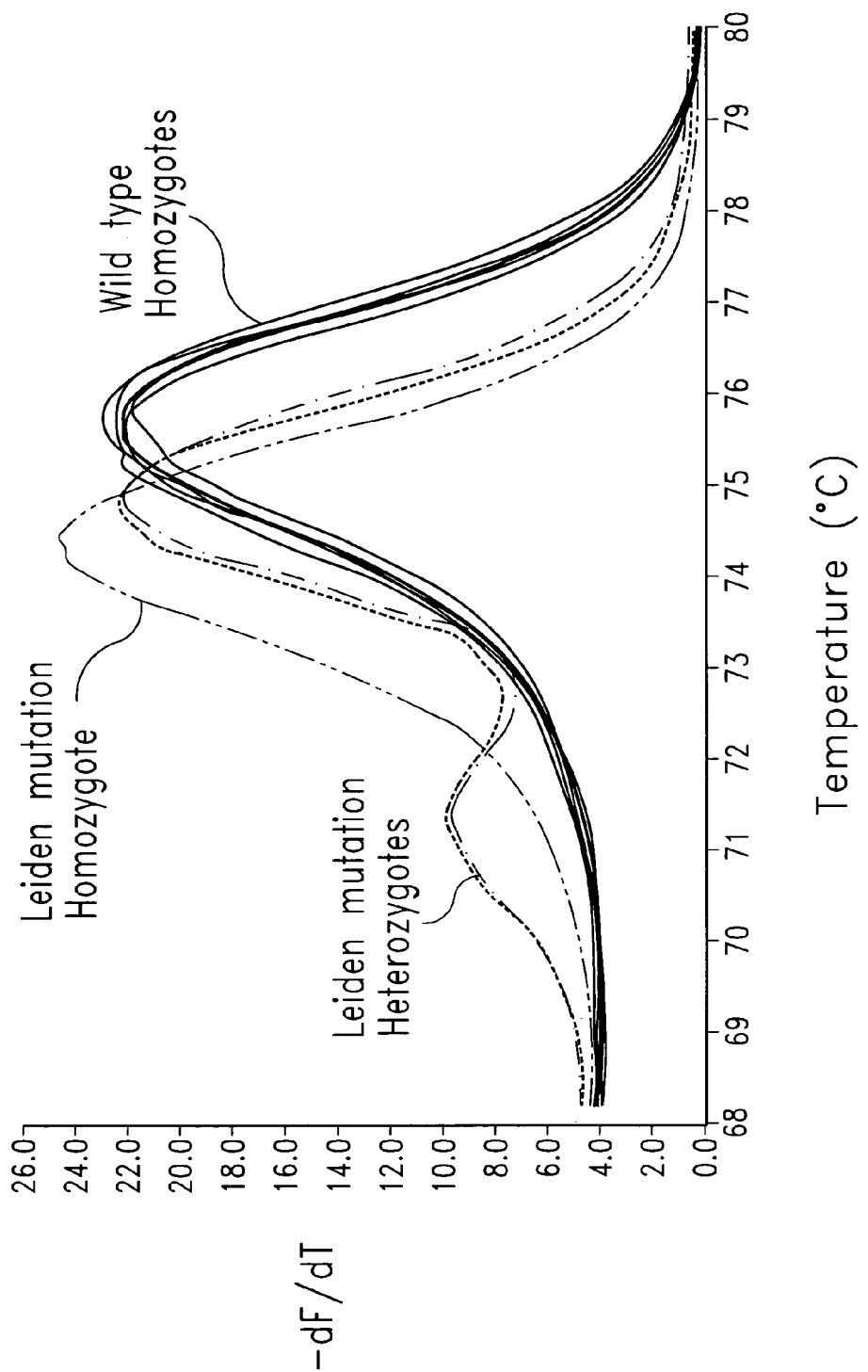
FIG. 1 shows genotyping of the Factor V Leiden using dye S5. The negative first derivative (−dF/dT) of the melting curve is shown.

Derivative melting curves of PCR products amplified from different genotypes at the Leiden locus of the factor V gene are shown in FIG. 1. Dye S5 was used for fluorescent monitoring of the melting transition between double- and single-stranded products. The Leiden mutation is located 19 bases from one end of the amplicon. Results from ten homozygous wild type, two heterozygous, and one homozygous Leiden genotypes are shown. The amplicon melting temperature of the homozygous mutant is about 1° C. less than the homozygous wild type melting temperature. Heterozygous samples show a secondary, low temperature melting transition attributable to heteroduplex formation. A similar experiment using SYBR® Green I failed to detect this secondary melting transition in heterozygotes (data not shown).

The effects of cooling rate and heating rate were studied using heterozygous factor V Leiden DNA on the LightCycler®. To study the effect of cooling rate, the samples were amplified as above, heated to 85° C., and then cooled from 85° C. to 60° C. at rate of −20, −2, −1, −0.5, or −0.1° C./s, followed by a constant heating rate of 0.2° C./s for melting curve acquisition. Rapid cooling was necessary for significant heteroduplex formation (FIG. 2). Heteroduplexes were not observed when the cooling rate was −0.1° C./s or slower. The greatest heteroduplex formation occurred when capillary samples were rapidly transferred from boiling water to ice water (data not shown). With cooling on the LightCycler®, heteroduplex formation appeared to plateau at programmed rates faster than −5° C./s (FIG. 2). However, measurement of actual sample temperatures showed that the cooling rate increased only slightly with programmed rates faster than −5° C./s: when the instrument was programmed to cool at −20° C./s, the actual rate was about −6° C./s.

Figure 3:
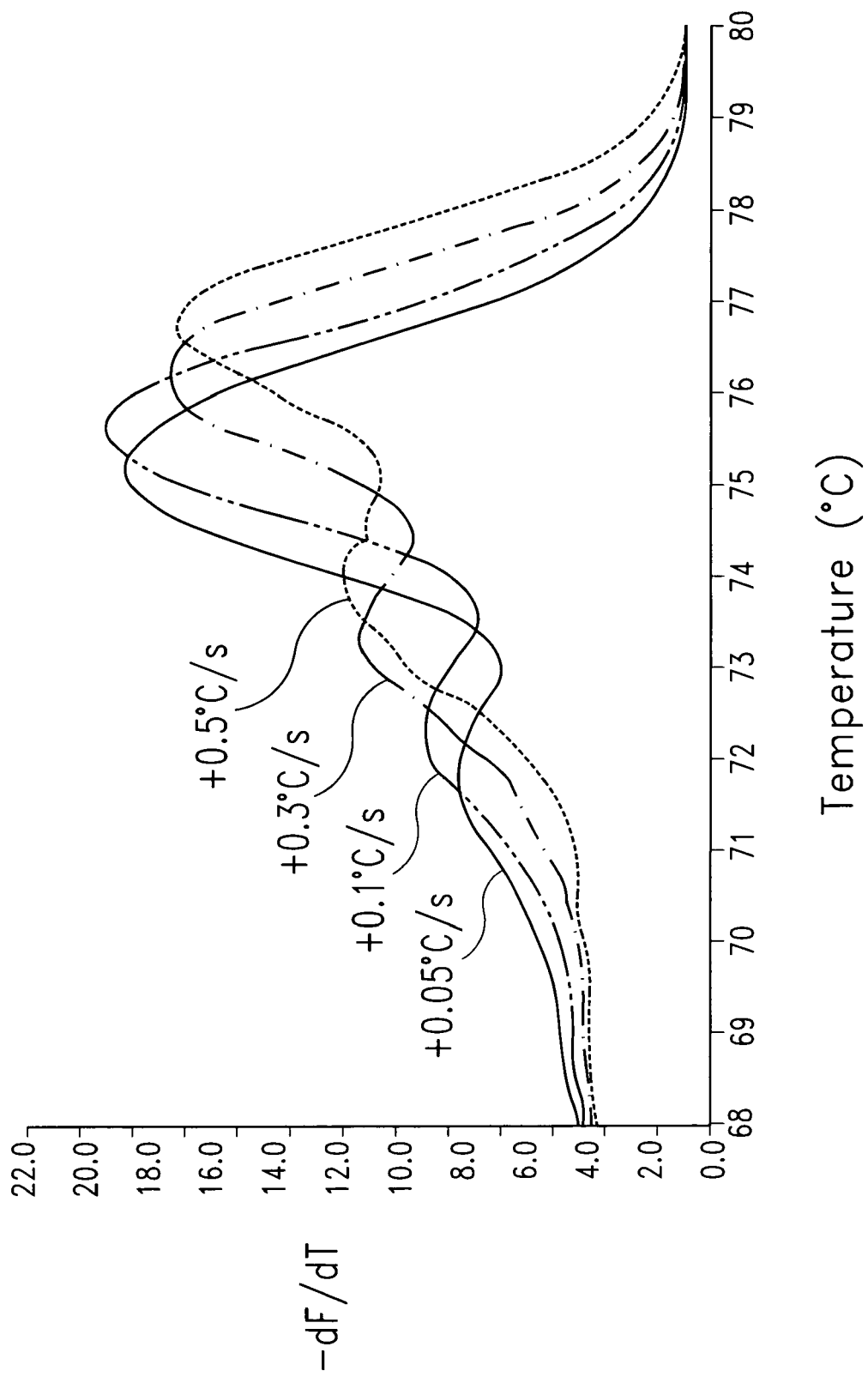
FIG. 3 shows the effect of heating rates during melting analysis on the detection of heteroduplexes.

The effect of heating rate was studied by cooling at a programmed rate of −20° C./s, followed by melting at 0.05, 0.1, 0.3, or 0.5° C./s. The relative percentage of observed heteroduplexes was greater with higher heating rates (FIG. 3). The apparent Tm also shifts to higher temperatures as the rate increases and the melting process deviates more from equilibrium (Gundry C N, et al., Genetic Testing, 1999;3: 365-70).

EXAMPLE 5

Systematic Study of SNP Genotyping with Plasmids

Engineered plasmids were used for systematic study of melting curve genotyping of all possible single base changes. The plasmids (DNA Toolbox, Cambrex Bio Science Rockland Inc.) contained either A, C, G, or T at a defined position amid 50% GC content (Highsmith W E, et al., Electrophoresis 1999;20:1186-94). The four plasmids were either used alone to simulate homozygous genotypes, or in binary combinations to construct "heterozygotes". Primers were TCTGCTCTGCGGCTTTCT (SEQ ID NO. 50) and CGAAGCAGTAAAAGCTCTTGGAT (SEQ ID NO. 51) and produced a 50 bp amplicon around the polymorphic position. The DNA templates were used at $10^6$ copies and PCR was performed with 35 cycles of 85° C. with no hold and 55° C. for 1 sec in the presence of 20 uM D6. The HR-1 high-resolution melting instrument was used for melting analysis.

Figure 4B:
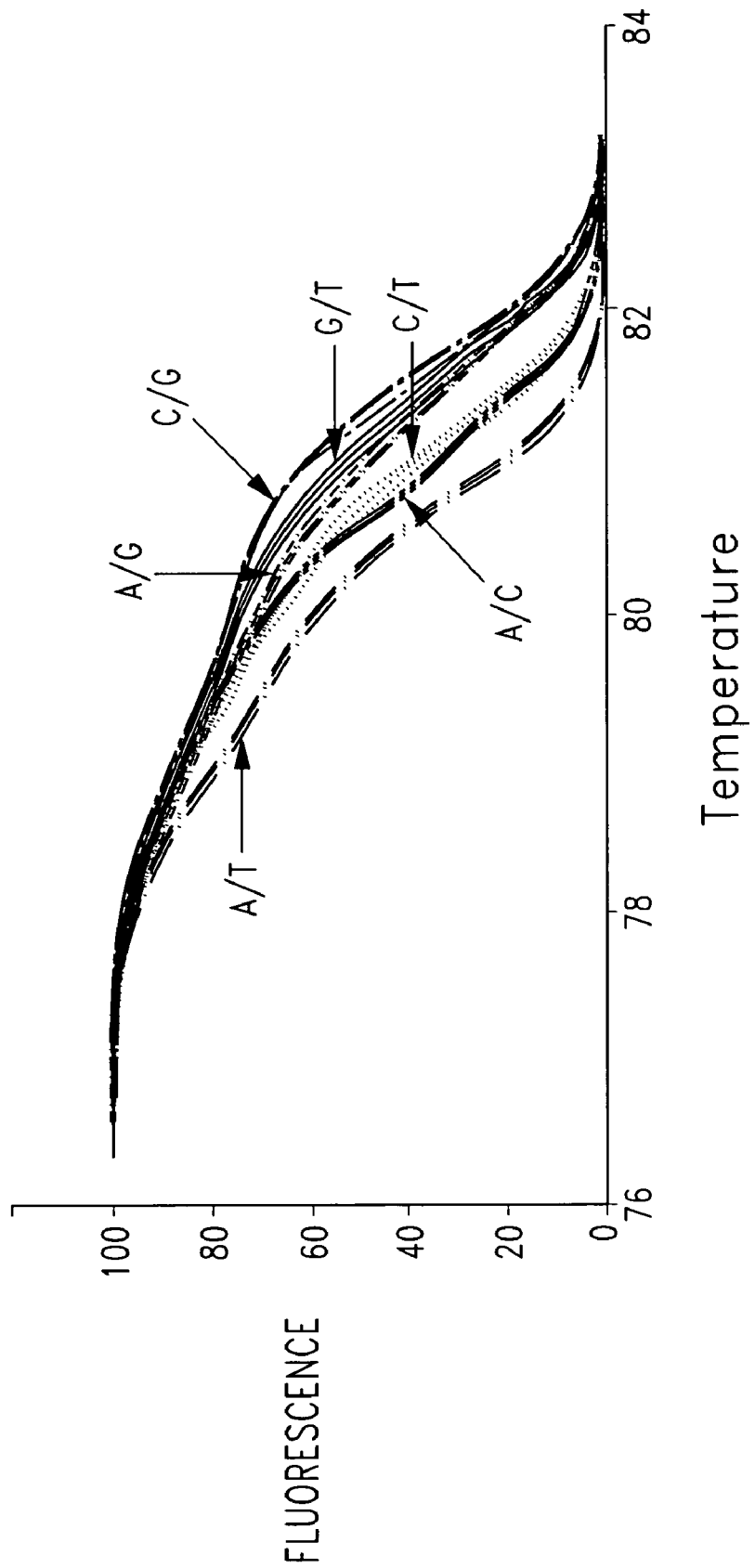

The normalized melting curves of the four homozygotes (FIG. 4A) and six heterozygotes (FIG. 4B) are shown. It is easy to distinguish the homozygotes from the heterozygotes, because the heterozygotes have an extended melting transition that arises from the presence of heteroduplexes. All homozygotes melt in a single transition (FIG. 4A) and the order of melting is correctly predicted by nearest neighbor calculations as A/A<T/T<C/C<G/G (SantaLucia J., Jr, Biochemistry 1996;35:3555-62). Heterozygotes result in more complex melting curves arising from contributions of two homoduplexes and two heteroduplexes (FIG. 4B). Each heterozygote traces a unique melting curve path according to the four duplex Tms. The order of melting is again according to nearest neighbor calculations (A/T<A/C<C/T<A/G<G/T<C/G) using the average of the two homoduplex Tms. The six heterozygote curves merge at high temperatures into three traces, predicted by the highest melting homoduplex present (T/T for the A/T heterozygote, C/C for the A/C and C/T heterozygotes, and G/G for the A/G, G/T, and C/G heterozygotes). All genotypes can be distinguished from each other with high-resolution melting analysis.

EXAMPLE 6

Genotyping of the Cystic Fibrosis Gene with Labeled Primers: Dye S5 or SYBR® Green I KlenTaq1 polymerase (0.04 U/μl, AB Peptides, St. Louis, Mo.), 88 ng of TaqStart antibody (ClonTech, Palo Alto, Calif.), and 50 mM Tris, pH 8.3 were used in PCR instead of Taq polymerase and 2-amino-2-methyl-1,3-propanediol. A 44 bp fragment was amplified with the primers GGCAC-CATTAAAGAAAATAT (SEQ ID NO. 1) and TCATCAT-AGGAAACACCA (SEQ ID NO. 2). The first primer was either 5'-labeled with Oregon Green, or the reaction was performed in the presence of SYBR® Green I or S5. The primers flank the mutational hot spot containing the F508del, I507del, and F508C variants. PCR was performed through 40 cycles of 85° C. and 58° C. (0 s holds). Six samples were monitored during melting curve acquisition on the LightCycler®.

Figure 5B:
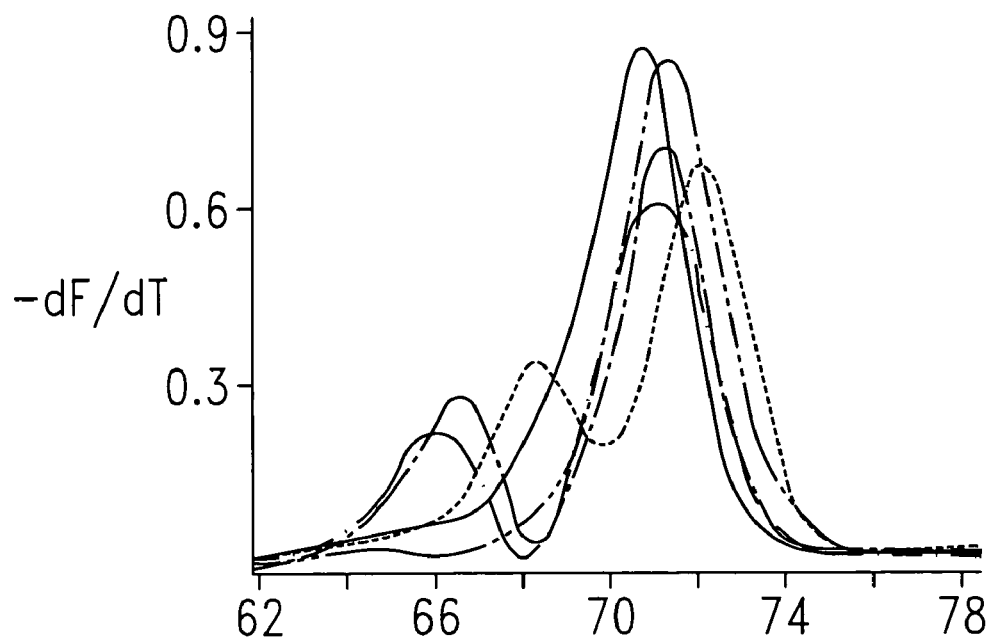
Figure 5C:
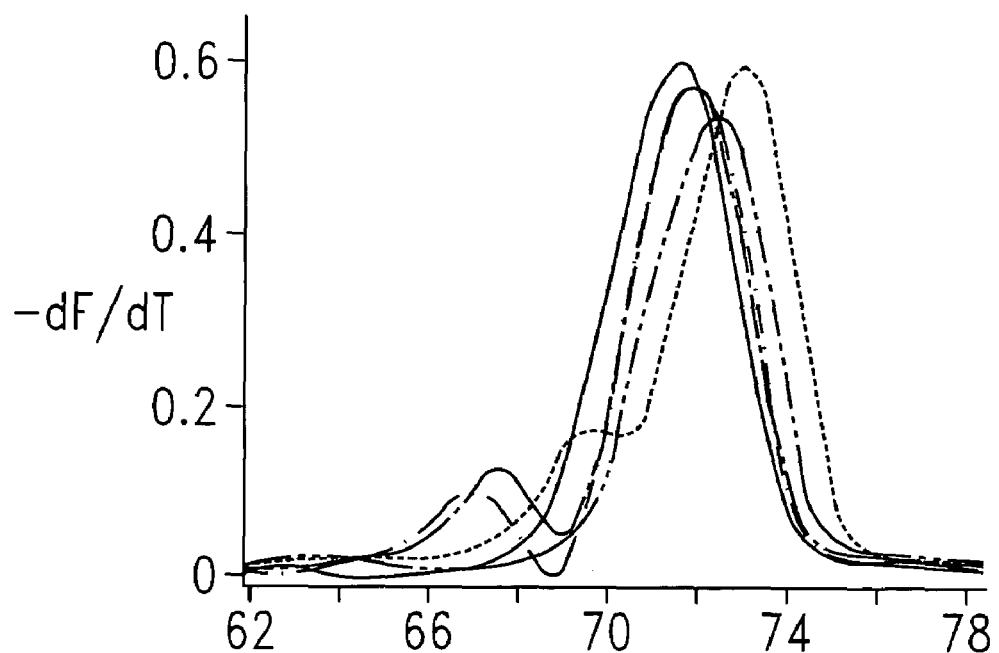
Figure 5D:
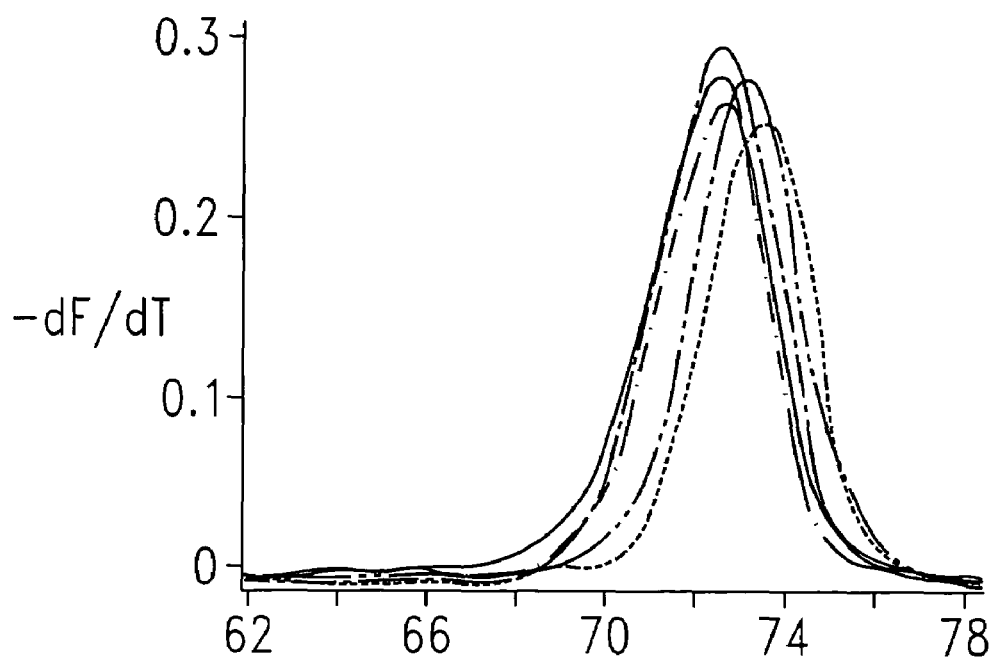

Derivative melting curves of PCR products amplified from different genotypes at the I507/F508 region of the cystic fibrosis gene are shown in FIGS. 5B-D. The PCR products were 41 or 44 bases long (FIG. 5A). Either a 5'-labeled primer (FIG. 5B), dye S5 (FIG. 5C), or SYBR® Green I (FIG. 5D) was used for fluorescent monitoring of the melting transition between double and single stranded products. Results from two homozygous and three heterozygous genotypes are shown.

The duplex stability of the different genotypes follows theoretical calculations (von Ahsen N, et al., Clin Chem 2001;47:1956-61), with F508del ~I507del<Wild type<F508C. Except for F508del and I507del, the genotypes are distinguishable by the Tms of their major transitions. The standard deviation of the Tm of 10 replicate wild type samples was 0.12° C. when melted on the LightCycler®. When melted on the high-resolution instrument, the standard deviation of the Tm of the same 10 samples was 0.04° C.

When a heterozygous sample is amplified by PCR, two homoduplex and two heteroduplex products are expected (Nataraj A J, et al., Electrophoresis 1999;20:1177-85). However, when SYBR® Green I was used as the fluorescent indicator, only a single melting peak was apparent for each genotype (FIG. 5D). In contrast, when labeled primers or dye S5 are used under the same conditions, two clearly defined peaks appeared (FIGS. 5B and 5C). The lower temperature peak is always smaller than the higher temperature peak, and presumably indicates the melting transition of one or both heteroduplex products. As might be expected, the heterozygotes with 3 bp deleted (F508del and I507del) resulted in heteroduplex peaks that were more destabilized than heteroduplex peaks from a single base change (F508C). The primary peak from the F508C heterozygote was at a higher temperature than wild type, reflecting the greater stability of the T to G transversion (Gundry C N, et al., Genetic Testing, 1999;3:365-70).

EXAMPLE 7

Mutation Scanning with Saturation Dyes

The HTR2A single nucleotide polymorphism was studied. The PCR was performed with KlenTaq, TaqStart, and Tris as described for the cystic fibrosis locus. A 331 bp fragment of the hydroxytryptamine receptor 2A (HTR2A) gene included the common polymorphism (T102C) within exon 1 (Lipsky R H, et al., Clin Chem 2001;47:635-44). The reaction was cycled 40 times between 95° C. with no hold, 62° C. with a 2 s hold, and 74° C. with a 20 s hold. A high-resolution melting curve was obtained.

Figure 6:
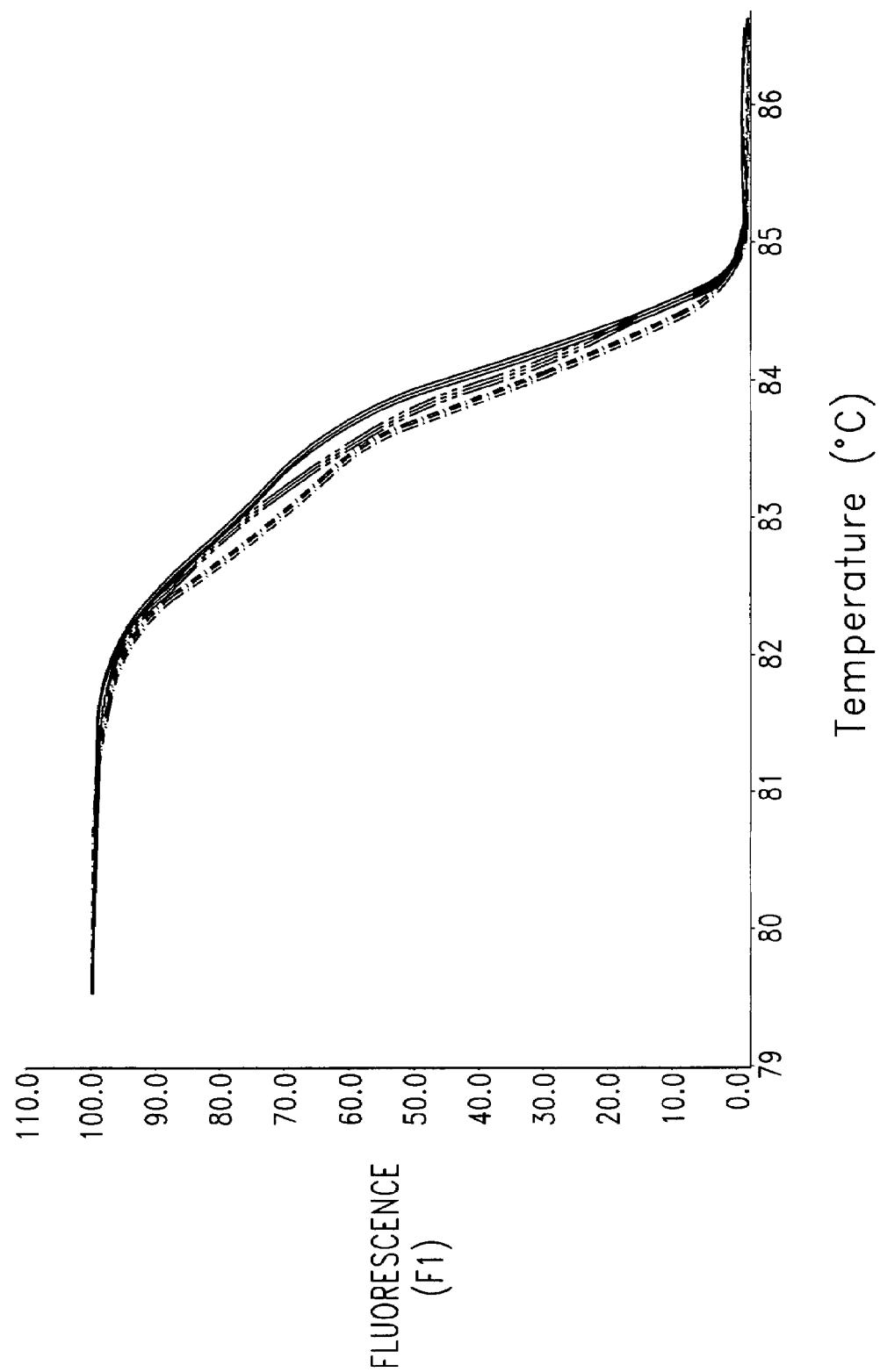
FIG. 6 shows genotyping using dye S5 on longer amplicons (_..._homozygote (TT), ___homozygote (CC), _.._heterozygote (TC)). The melting curves for three individuals (not the derivatives) are shown.

FIG. 6 demonstrates that the saturation dye S5 can be used to scan for sequence variants. That is, the location of the sequence variant need not be known. The presence of any variant can be detected within a large amplicon. As seen in FIG. 6, all three genotypes of the single nucleotide polymorphism in the HTR2A gene (homozygous T, homozygous C and heterozygous T/C) can be differentiated within a 331 bp amplicon. Melting curve precision and the ability to distinguish different genotypes depends on the temperature and fluorescence resolution of the instrument.

EXAMPLE 8

Melting Curve Analysis of a DNA Size Ladder: Comparison of SYBR® Green I to Dye S5

One hundred ng of a DNA size ladder (Low Mass DNA Ladder, Gibco BRL) having six distinct dsDNA species was mixed with either SYBR® Green I (1:10,000) or dye S5 (10 μM) in 3 mM MgCl$_2$, 100 mM 2-amino-2-methyl-1,3-propanediol, pH 8.7 buffer. A melting curve was obtained on the high-resolution instrument at 0.1° C./s.

As discussed above, dye S5, unlike SYBR® Green I, can identify heteroduplexes in melting curve transitions at concentrations compatible with PCR. One reason why SYBR® Green I cannot easily identify low melting transitions is illustrated in FIG. 7. When several DNA fragments of increasing stability are present, the low temperature peaks are very small with SYBR® Green I as compared to dye S5. One explanation is that during melting, SYBR® Green I may be released from low temperature duplexes, only to attach to duplexes that melt at higher temperatures. This causes each successive peak to be higher than the last, with the lowest temperature peaks being very small, if observable at all. Dye S5, which is present at a much higher saturation level, has visible peaks for even low temperature duplexes. While dye S5 was present at near saturation levels in this example, surprisingly, S5 can detect the low temperature peaks when diluted to saturation levels of 5-20%. For example, the data illustrated in FIG. 13 were obtained using an S5 concentration of 1 μM. Thus, while the mechanism is not understood, dye S5 and various other saturating dyes of this invention do not appear to redistribute during melting.

Figure 8:
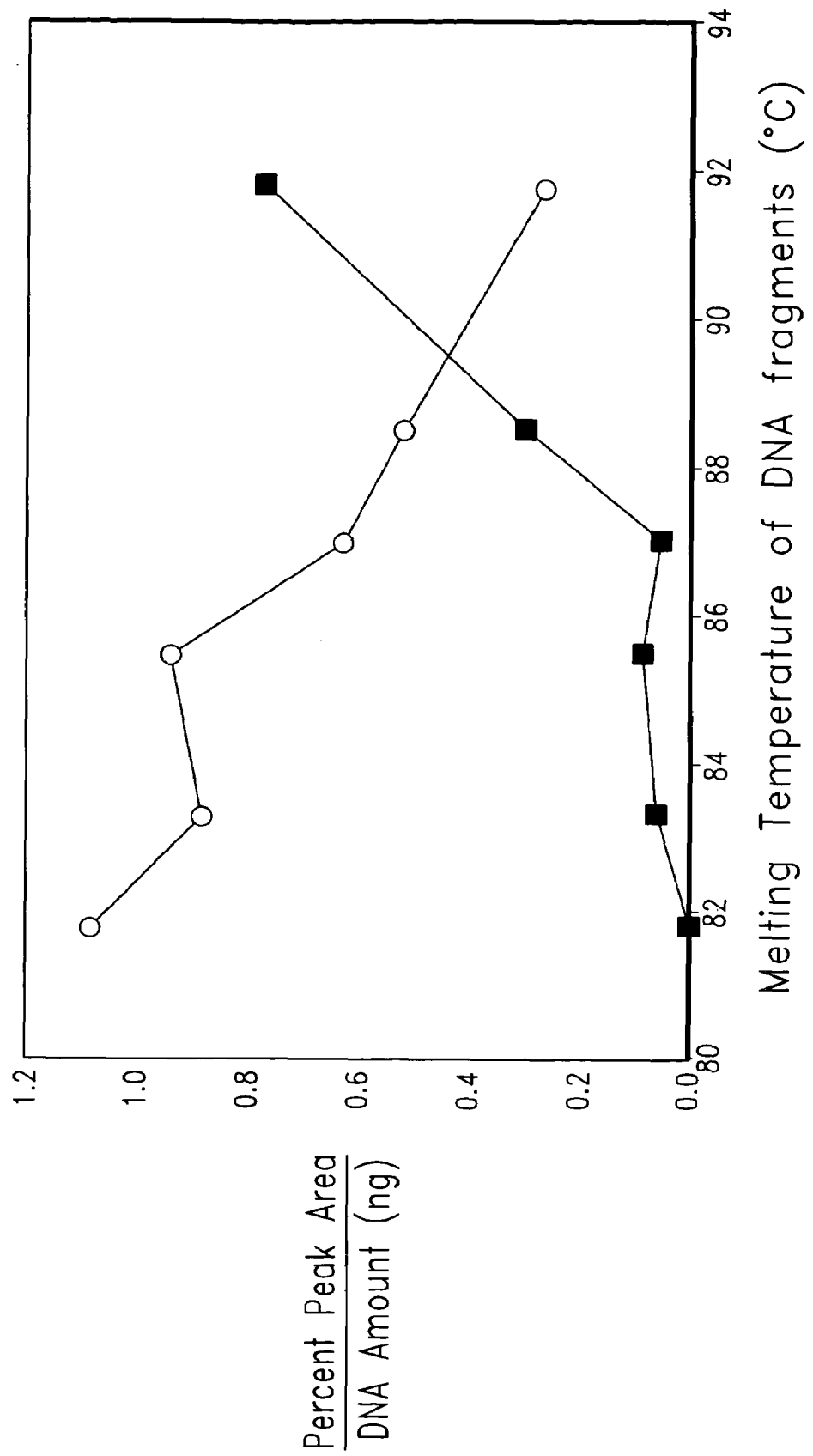
FIG. 8 demonstrates the non-linearity of fluorescence change when multiple DNA species are present. Dye S5 (open circles) and SYBR® Green I (closed squares) are shown.

If the areas of each peak in FIG. 7 are determined and divided by the known amount of each of the DNA species, the relative sensitivity for each DNA species can be assessed (FIG. 8). As shown in FIG. 8, with dye S5, low temperature melting peaks are favored, whereas with SYBR® Green I, a large enhancement of signal is observed at high temperature.

EXAMPLE 9

Titration Curves of Common dsDNA Dyes And determination of Useful Concentration Range of Dye S5 in PCR One hundred ng of the low mass DNA ladder was mixed with different concentrations of common dsDNA dyes in the presence of 3 mM MgCl$_2$, 50 mM Tris, pH 8.3, 250 μg/ml BSA and 200 μM each dNTP in a final volume of 10 μl. The samples were transferred to LightCycler® tubes and the fluorescence measured at 40° C. on the real-time fluorimeter. The fluorescence was normalized to the maximum fluorescence obtained with each particular dye.

Dilution studies were done using a 152 bp HTR2A amplicon in 10 μl volumes with 3 mM Mg$^{2+}$, 50 mM Tris-HCl, pH=8.3, 500 μg/ml BSA, 200 μM each dNTP, 0.5 μM of each primer, 50 ng genomic DNA, 0.4 U of Taq Polymerase, and 88 ng of TaqStart antibody, with S5 dilutions ranging from 2 μM to 100 μM. After an initial denaturation for 10 s at 95° C., 40 cycles of 95° C. for 0 sec, 62° C. for 2 sec, and 72° C. for 20 sec were performed. After additional temperature conditioning on the LightCycler® (95° C. for 0 s, 55° C. for 0 s) the samples were melted on the high-resolution instrument with a slope of 0.3° C./sec.

Figure 9A:
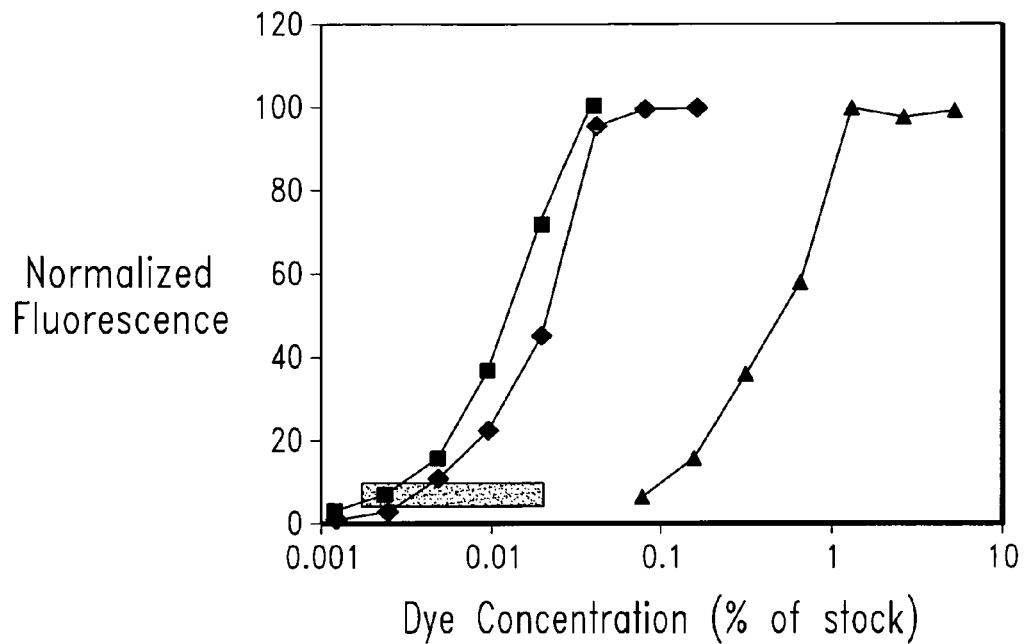
FIGS. 9A-B show dye titrations to determine saturation percentages, in FIG. 9A, ♦-SYBR® Green, ■-SYBR® Gold, ▲-Pico Green, in FIG. 9B, ○-dye S5, ■-SYTOX® Green. Illustrative PCR ranges for SYBR® Green I and dye S5 are indicated by the shaded box.
Figure 9B:
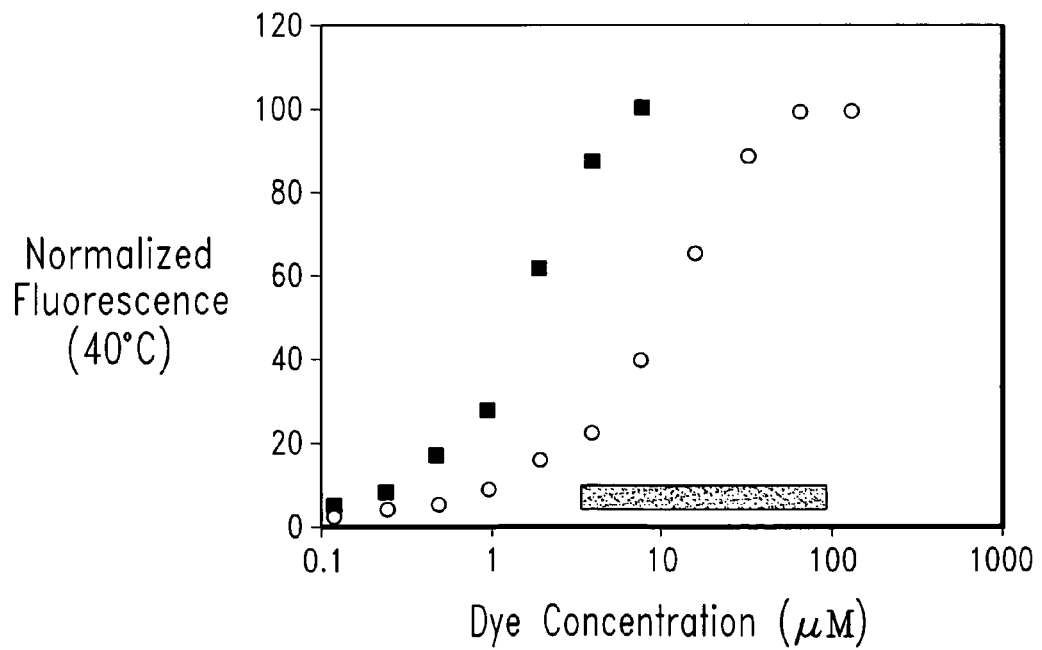
Figure 10:
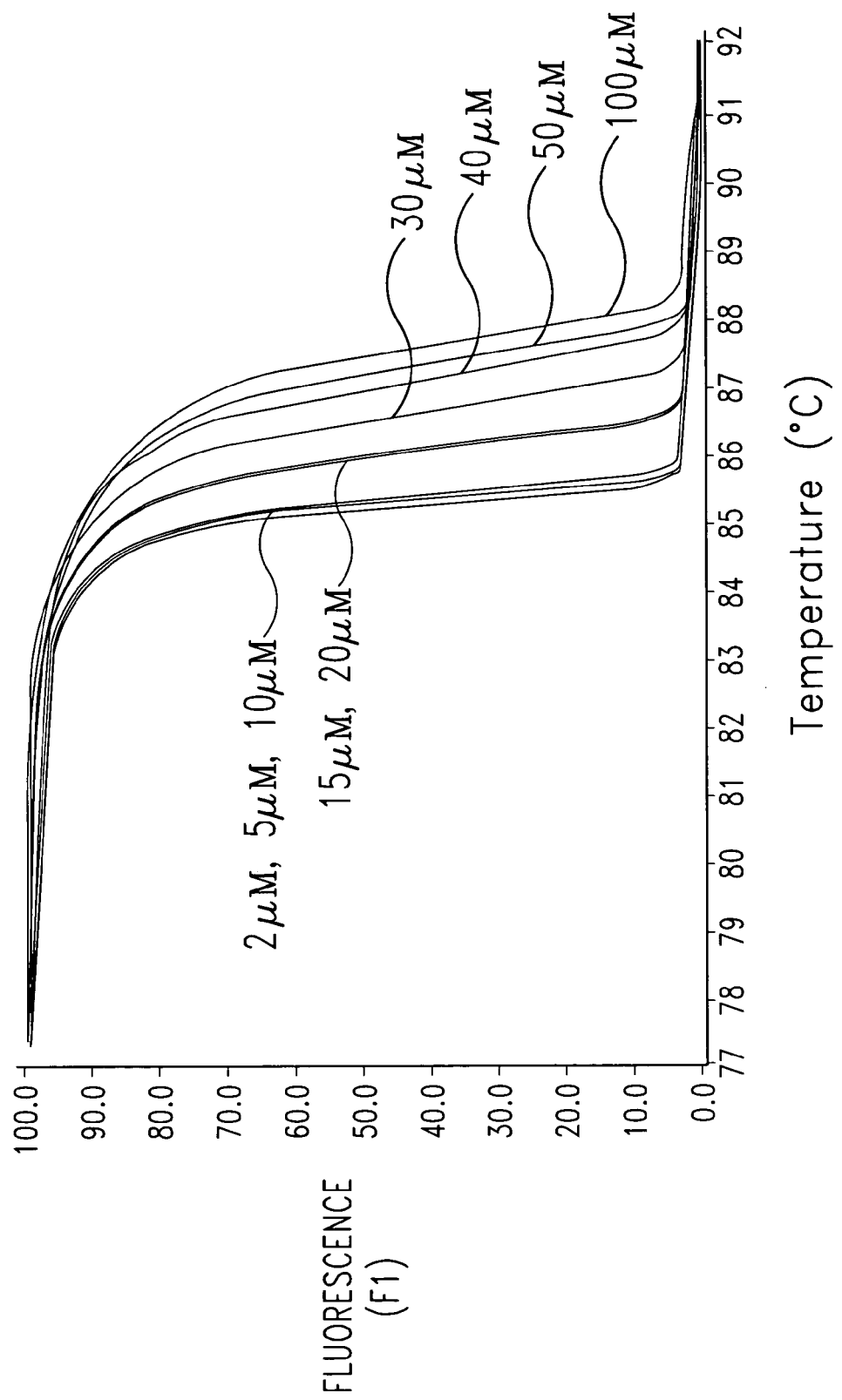
FIG. 10 illustrates the effect of dye concentrations on melting temperature.

FIGS. 9A-B show the concentrations of SYBR® Green I and dye S5 that are compatible with PCR. At concentrations compatible with PCR, SYBR® Green I is far from saturating the amount of DNA typically present at the end of PCR. Dye S5, in contrast, can be used over a wide range of concentrations, including those that are saturating. Typical melting curves over a 50-fold range of dye S5 concentration are shown in FIG. 10.

EXAMPLE 10

Fluorescence Spectra of SYBR® Green I and Dye S5

The excitation and emission spectra of SYBR® Green I and dye S5 bound to DNA were measured on a Photon Technology fluorimeter (FL-1). Dye S5 (10 μM) or SYBR® Green I (1:10,000) was added to 100 ng DNA (Low Mass DNA Ladder) in the presence of 3 mM MgCl$_2$, 50 mM Tris, pH 8.3, 250 μg/ml BSA and 200 μM each dNTP in a final volume of 60 μl.

Figure 11A:
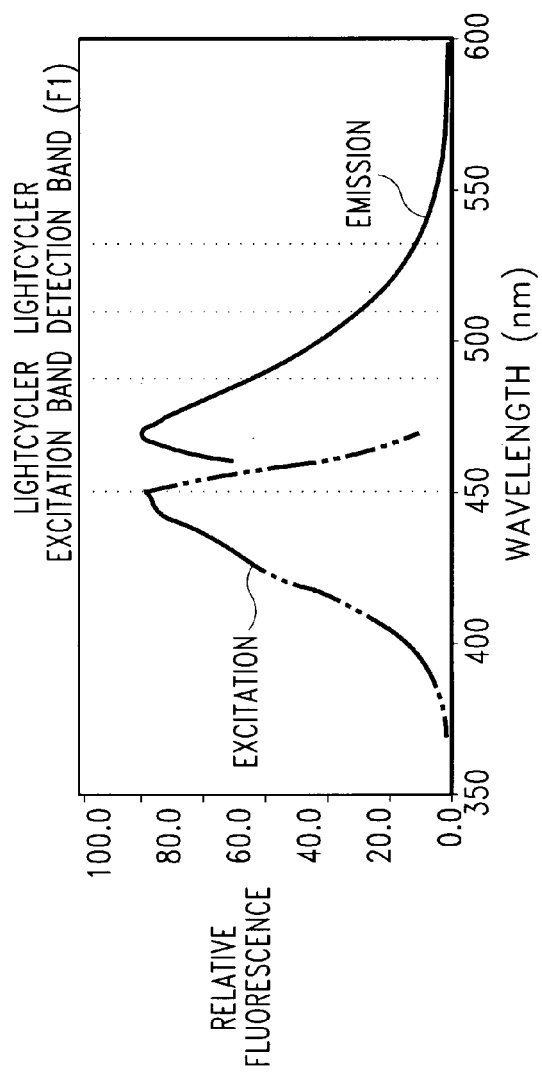
FIGS. 11A-B show the excitation and emission spectra for dye S5 (FIG. 11A) and SYBR® Green I (FIG. 11B).
Figure 11B:
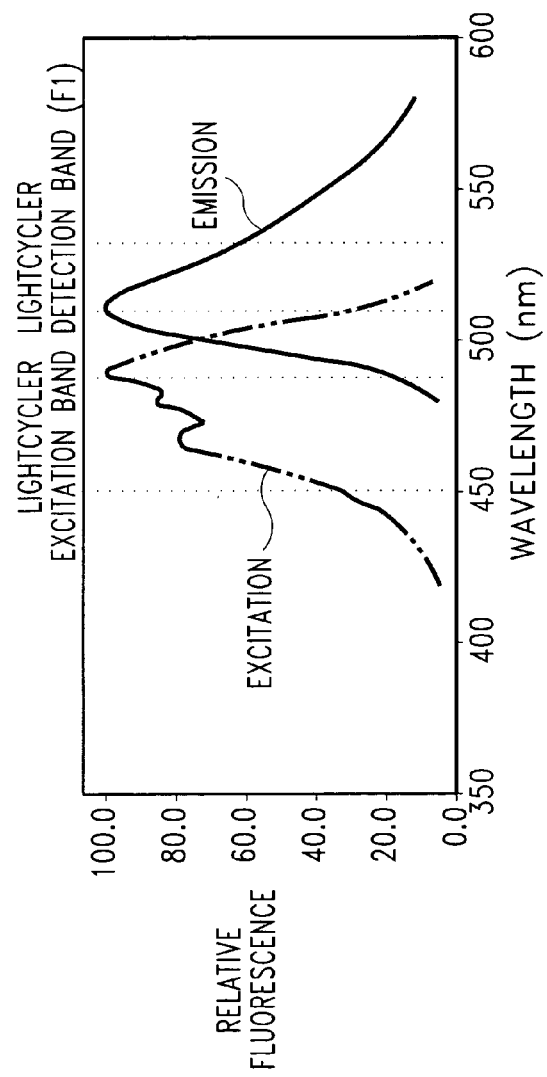

LightCycler® optics are well matched to SYBR® Green I excitation and emission (FIG. 11). Even though dye S5 is poorly matched to LightCycler® optics, the fluorescence signal observed on the LightCycler® with dye S5 at some PCR-compatible concentrations is greater than that usually observed from SYBR® Green I (data not shown).

Many of the other saturation dyes discussed herein are also "blue" dyes. While the fluorescence from such dyes may be observed with standard LightCycler® optics, in some examples, the optics of certain instruments have been modified to match the blue dyes better. Such modifications to the optics are noted in the relevant examples.

EXAMPLE 11

Genotyping of Beta-Globin Gene using X-Axis Adjustment and Fluorescence Difference Analysis A 110 bp fragment was amplified from the human beta globin region on chromosome 11 (accession# NG_000007). The 110 bp product included the sites of the common beta-globin mutations HbS and HbC. DNA was extracted from dried blood spots of 4 different individuals of each common genotype. The genotypes included 3 homozygous (AA, SS, and CC) and 3 heterozygous (AS, AC, and SC) types. The forward and reverse primers were ACACAACT-GTGTTCACTAGC (SEQ ID NO. 3) and CAACTTCATC-CACGTTCACC (SEQ ID NO. 4), respectively. Each 10 μl reaction contained 50 μg of genomic DNA, 0.50 μM each primer, 10 μM dye S5, 3 mM MgCl$_2$, 50 mM Tris, pH 8.3, 500 μg/ml bovine serum albumin, 0.2 mM each dNTPs, 0.04 U/μl Klentaq™ (AB Peptides, St. Louis, Mo.), 88 ng TaqStart™ antibody (CloneTech, Palo Alto, Calif.). PCR reaction conditions were as follows: one pre-cycling denaturation at 95° C. for 5 sec; 35 cycles of 94° C. for 0 sec, 50° C. for 2 sec with a slope of 2° C. per second. Single fluorescence acquisitions were taken for each sample after the 2 sec extension. After PCR amplification, the samples were cooled at a programmed rate of −20° C./sec. Immediately following the rapid cooling, melting was performed on a custom 24-bit high resolution melting instrument from 70° C. to 93° C. at a rate of 0.30° C./sec while continuously acquiring fluorescence.

Figure 12A:
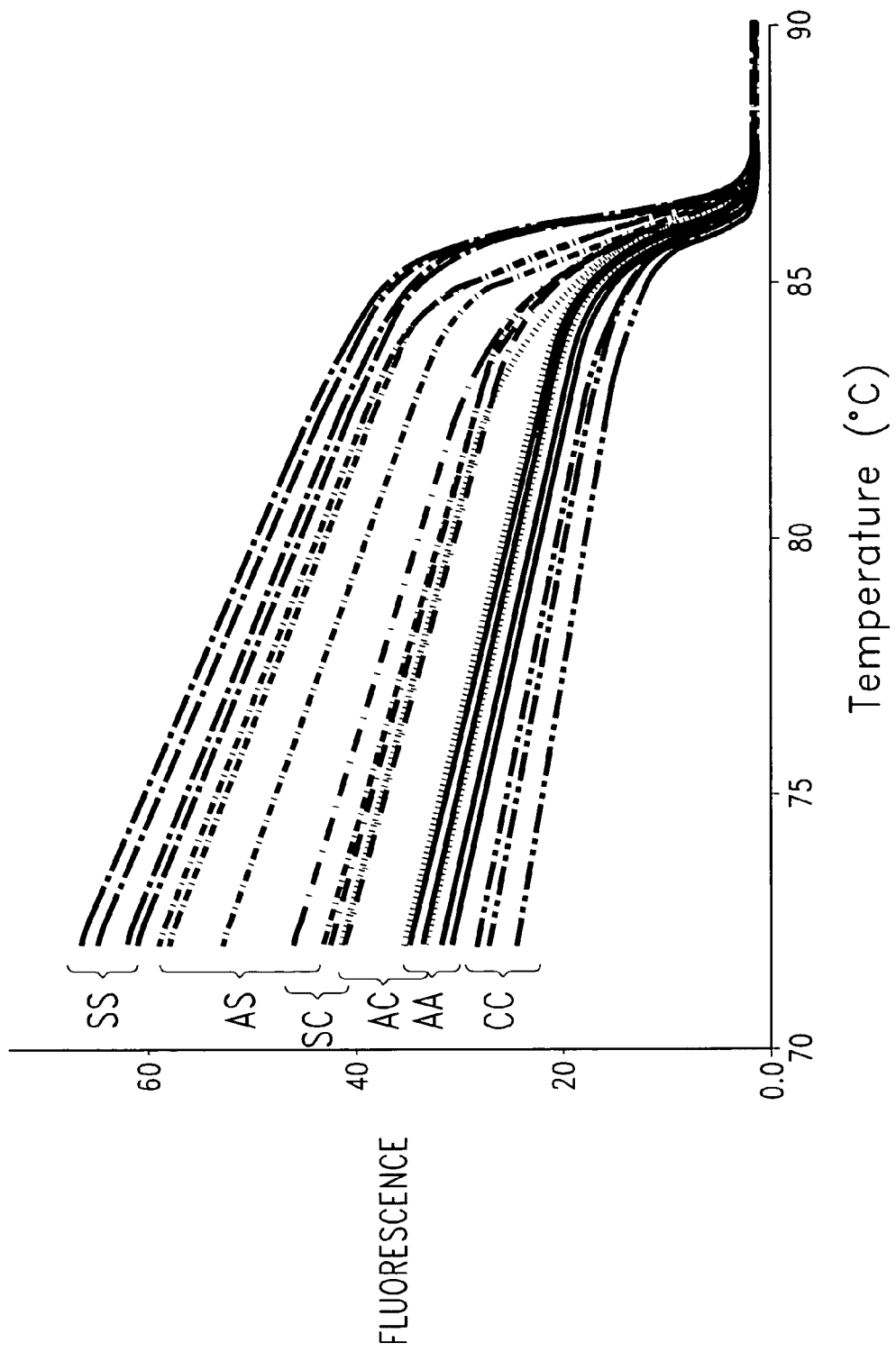
FIGS. 12A-D show high resolution melting curve analysis of quadruplicate samples of six different genotypes within a 110 bp fragment of beta-globin (_._ SS, ___AA, _.._CC, _.._SC, ........AC, .....AS)

High resolution melting curve data are obtained by measuring fluorescence as the temperature of the sample is increased. The original data from quadruplicate samples of 6 genotypes of beta-globin are shown in FIG. 12A. Note that the magnitude of the fluorescence is variable between different samples because of sample volume differences and variable capillary optics.

Figure 12B:
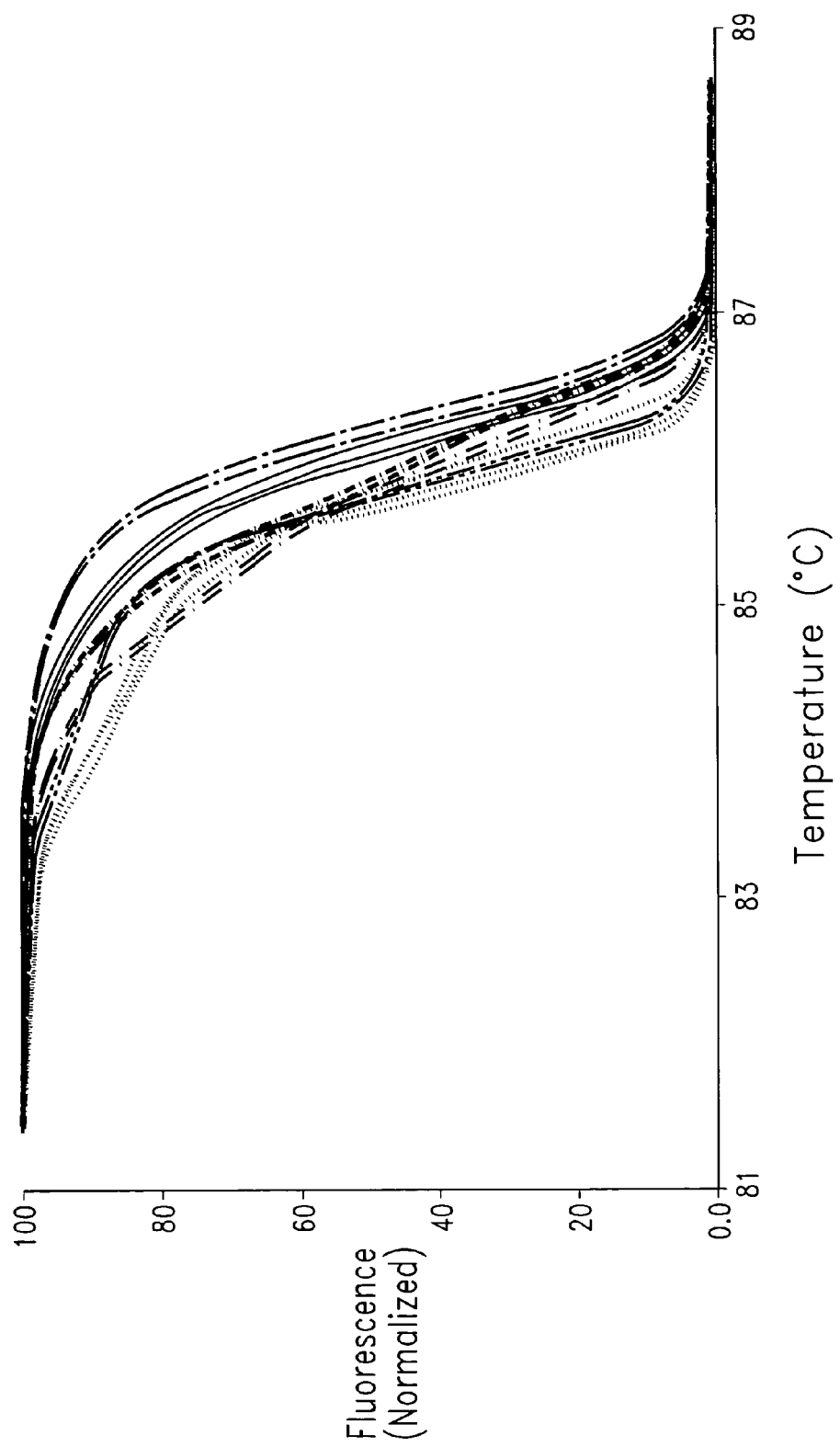

Magnitude differences between samples can be normalized by using linear baselines of each curve before and after the major transition. Specifically, two linear regions are selected, one before and one after the major transition. These regions define two lines for each curve, an upper 100% fluorescence line and a lower, 0% fluorescence line. The percent fluorescence within the transition (between the two regions) is calculated at each temperature as the percent distance between the extrapolated upper and lower lines. The normalized result for the beta globin data is shown in FIG. 12B. The quadruplicate samples of each genotype clearly group together, most clearly seen in this case around 84-85° C. There is still some variation within each genotype, secondary to temperature offsets between runs (note that there is about a 0.2° C. spread of quadruplicates within genotypes around 10-20% fluorescence). This sample variation can occur between two different samples or even between two different runs of the same sample. Different preparations, including preparations with different salt concentrations, can also provide a temperature offset. However, to at least a first approximation, these differences do not affect the shape of the curve.

Figure 12C:
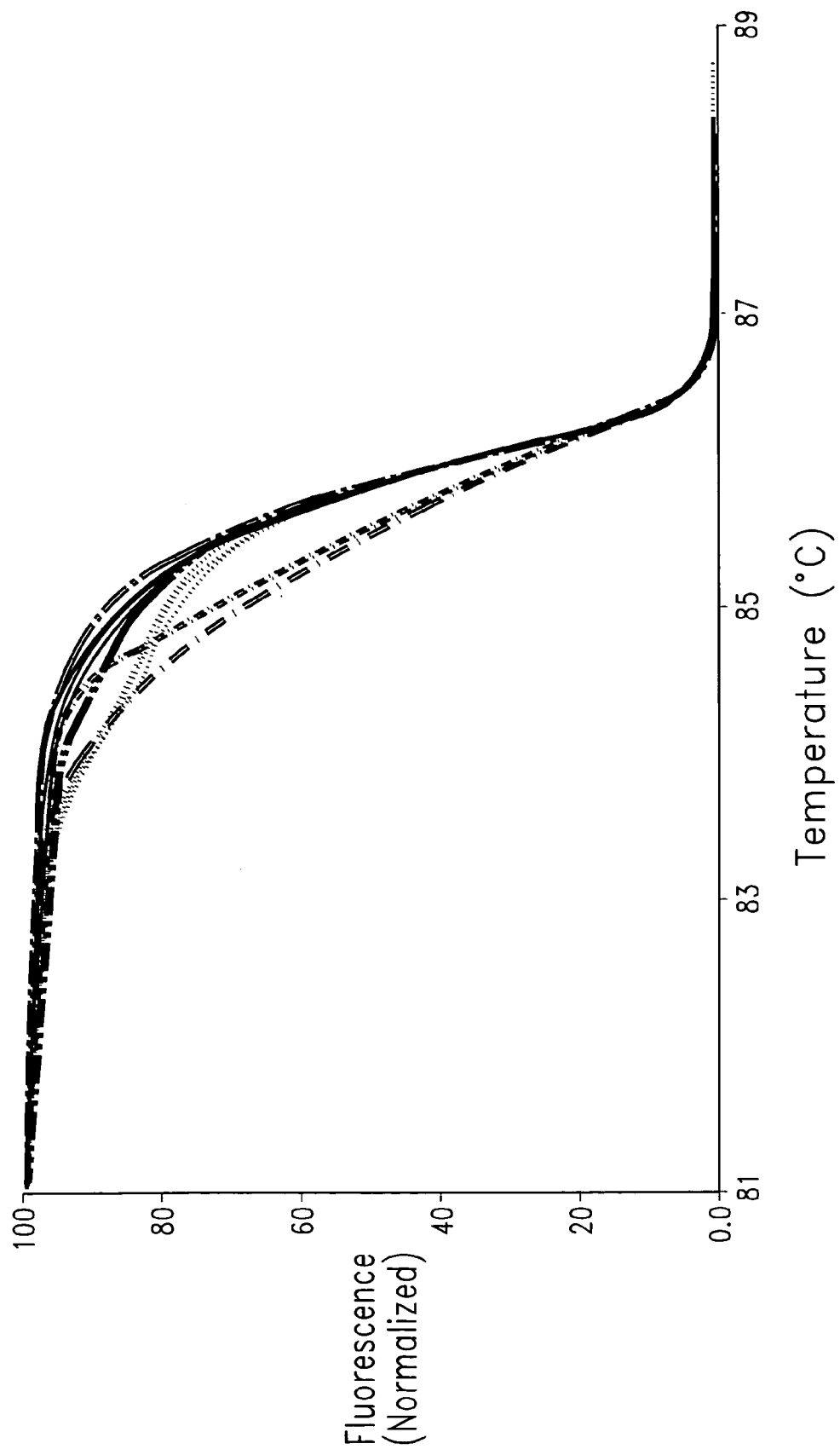

Temperature offsets between runs can be corrected by shifting the temperature axis of each curve so that they are superimposed over a given fluorescence interval. Illustratively, one sample is chosen as a standard, and the points within the florescence interval are fit to a quadratic. For each remaining curve, the required temperature shift for translation of each point within the fluorescence interval onto the quadratic is calculated. Each curve is then translated by the average shift to allow superimposition of the curves within the selected fluorescence interval. Amplification of a heterozygote produces low-temperature melting transitions of heteroduplexes as well as higher melting transitions of homoduplexes. If the curves are shifted to superimpose their high temperature, homoduplex region (low percent fluorescence), heteroduplexes may be identified by their early drop in fluorescence at lower temperatures, as seen in FIG. 12C. However, since the shape of different homoduplexes does not vary much, temperature shifting different homoduplexes may obscure any difference between them.

Figure 12D:
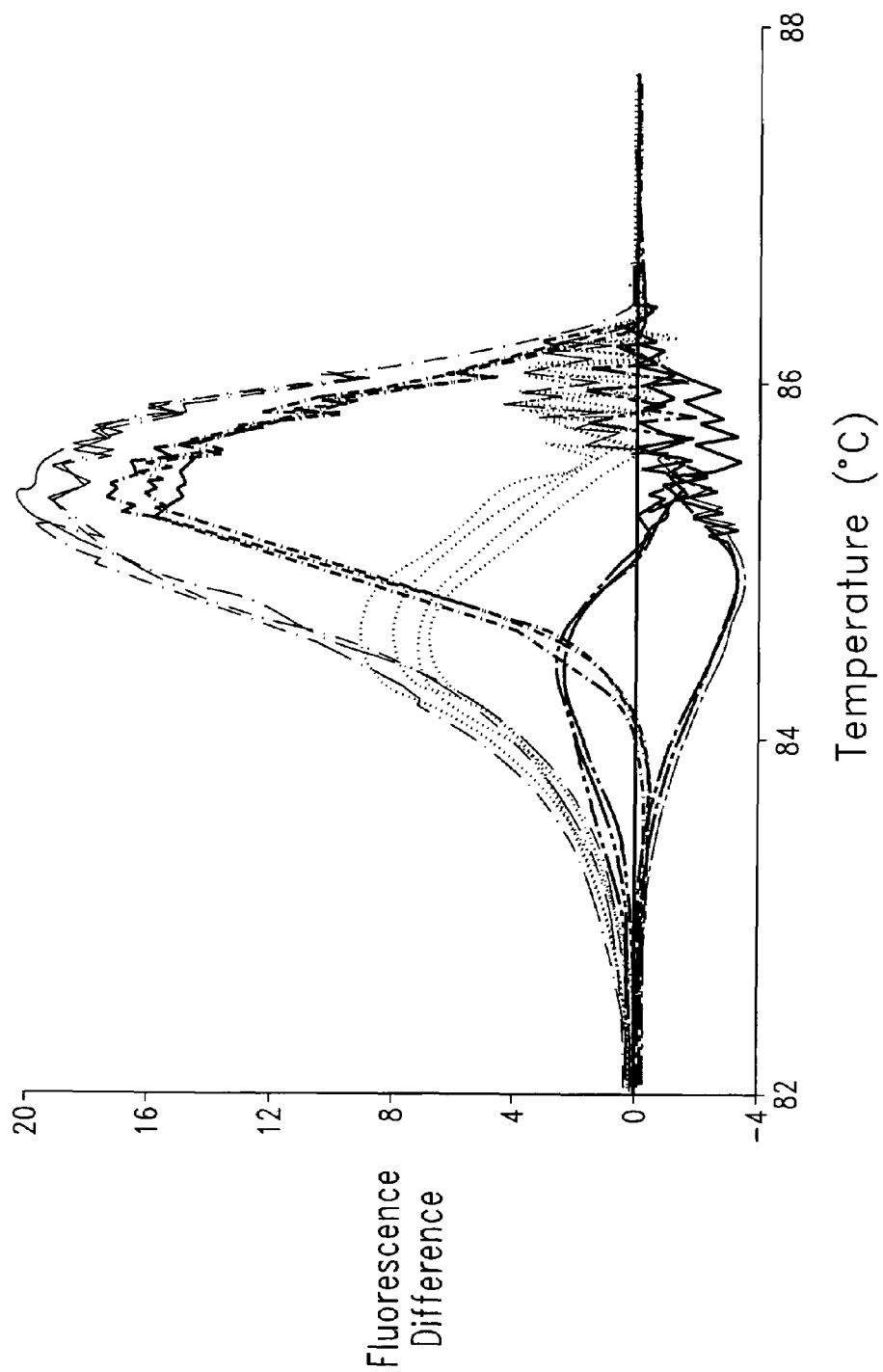

Finally, different genotypes are most easily observed by plotting the fluorescence difference between normalized (and optionally temperature shifted) melting curves. A standard genotype is first selected (illustratively, the beta-globin wild type AA is used). Then, the difference between each curve and the standard is plotted against temperature, as shown in FIG. 12D. The standard (subtracted from itself) is zero across all temperatures. Other genotypes trace unique paths and can be identified by visual pattern matching. Automated methods of feature extraction may also be used to assign genotypes. Additionally, while illustrative examples use saturating dyes and heteroduplex detection, it is understood that temperature shifting and temperature difference plots can be used for genotyping when heteroduplexes are not present, Illustratively for use in viral genotyping wherein the genome is haploid. Examples of such high resolution genotyping include hepatitis C genotyping, human papilloma virus genotyping, HIV genotyping, and bacterial identification by ribosomal DNA amplification.

Single parameters that correlate with genotype can be devised. For example, normalized curves can be used to determine the temperature at which different genotypes are, say 10% melted (90% fluorescence). This clearly distinguishes some genotypes, but not others (FIG. 12B). Alternately, the maximum slope of the curve could be used to distinguish homozygotes from heterozygotes, but different homozygotes are often similar in maximum slope. Finally, the area under the difference curves (FIG. 12D) could be used to define genotype, but such curves can have similar area yet trace different paths. While a combination of parameters may prove to be effective for automated genotyping determination, this technique is well suited for visual pattern matching.

It is understood that other normalization techniques are available and are within the scope of the present invention. For example, the HR-1 (Idaho Technology, Salt Lake City, Utah) has a setting that will automatically adjust the fluorescence value at a predetermined temperature (illustratively a fluorescence value of 100 at 40° C.), and melting curves from all samples will be aligned from the same fluorescence value. The difference between the normalization described above and this machine-controlled normalization is that with the machine-controlled normalization, the slopes of the curve before and after the transition are not flattened.

EXAMPLE 12

Analysis of Larger Amplicons

While short amplicons often result in greater genotyping differences, the dyes of the present invention also may be used to genotype larger amplicons. DNA melting domains are usually about 50 to 500 bp in length, and larger amplicons, for example 500-800 bp, have multiple melting domains. A sequence alteration in one domain may not affect melting of the other domains, and the variation observed within a domain may be independent of amplicon length. Thus, while examples are provided in the 400-650 bp range, there may be no upper limit to the size of PCR product that can be scanned for the presence of sequence alterations.

Moreover, because the melting of one domain appears to be independent of the melting of other domains, an invariant domain may be used as an internal control to adjust the X-axis (temperature axis), due to instrument and/or sample run variation. Heterozygotes are distinguishable from each other and from homozygotes because the shapes of the melting curves are different. The shapes of the melting curves are defined by the stability and/or kinetic melting rates of the heteroduplexes and homoduplexes present. Because multiple melting domains are present in larger amplicons, the variation in shape may occur in any portion of the curve. By adjusting the X-axis positioning of multiple curves to overlap the invariant portion of the curve, the variable portion of the curve is much easier to discern. Alternatively, by overlapping the variable portion of the curves, if various genotypes are present, the rest of the curves will vary. X-axis adjustment alternatively could be performed by adding (1) an external control nucleic acid, or (2) a dye with a second emission wavelength that does not interact with nucleic acid but whose fluorescence is dependent on temperature (a dye with a good temperature coefficient such as Cy5) to each sample prior to PCR or to melting. Temperature-axis shifting should then be performed according to the position of the melting transition of the control nucleic acid or to the intensity profile of the control dye.

Figure 13A:
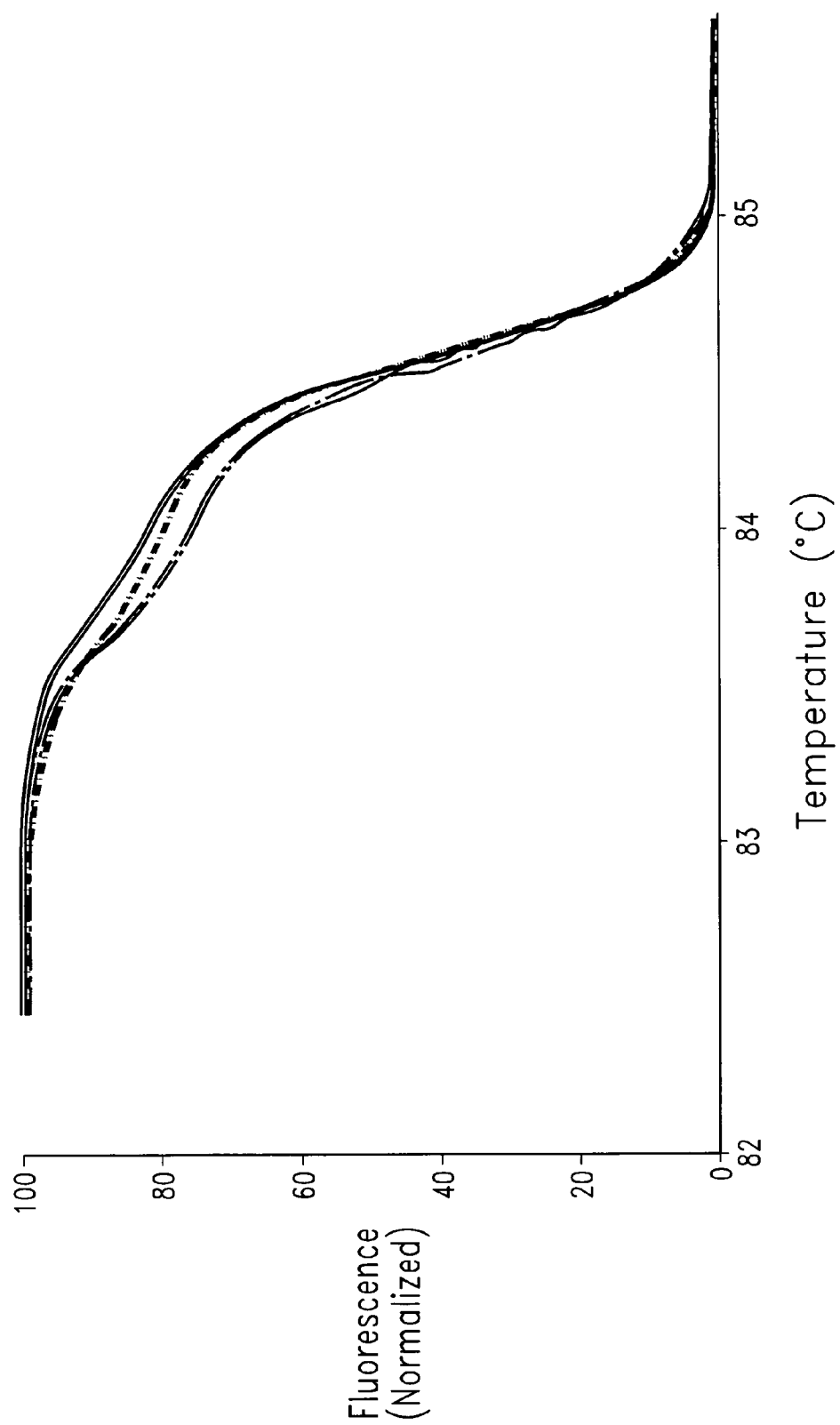
FIG. 13A shows melting curve analysis of duplicate samples of three genotypes of a 544 bp fragment of the human 5-Hydroxytryptamine receptor 2A (HTR2A) gene (_._ TC, ___CC, _.._TT). The data have been normalized and temperature shifted using the portion between 10 and 20% fluorescence. A theoretical melting map of the homoduplex is shown as FIG. 13B. The position of the single nucleotide polymorphism is marked (X).
Figure 14:
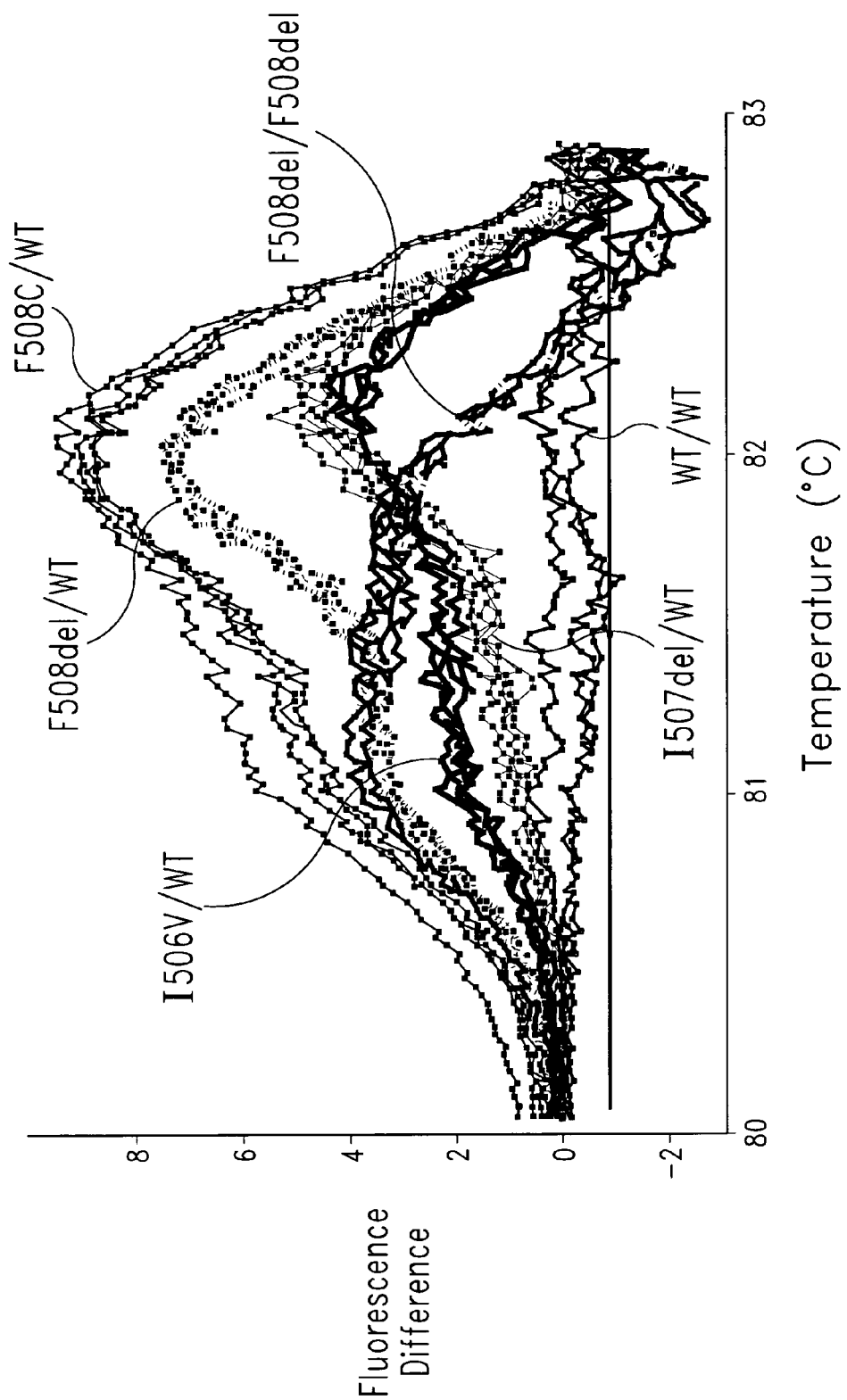
FIG. 14 shows a difference curve of six genotypes of a 612 bp fragment of the cystic fibrosis transmembrane conductance regulator (CFTR) gene. The plots have been normalized, temperature shifted by superimposing the portion between 30 and 40% fluorescence, and subtracted from one of the wild type plots.

FIGS. 13A and 14 illustrate two examples of analysis of larger amplicons. FIG. 13A shows amplification of a 544 bp fragment from the human 5-Hydroxytryptamine receptor 2A (HTR2A) gene, exon 2 (accession# NM_000621.1). The forward and reverse primers were CCAGCTCCGGGAGA (SEQ ID NO. 5) and CATACAGGATGGTTAACATGG (SEQ ID NO. 6), respectively. Each 10 μl reaction contained 50 ng of genomic DNA, 0.50 µM each primer, 1 µM dye S5, 2 mM MgCl$_2$, 50 mM Tris, pH 8.3, 500 µg/ml bovine serum albumin, 0.2 mM each dNTPs, 0.4 U Klentaq™ (AB Peptides, St. Louis, Mo.), and 88 ng TaqStart™ antibody (CloneTech, Palo Alto, Calif.).

PCR reaction conditions were as follows: 40 cycles of 92° C. for 0 sec, 60° C. for 2 sec, 74° C. for 25 sec. After PCR amplification, the samples were cooled at a programmed rate of −20° C./sec. Immediately following the rapid cooling, melting was performed on a custom 24-bit high resolution melting instrument from 70° C. to 93° C. at a rate of 0.30° C./sec while continuously acquiring fluorescence.

Figure 13B:
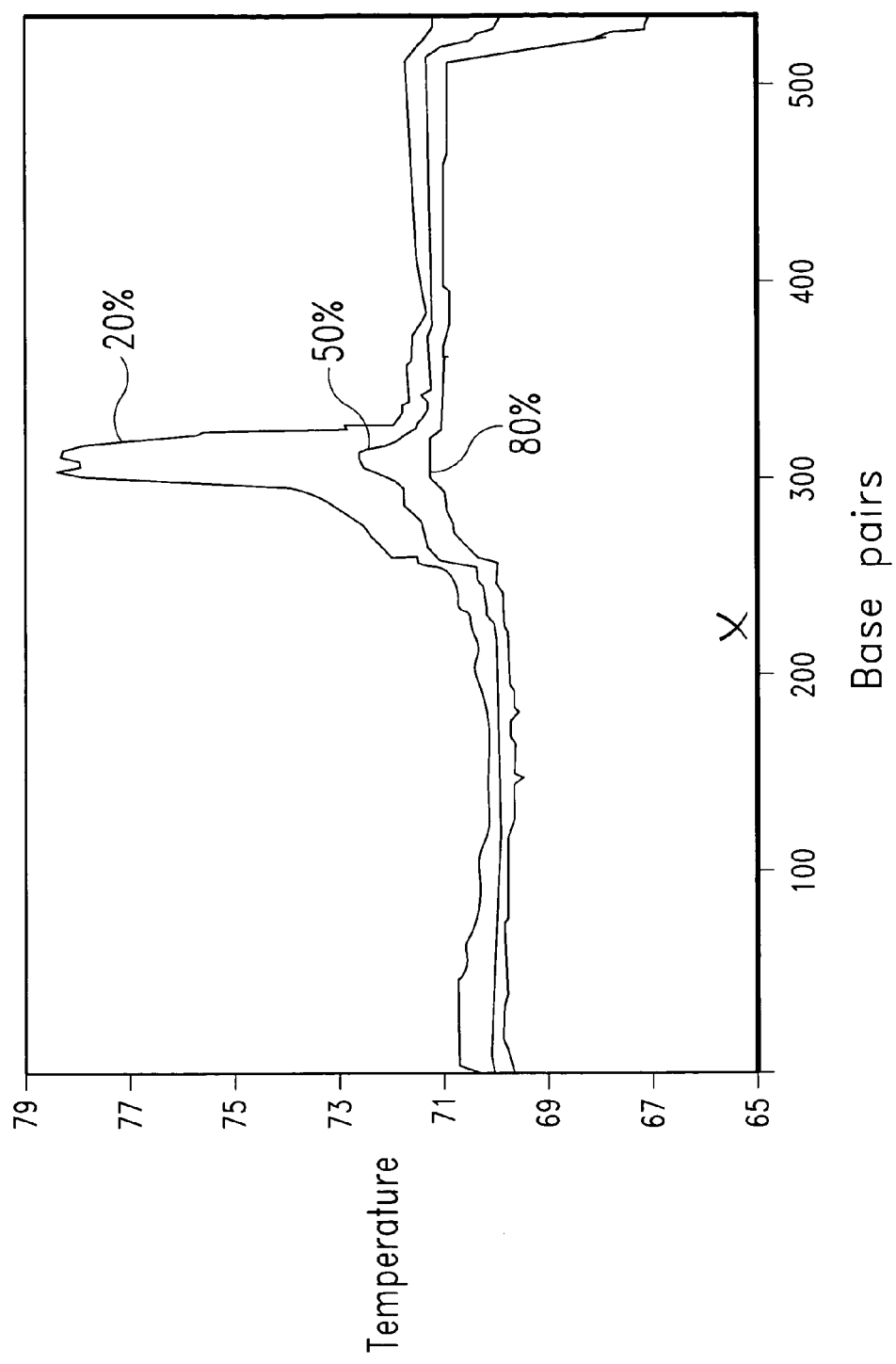

Duplicate samples of each genotype (CC, TC, and TT) were amplified and analyzed, as shown in FIG. 13A. The data were normalized and temperature shifted as described in Example 11, except that curves were superimposed between 10 and 20% fluorescence. FIG. 13B shows a predicted melting map of the homoduplex and the position of the polymorphism in the lower melting domain. The experimental data show two apparent melting domains. All genotypes are similar in the higher melting domain. Genotypes differ in the lower melting domain, where the heterozygote shows typical behavior of low melting heteroduplexes with the heterozygote curve crossing the lower melting homozygote curve and approximation to the higher temperature homozygote with increasing temperature.

FIG. 14 shows difference curves for amplification of a 612 bp fragment from the cystic fibrosis transmembrane conductance regulator (CFTR) gene, exon 10 (accession# M55115). The forward and reverse primers were AGAATATACACTTCTGCTTAG (SEQ ID NO. 7) and TATCACTATATGCATGC (SEQ ID NO. 8), respectively. Each 10 µl reaction contained 50 ng of genomic DNA, 0.50 µM each primer, 10 µM dye S5, 3 mM MgCl$_2$, 50 mM Tris, pH 8.3, 500 µg/ml bovine serum albumin, 0.2 mM each dNTPs, 0.4 U Klentaq™ (AB Peptides, St. Louis, Mo.), and 88 ng TaqStart™ antibody (CloneTech, Palo Alto, Calif.). PCR reaction conditions were as follows; 35 cycles of 89° C. for 0 sec, 58° C. for 8 sec, 74° C. for 35 sec. Single fluorescence acquisitions were taken for each sample after the 35 sec extension. After PCR amplification, the samples were cooled at a programmed rate of −20° C./sec. Immediately following the rapid cooling, melting was performed on a custom 24-bit high resolution melting instrument from 60° C. to 87° C. at a rate of 0.30° C./sec while continuously acquiring fluorescence. In this example, heterozygote differentiation was best when the middle part of the curve (30-40% fluorescence) is used for X-axis adjustment. Finally, the fluorescence of each plot was subtracted from one of the wild type plots to give the difference plots shown in FIG. 14. Each sequence alteration is clearly different from the wild type and all genotypes can be differentiated.

EXAMPLE 13

Targeted Detection and Multiplexing with Saturation Dyes

The dyes of the present invention may be used as a donor to excite an acceptor dye attached to an oligonucleotide probe. Because these dyes may be used at or near saturating concentrations to bind to the hybridized probe at a high density (approximately two dye molecules every three base pairs), the dye is available throughout the length of double-stranded DNA for fluorescence resonance energy transfer. A probe with an acceptor dye is added to the reaction before PCR, amplified and is detected when hybridized to the product. The binding of the saturation dye at high density to the duplex provides favorable excitation to the acceptor dye on the probe, producing a high degree of acceptor fluorescence. Previously, dyes with a high bp/dye ratio were used and only produced low levels of acceptor fluorescence.

Multicolor experiments can be performed with multiple probes. For example, total amplicon melting can be monitored at 470 nm, the emission of a fluorescein-labeled probe could be monitored at 515, a HEX-labeled probe (that hybridizes to a different segment of DNA internal to the primers) monitored at a third wavelength, and a TET-labeled probe (that hybridizes to yet a different segment internal to the primers) monitored at a 4th wavelength. Color compensation, as is well known in the art, is used to deconvolute the overlapping four signals. The result is that the first signal can be used to scan for mutations over the whole amplicon, while the 2nd, 3rd, and 4th signals allow genotyping of smaller regions within the amplicon.

EXAMPLE 14

High Resolution Melting Curve Analysis for Genotype Comparison

Dyes of the invention can be used to determine whether any two individuals share the same alleles on a gene fragment. In the previous examples, the genotype (including the exact allele, heterozygosity, and haplotype) of a reference sample was known. In some applications, the exact genotype of a reference sample need not be known, as long as high-resolution melting curve analysis makes it possible to determine whether a sample of another individual (or of unknown origin) is the same as the reference. An illustrative example is the identification of HLA alleles shared among family members.

Human Leukocyte Antigens (HLA) are cell surface proteins of white blood cells and other tissues of the body which play a key role in immune recognition, and thus in transplant tolerance or rejection. Matching of HLA alleles between donor and recipient is important for organ transplant. HLA proteins form two major groups: class I, and class II. Each group is encoded by multiple genes. The currently accepted techniques for determining the HLA allelotype of a tissue include serotyping with specific antibody reagents, hybridization with nucleic acid probes, and direct sequencing of the HLA genes. Because a large number of genes and loci need to be tested, the cost to determine the HLA allelotype is over $1,000 per person. Complete genotyping of HLA is necessary when donor and recipient are unrelated. However there is about a 25% chance of a perfect HLA match between siblings and for this reason organ transplant between siblings is preferred when HLA matches indicate that it is possible. In this case it is only necessary to demonstrate that the donor and recipient relatives share the same HLA alleles. Determining the exact identity of the shared alleles is not necessary.

Figure 15:
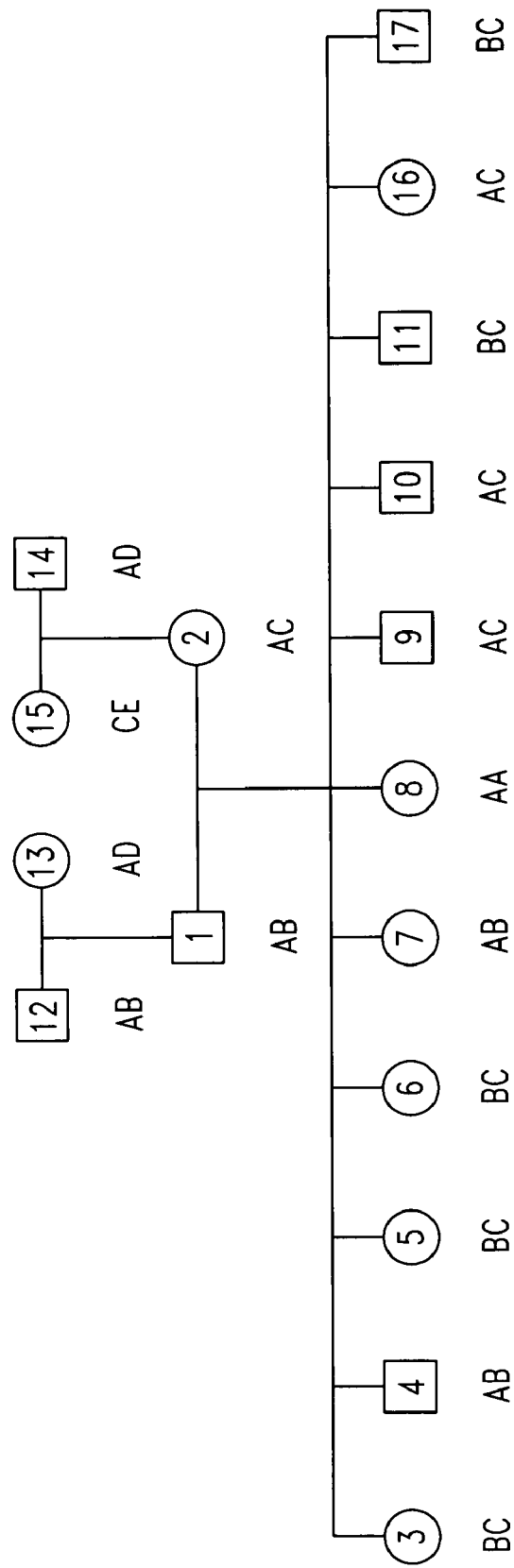
FIG. 15 shows the pedigree of CEPH referenced Utah family 1331. Genotype of HLA-A of Utah family 1331 are as follows: A:02011; B:3101; C:2402101; D:03011; E:01011. Each individual is numbered. Female (circle); male (square).

Genomic DNA samples of CEPH/Pedigree Utah family 1331 were obtained from the Coriell Institute. There are 17 people across three generations in this family including four internal grandparents, two parents, and eleven children (pedigree of family 1331 is shown in FIG. 15). Two other samples with well known homozygous genotypes of HLA-A BM15(0101) and BM16(0202) were also obtained from Coriell.

Amplification of two exons of the HLA-A gene were performed as follows: HLA class I genes are so similar over of the length of their coding exons that it is difficult to design PCR primers that amplify only the HLA-A gene and not the related class I genes. A nested PCR strategy was adopted in which an initial round of PCR specifically amplified a large (948 bp) fragment of the HLA-A gene followed by secondary amplification of that product using internal primers. The primers used in the first PCR hybridized to HLA-A intron 1 (forward primer 5'-GAAAC(C/G)GCCTCTG(C/T)GGG-GAGAAGCAA (SEQ ID NO. 9, SEQ ID NO. 10, SEQ ID NO. 11, SEQ ID NO. 12)) and intron 4 (reverse primer 5'-TGTTGGTCCCAATTGTCTCCCCTC (SEQ ID NO. 13)). In the secondary PCRs the forward primers 5' AGC-CGCGCC(G/T)GGAAGAGGGTCG (SEQ ID NO. 14, SEQ ID NO. 15) and reverse primer 5' GGCCGGGGTCACT-CACCG (SEQ ID NO. 16) were used to amplify a 335 bp segment of HLA-A exon 2. The forward 5' CCC(G/A) GGTTGGTCGGGGC (SEQ ID NO. 17, SEQ ID NO. 18) and reverse primer 5' ATCAG(G/T)GAGGCGCCCCGTG (SEQ ID NO. 19, SEQ ID NO. 20) were used to amplify a 366 bp fragment of HLA-A exon 3. In the primer sequences of this example, (N/N') represents that the primer is a mixture of nucleotide sequences having equal percentages of N and N' at that position. For example, the forward primer for the 335 bp segment of HLA-A exon 2 contains an equal mixture of two nucleotides, with either a G or an A at the fourth position, as represented by SEQ ID NO. 17 and SEQ ID NO. 18. The forward primer for the HLA-A intron 1 has two such sites, and thus is an equal mixture of four nucleotides, as represented by SEQ ID NO. 9, SEQ ID NO. 10, SEQ ID NO. 11 and SEQ ID NO. 12.

All PCRs were performed in glass capillaries using the LightCycler®. The initial PCR contained 0.5 µM forward and reverse primers, 50 ng genomic DNA in a buffer of 3 mM Mg$^{++}$, 50 mM Tris-HCl pH 8.3, 500 µg/ml BSA and 20 µM of dye D6 in 10 µl. Cycling conditions were 94° C. for 20 s followed by 40 cycles of 94° C. 1 s, 62° C. for 0 s, 72° C. for 1 min. The secondary, nested PCRs contained 0.25 µM forward and reverse primer, ¹⁄₁₀₀₀₀ of first PCR product in the same buffer containing 2 mM Mg$^{++}$. Cycling conditions were 94° C. for 5 s followed by 25 cycles with 94° C. 1 s, 65° C. for 0 s, 72° C. for 8 s.

Figure 16A:
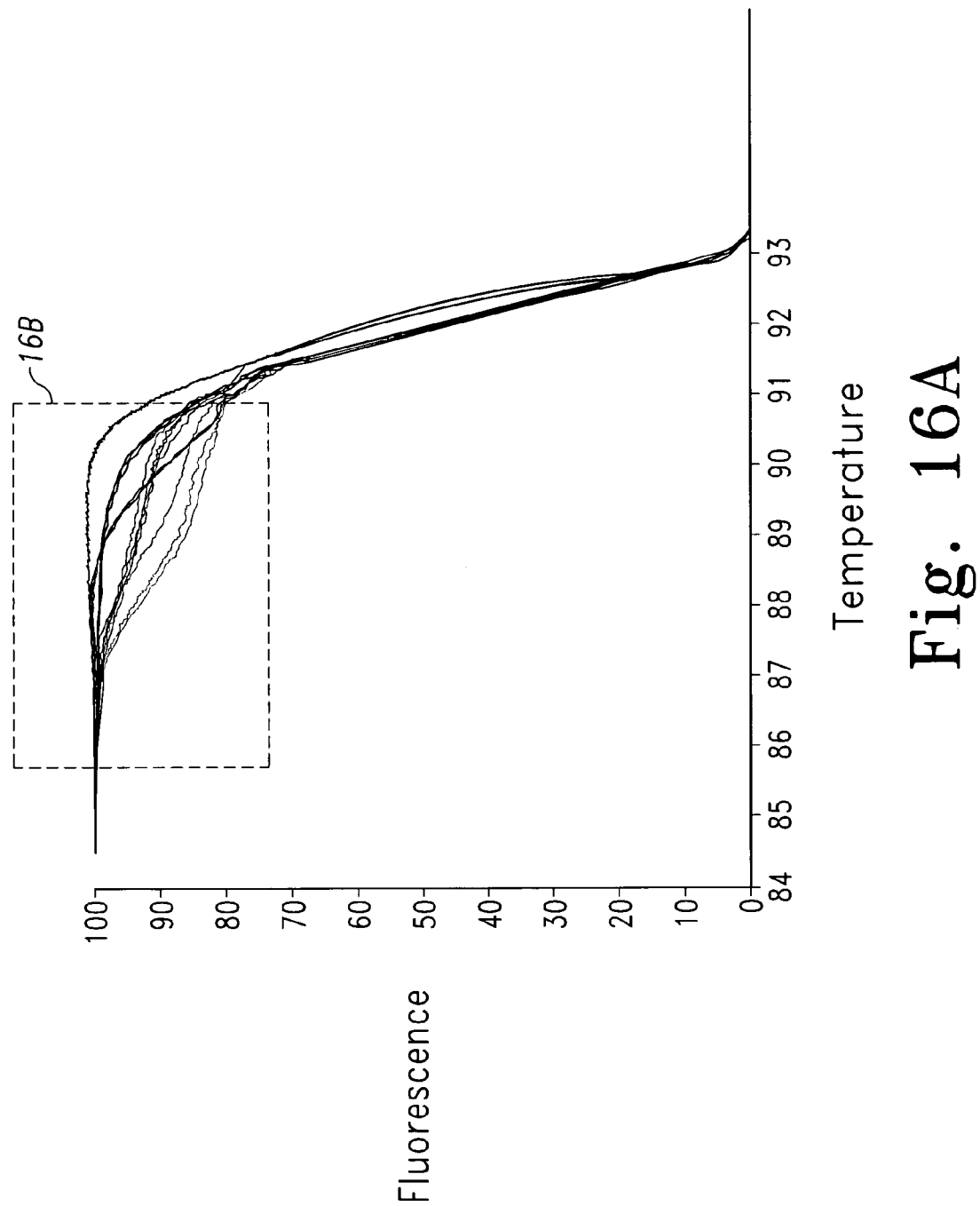
FIGS. 16A and B show the melting curve of Utah family 1331 members. Six different melting curves representing six genotypes in HLA-A exon 2 exist among 17 family members.
Figure 16B:
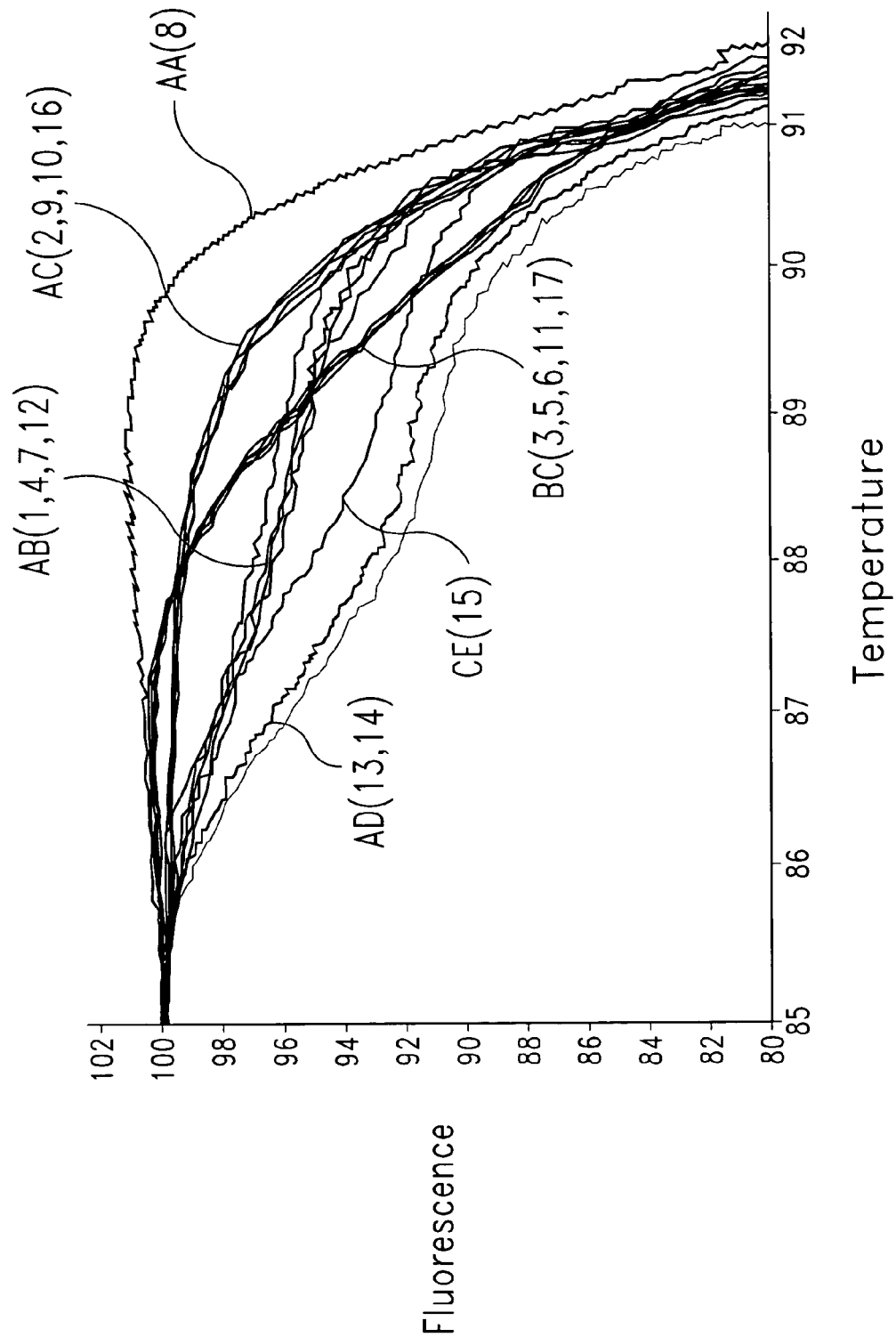

After the secondary amplification the glass capillaries were transferred to the high resolution melting instrument HR-1, and a melt was performed. The sample was heated from 60° C. to 95° C. at a rate of 0.3° C./s and fluorescence (450 excitation/470 emission) and temperature measurements were acquired every 40 s (FIGS. 16A-B). The nested amplification products were sequenced by the ABI 3700. Sequencher version 4.0 was used for the sequence analysis.

Concordance of melting curve analysis and sequencing results were determined as follows: Melting curve analysis of the exon 2 and exon 3 PCR products amplified from the 17 members of the CEPH/Pedigree Utah family 1331 clustered in six different groups (FIGS. 16A-B). This suggested that there are six different HLA-A genotypes in this family. The exon 2 and exon 3 PCR products were sequenced, and the results confirmed the melting curve analysis, identifying the six genotypes as: HLA-A 02011/3101 (herein referred to as genotype AB) for family members 1, 4, 7, 12; HLA-A 3101/2402101 (genotype BC) for family members 3, 5, 6, 11, 17; HLA-A 02011/2402101 (genotype AC) for family members 2, 9, 10, 16, HLA-A 02011/03011 (genotype AD) for family members 13, 14; HLA-A 02011/02011 (genotype AA) for family member 8 and HLA-A 2402101/01011 (genotype CE) for family member 15 (Results for exon 2 is shown in FIGS. 16A-B).

In some cases, the amplification products from siblings may show identical or nearly identical melting curves despite having different genotypes. In such cases mixing the genomic DNA from the two siblings before the initial PCR followed by the two amplification steps and melting curve analysis can differentiate identical from non-identical genotypes. In particular if the siblings have identical genotypes, the mixed melting curve will be identical to those performed separately. If siblings have different genotypes then the mixed melting curve will be different from that of the individual melting curves. Mixing experiments within each group confirmed that the members of each group shared identical genotypes.

Figure 17:
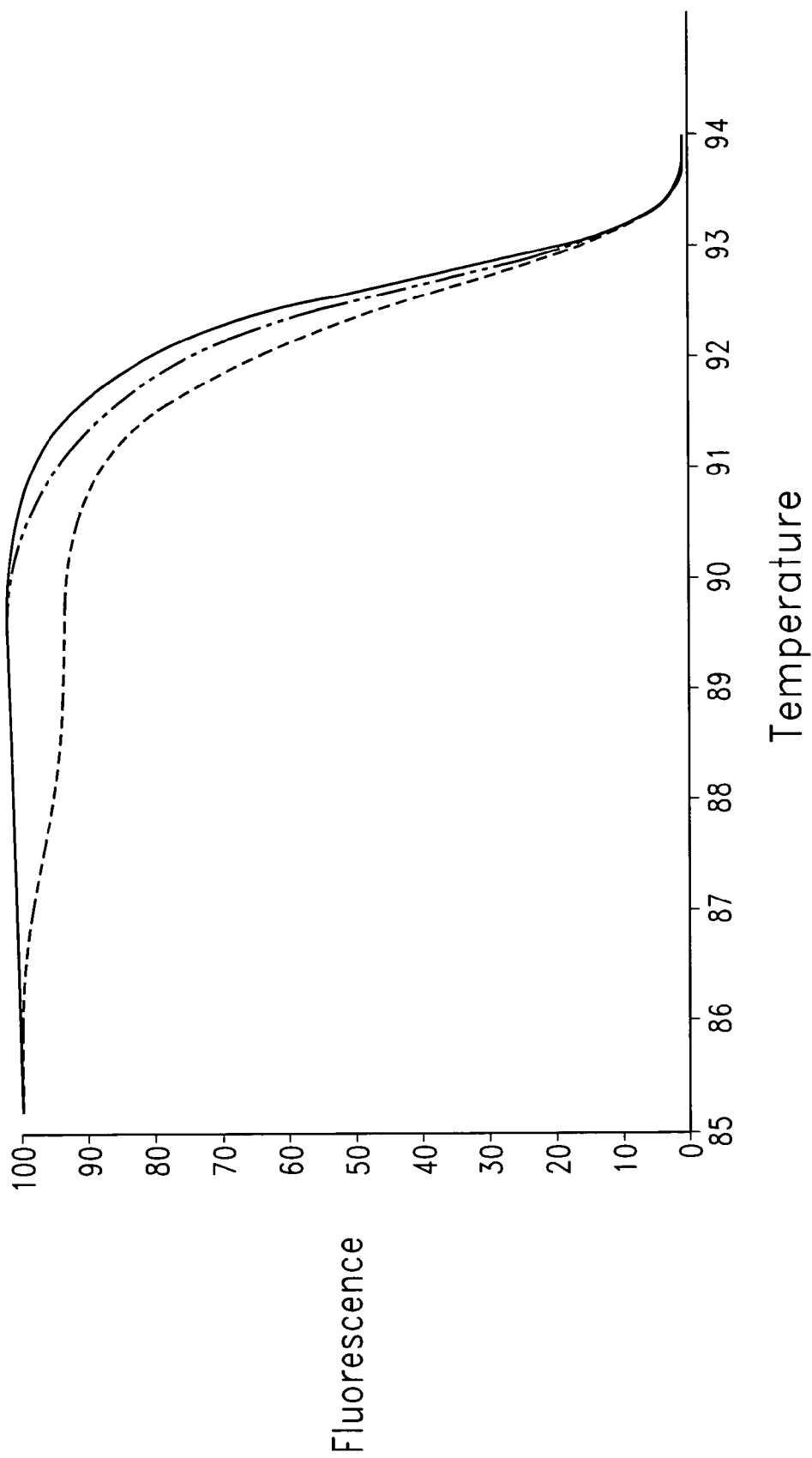
FIG. 17 shows the determination of genotypes of two samples by mixing (___BM15,_.._BM16,....BM15+BM16). Two homozygous samples BM15(0101) and BM16 (0201) have a 15-bp difference on the HLA-A exon 2. The melting curve of BM15 and BM16 are similar when taken separately, but when mixed, the 15-bp mismatch shifts the melting curve.

Another example of the mixing analysis technique was demonstrated by two homozygous samples BM15 (0101) and BM16 (0201). In this case, the two alleles have a total of 15 nucleotide differences spread over the length HLA-A exon 2, but they show similar melting curves. The melting curve of the mixed samples was significantly shifted to the left (lower melting temperature) due to the 15 mismatches present in the heterohybrids generated in the mixed sample PCR from HLA-A exon 2 (see FIG. 17).

EXAMPLE 15

Monitoring Amplification in Real-Time with Saturating Dyes

A 60 bp fragment of the HTR2A gene was amplified with forward and reverse primers ACCAGGCTCTACAGTAA (SEQ ID NO. 21) and GTTAAATGCATCAGAAG (SEQ ID NO. 22), respectively. Amplification was performed using the reagents described in Example 12 but with modifications to the cycling parameters, which were 95° C., 0 s; 62° C., 2 s; 74° C., 20 s using the LightCycler®. Various concentrations of SYBR® Green I, D6, Z6, and N7 were independently present in the reaction mixture. Fluorescence data were acquired once each amplification cycle, up to 36 cycles. Fluorescence crossing points (Cp), calculated as the second derivative maximum of the amplification plot (cycle number plotted on the x-axis against fluorescence intensity on the y-axis), were obtained as follows:

TABLE 4

| Dye present in reaction | Dilution/ Concentration | Cp |
| --- | --- | --- |
| SYBR® Green I | 1:2,500 | No amplification |
| | 1:5,000 | 26 |
| | 1:10,000 | 26 |
| | 1:20,000 | Signal too weak |
| D6 | 250 µM | No amplification |
| | 125 µM | 28 |
| | 63 µM | 27 |
| | 31 µM | 27 |
| | 16 µM | 26 |
| | 8 µM | 26 |
| | 4 µM | 26 |
| | 2 µM | 26 |
| | 1 µM | Signal too weak |
| Z6 | 20 µM | No amplification |
| | 10 µM | 31 |
| | 5 µM | 27 |
| | 2.5 µM | 26 |
| | 1.3 µM | 26 |
| | 0.7 µM | 25 |
| | 0.4 µM | 25 |
| | 0.2 µM | Signal too weak |
| N7 | 62 µM | No amplification |
| | 31 µM | 27 |
| | 16 µM | 27 |
| | 7.9 µM | 26 |
| | 4.0 µM | 26 |

TABLE 4-continued

| Dye present in reaction | Dilution/ Concentration | Cp |
|---|---|---|
| | 2.0 μM | 26 |
| | 1.0 μM | 26 |
| | 0.5 μM | 26 |
| | 0.2 μM | 26 |
| | 0.1 μM | Signal too weak |

The Cp value, which represents the cycle number at which signal rises above background, is expected to increase when inhibitors present in the reaction affect the efficiency of amplification. Under the conditions of these experiments, however, inhibition by increasing amounts of dye resulted not as a gradual increase in Cp, but as a sudden and complete elimination of amplification. Due to the small size of the amplicon (which results in a lower signal compared to larger amplicons), SYBR® Green I dye could only be used in the range of two-fold concentrations for real-time monitoring. In contrast, dyes D6, Z6 and N7 could be used in the range of 32 to 128-fold concentrations. It is contemplated that many saturating dyes have a wide range of concentration that can be used in real-time monitoring of amplification.

EXAMPLE 16

SNP Typing by Use of Unlabeled Probes and Saturating Dyes

As shown in FIG. 7, saturation dyes have the ability to detect melting signatures of multiple dsDNA species present in a reaction mixture without having low temperature melting obscured by redistribution of dye from low to high melting temperature (Tm) duplexes. This aspect of saturation dyes allows the use of unlabeled probes for genotyping. When an unlabeled probe is mixed with the amplicon in the presence of a saturation dye, the melting signature of both the amplicon and the probe-target duplexes can be observed at the same time. Changes in melting profile can be used to detect the presence of sequence variances under the probe, as well as elsewhere in the amplicon. Optionally, by truncating the melting process prior to the melting transition of the amplicon, one can study just the melting of the unlabeled probe. The use of unlabeled probes for effective genotyping and mutation scanning has not been possible with dyes that are currently used for real-time PCR, such as SYBR Green I (compare FIGS. 21B versus 21C). Further, because of the properties of the saturation dyes, genotyping can be performed in the presence of the unlabeled probe without need for the unlabeled probe or the target nucleic acid to be immobilized on a surface. In each of the illustrative embodiments, the dye, unlabeled probe, and target nucleic acid are all free in solution.

A 300 bp amplicon was generated by PCR in a LightCycler® (Roche Applied Systems, Indianapolis, Ind.) using primers 5' GATATTTGAAGTCTTTCGGG (the "reverse" primer, SEQ ID NO. 23) and 5' TAAGAGCAACACTAT-CATAA (the "sense" primer, SEQ ID NO. 24) in a 10 μl reaction mixture that contained an initial template plasmid DNA (Example 5) of 1×10$^6$ copies, 0.5 μM 3'-end phosphorylated probe, 3 mM MgCl$_2$, 50 mM Tris, pH 8.3, 0.2 mM each dNTP, 500 μg/ml BSA, 20 μM dsDNA dye D6 (Example 1) and 0.4 U Taq polymerase (Roche). For symmetric amplification, 0.5 μM of each primer was used. For asymmetric amplification, primer ratios were varied between 10:1, 20:1 and 50:1. PCR was performed with an initial denaturation at 95° C. for 10 s, followed by 45 cycles of 95° C. for 1 s, 55° C. for 0 s, 72° C. for 10 s (or 5 s in the absence of probe). At the end of amplification, samples were denatured at 95° C. for 0 s, annealed at 40° C. for 0 s followed by melting analysis at a rate of 0.2° C./s up to 90° C. (LightCycler®), or alternatively, up to 75° C. at a rate of 0.3° C./s (HR-1) or 0.1° C./s (LightTyper®) with modified optics of 450 nm excitation and 470 nm detection).

Figure 18A:
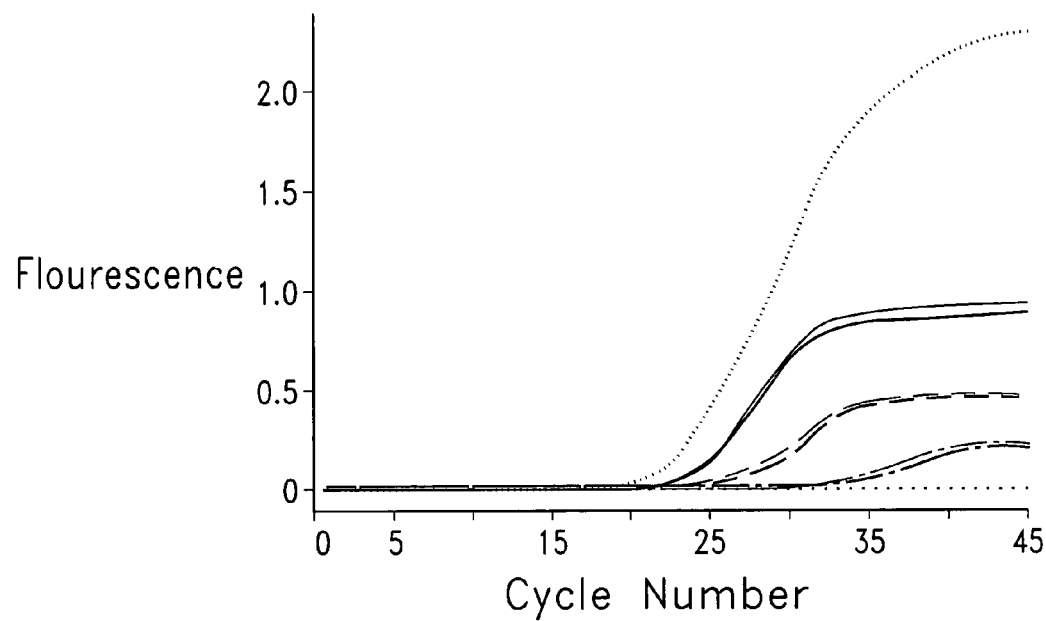
FIGS. 18A and B show the results of an optimization experiment for genotyping with an unlabeled probe following asymmetric PCR.
Figure 18B:
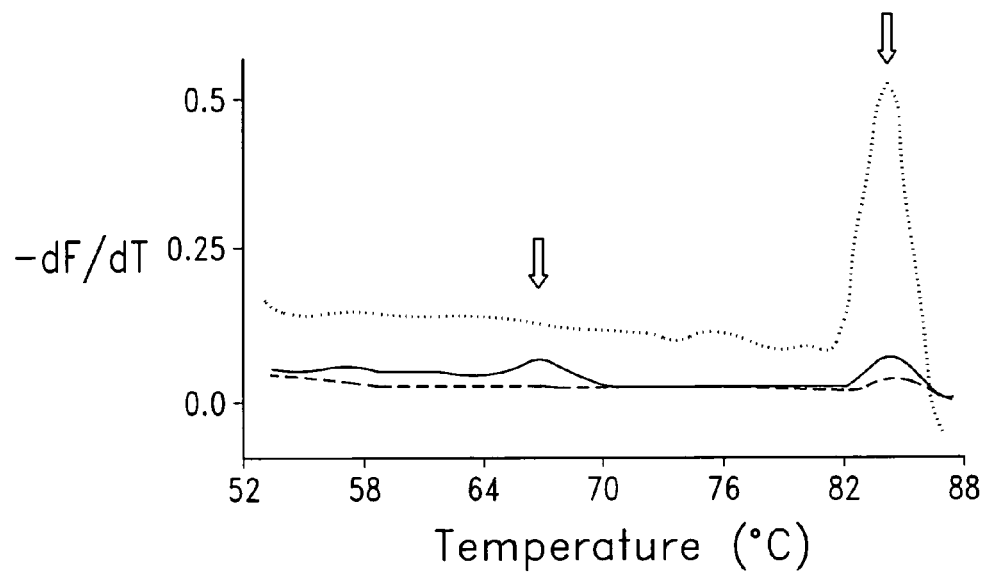
FIG. 18B is a derivative melting curve showing melting peaks (·······symmetric (0.5 μM of each primer); ____0.05 μM sense primer and 0.5 μM reverse primer; ___0.5 μM sense primer and 0.05 μM reverse primer).
Figure 19:
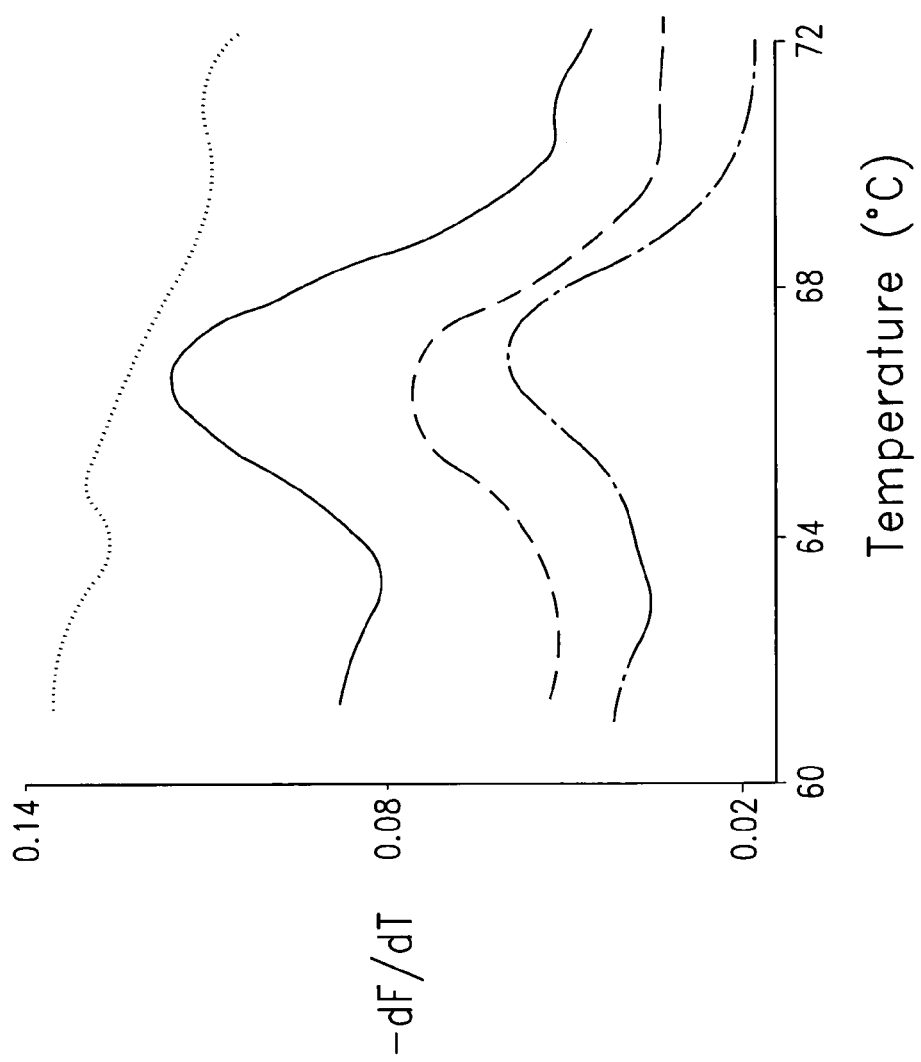
FIG. 19 is similar to FIG. 18B, showing melting peaks after asymmetric amplification ·······(symmetric (0.5 μM of each primer); solid line 0.5 μM sense primer and 0.05 μM reverse primer; ____0.5 μM sense primer and 0.025 μM reverse primer; _.._0.5 μM sense primer and 0.01 μM reverse primer).

The target strand of the amplified product should be adequately available for probe hybridization. In many instances this may be accomplished by providing the primer that generates the probe-hybridizing strand (the "sense" primer) in excess compared to the other primer (the "reverse" primer). FIGS. 18A and 19 show results of an optimization experiment in which amplicons generated by varying ratios of primers were examined. While the optimum primer ratio may be different for each amplicon and/or each amplification system, melting of the probe is often observed when the ratio between sense and reverse primers is about 10 to 1 or higher. Note that in the LightCycler® data, melting peaks of both the probe and the amplicon are observed at such a primer ratio (FIG. 18B). It is understood that, while the examples presented herein use this "asymmetrical" PCR to generate a greater abundance of the target strand, other methods of amplification may be well suited, particularly amplification methods such as NASBA, TMA, and rolling circle amplification that favor amplification of one strand. Alternatively, strand separation may occur subsequent to PCR, illustratively by incorporating a biotin tail or a poly-A tail (or other sequence) in the amplicon through use of properly designed primers. In yet another alternative example, melting analysis may be conducted on single-stranded nucleic acid subsequent to or in the absence of amplification. Also, it has been found that the relative magnitude of the probe-target transition increases as the amplicon length decreases. Accordingly, in still another example shorter amplicons may be used, illustratively 100 bp or shorter.

In the present examples, the 3' end of the unlabeled probe is phosphorylated to prevent polymerase extension during amplification. If desired, polymerase extension of the probe may be prevented by other means, including using a 2',3'-dideoxynucleotide, a 3'-deoxynucleotide, a 3'-3' linkage, other non-extendable termination such as the 3'-spacer C3 (Glen Research, Sterling, Va.), a biotin with an optional linker, or a minor-groove binder. Mismatching of two or more of the 3' terminal bases of the probe can also be used to prevent extension. Alternatively, the unlabeled probe with or without a blocked 3'-end could be added to nucleic acid sample mixtures that substantially lack polymerase activity.

Figure 20:
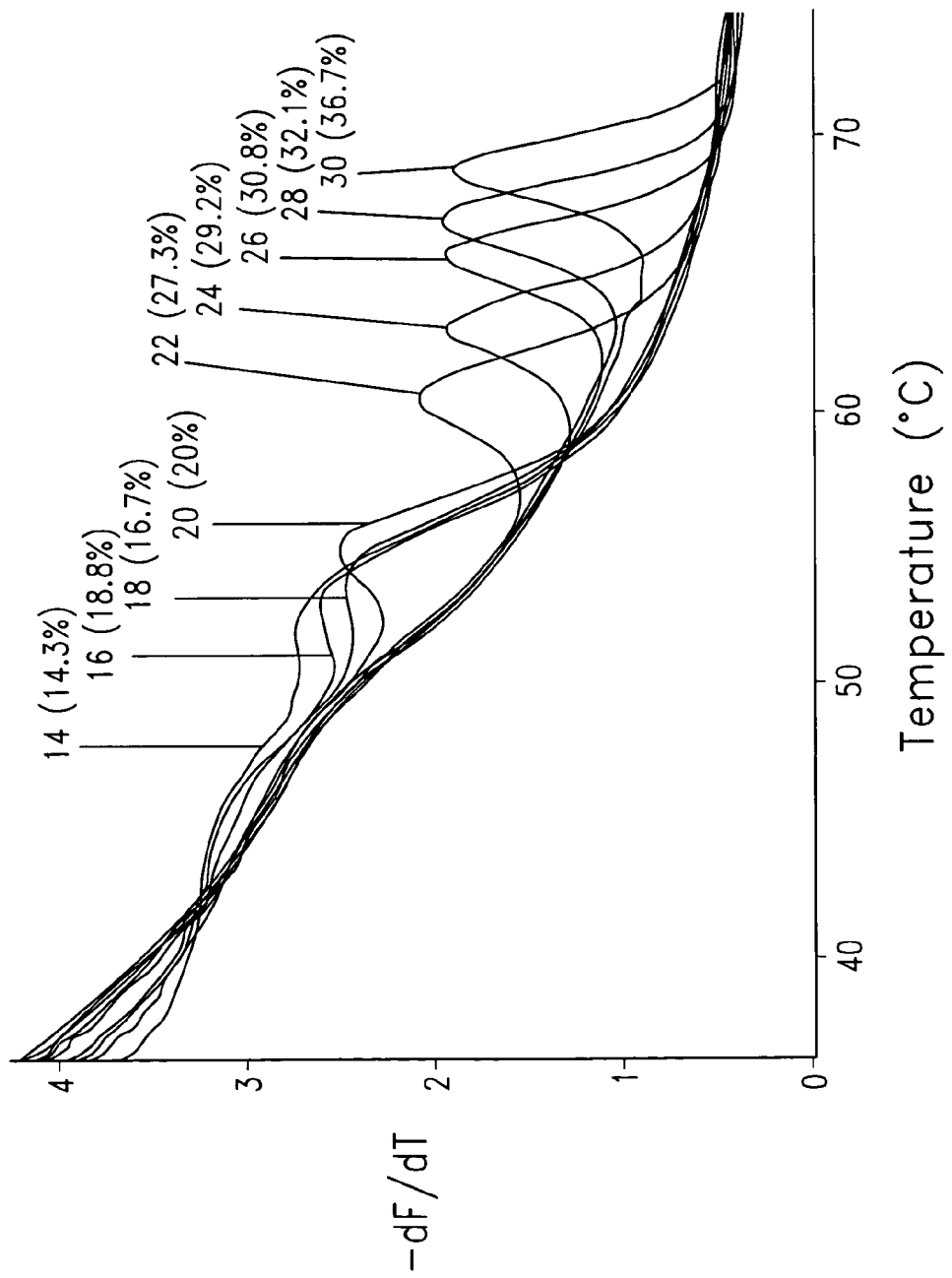
FIG. 20 is a derivative melting curve showing melting peaks for unlabeled probes ranging in length from 14 to 30 nucleotides.

Another consideration for successful genotyping is the length and GC content of the probe. As the binding mode of saturation dyes to dsDNA is not yet completely understood, several probe designs are tested. Table 5 and FIG. 20 show an optimization experiment using dye D6 in which probes differing in length from 14 to 30 bases with GC of 14 to 37% were examined. When the probe and target are completely complementary, melting peaks of probes as short as 14 bases were detected (FIG. 20). However, when there was a mismatch under the probe (which in this example is positioned in the middle of the probe), melting peaks were not observed for probes shorter than 22 bases (not shown), suggesting that dye D6 requires at least 10~11 bp of uninterrupted binding space under these conditions. In the design of probes, mismatches optionally can be positioned closer to the ends of the probe, as well as in the middle of the probe. A similar experiment was conducted with probe sequences of 100% AT and 100% GC hybridizing against synthetic complementary strands. The melting peaks of these probes were clearly detected when probes were 24 bases or longer (data not shown) with the 100% AT probe, and as short at 10 bases with the 100% GC probe. Results of melting analysis on the LightCycler®, HR-1, and the modified LightTyper® were all in agreement.

TABLE 5

| Length (bases) | Probe Sequence | GC % | SEQ ID NO. |
|---|---|---|---|
| 14 | caatgaa*tatttat | 14.3 | SEQ ID NO.25 |
| 16 | tcaatgaa*tatttatg | 18.8 | SEQ ID NO.26 |
| 18 | ttcaatgaa*tatttatga | 16.7 | SEQ ID NO.27 |
| 20 | attcaatgaa*tatttatgac | 20 | SEQ ID NO.28 |
| 22 | g attcaatgaa*tatttatgac g | 27.3 | SEQ ID NO.29 |
| 24 | gg attcaatgaa*tatttatgac ga | 29.2 | SEQ ID NO.30 |
| 26 | ggg attcaatgaa*tatttatgac gat | 30.8 | SEQ ID NO.31 |
| 28 | gggg attcaatgaa*tatttatgac gatt | 32.1 | SEQ ID NO.32 |
| 30 | ggggg attcaatgaa*tatttatgac gattc | 36.7 | SEQ ID NO.33 | a*denotes position complementary to the SNP on the amplicon

Figure 21A:
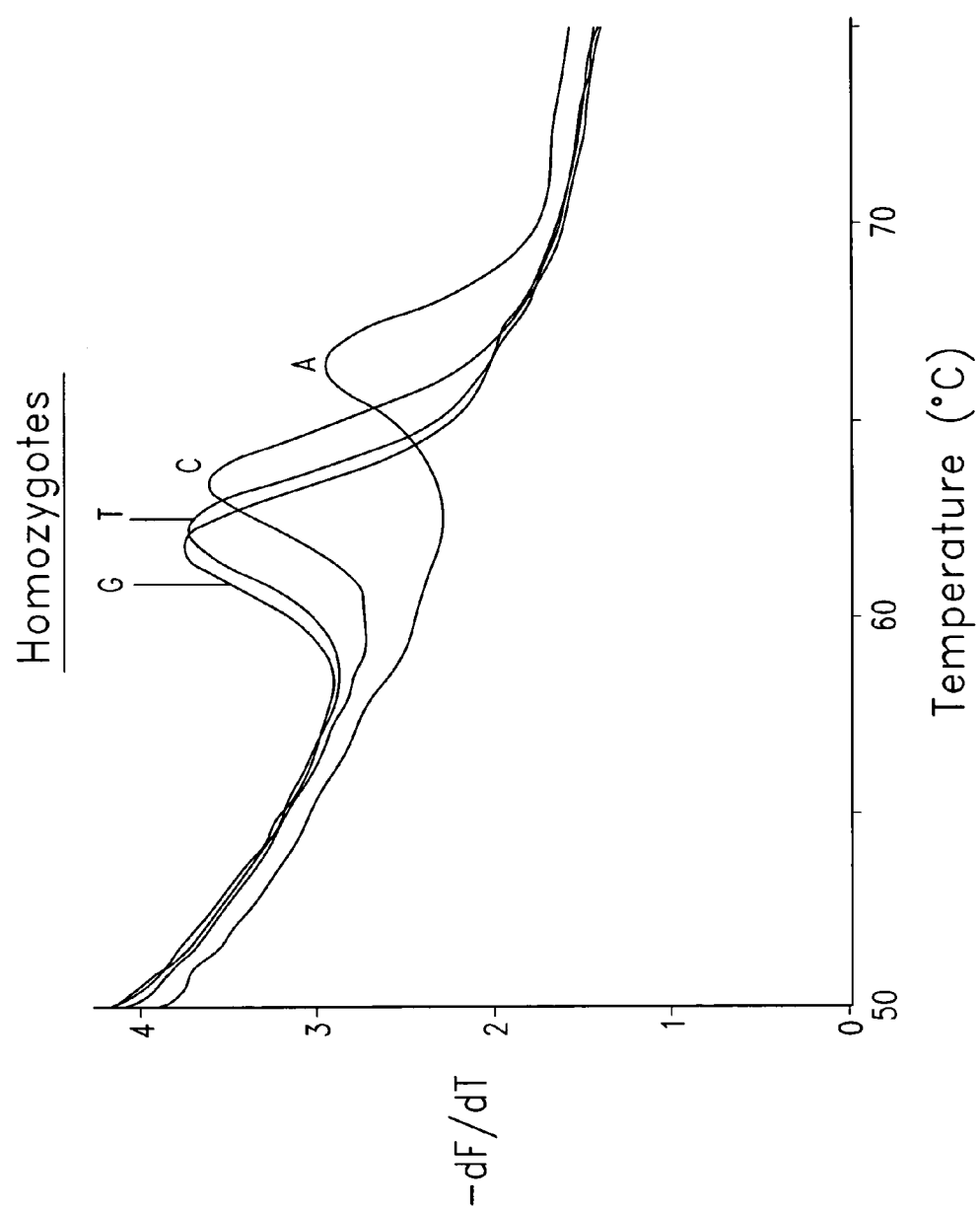
FIGS. 21A-D are derivative melting curves showing melting peaks in a test system for unlabeled probes.
Figure 21B:
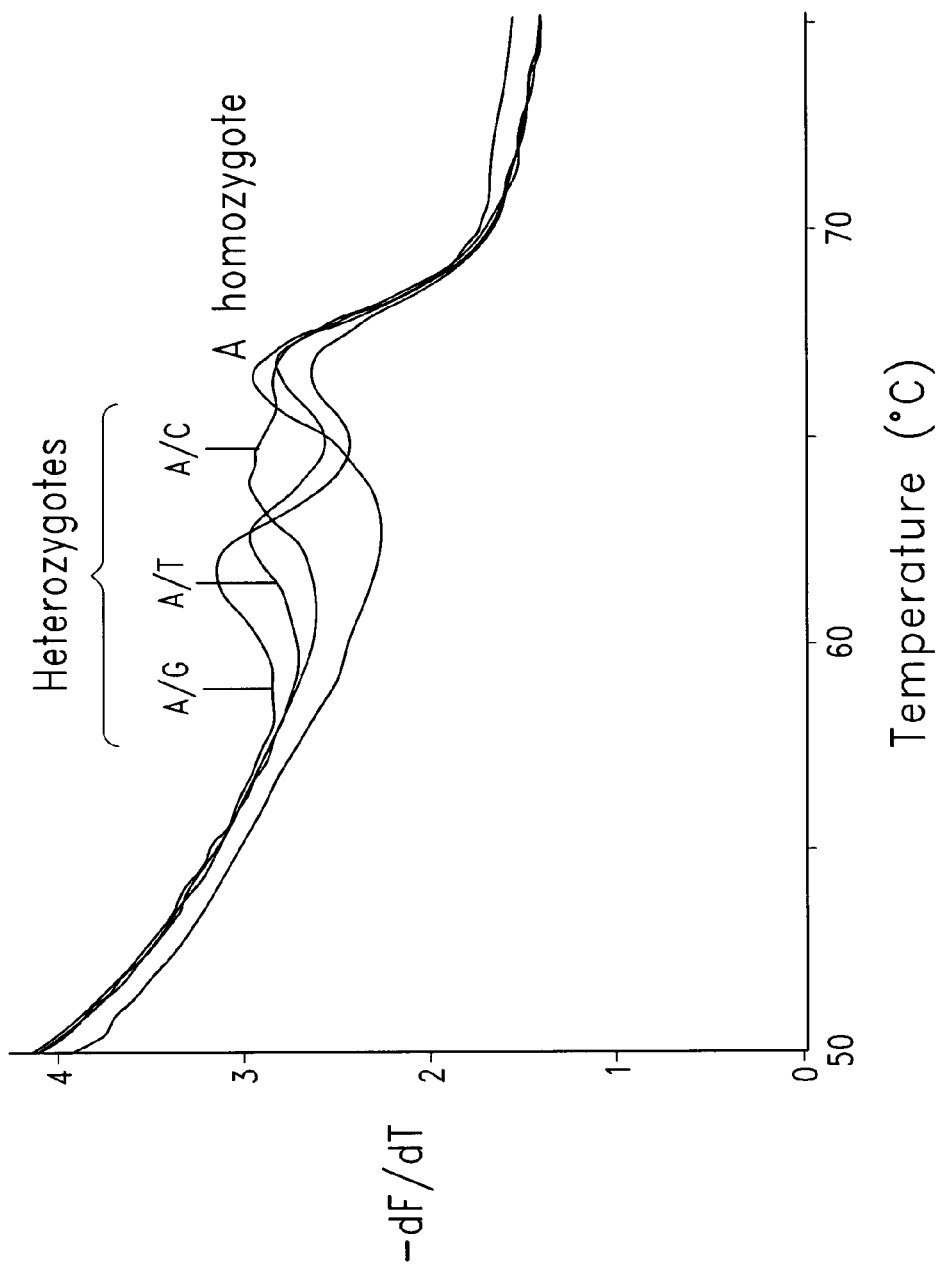
Figure 21C:
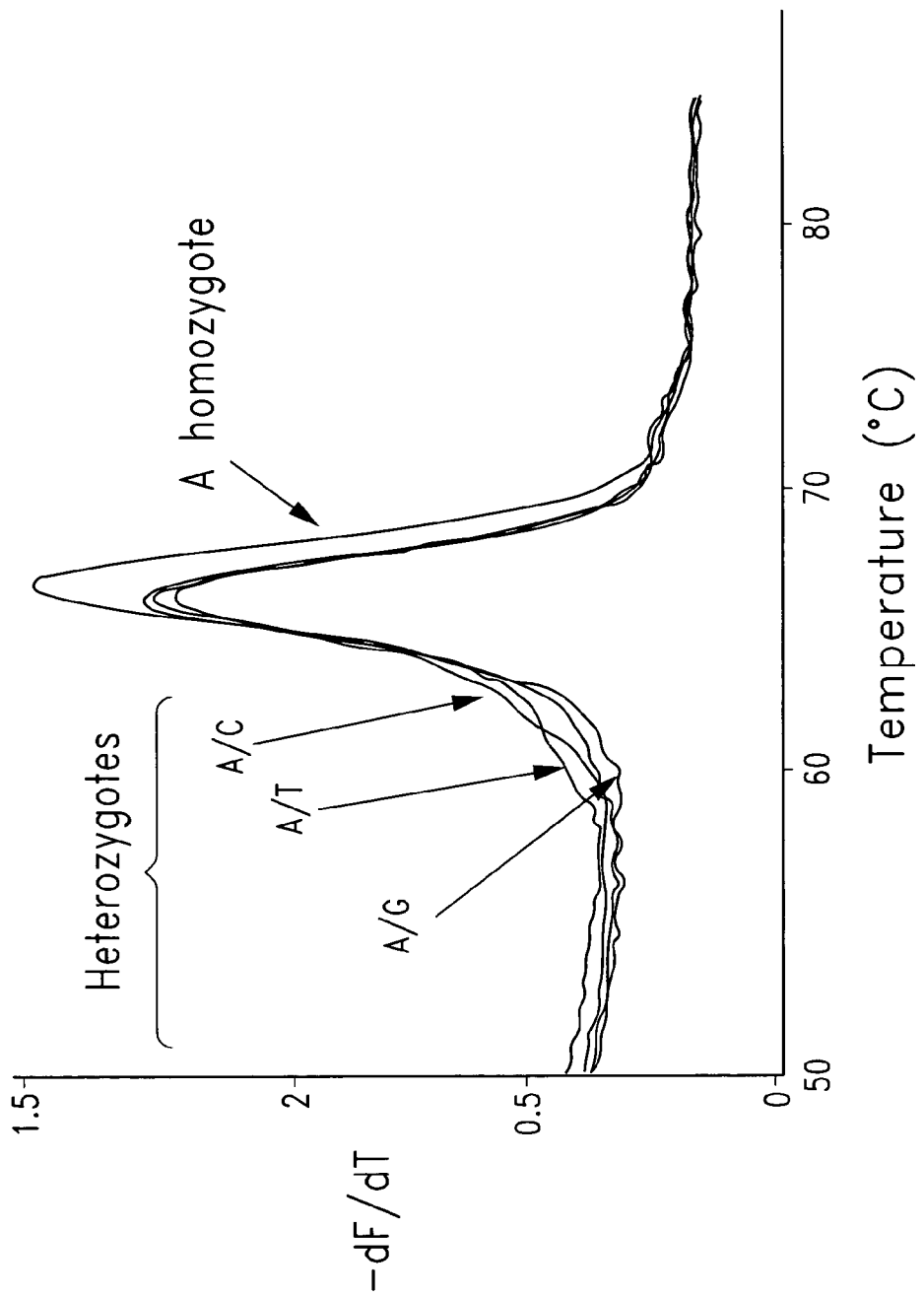
Figure 21D:
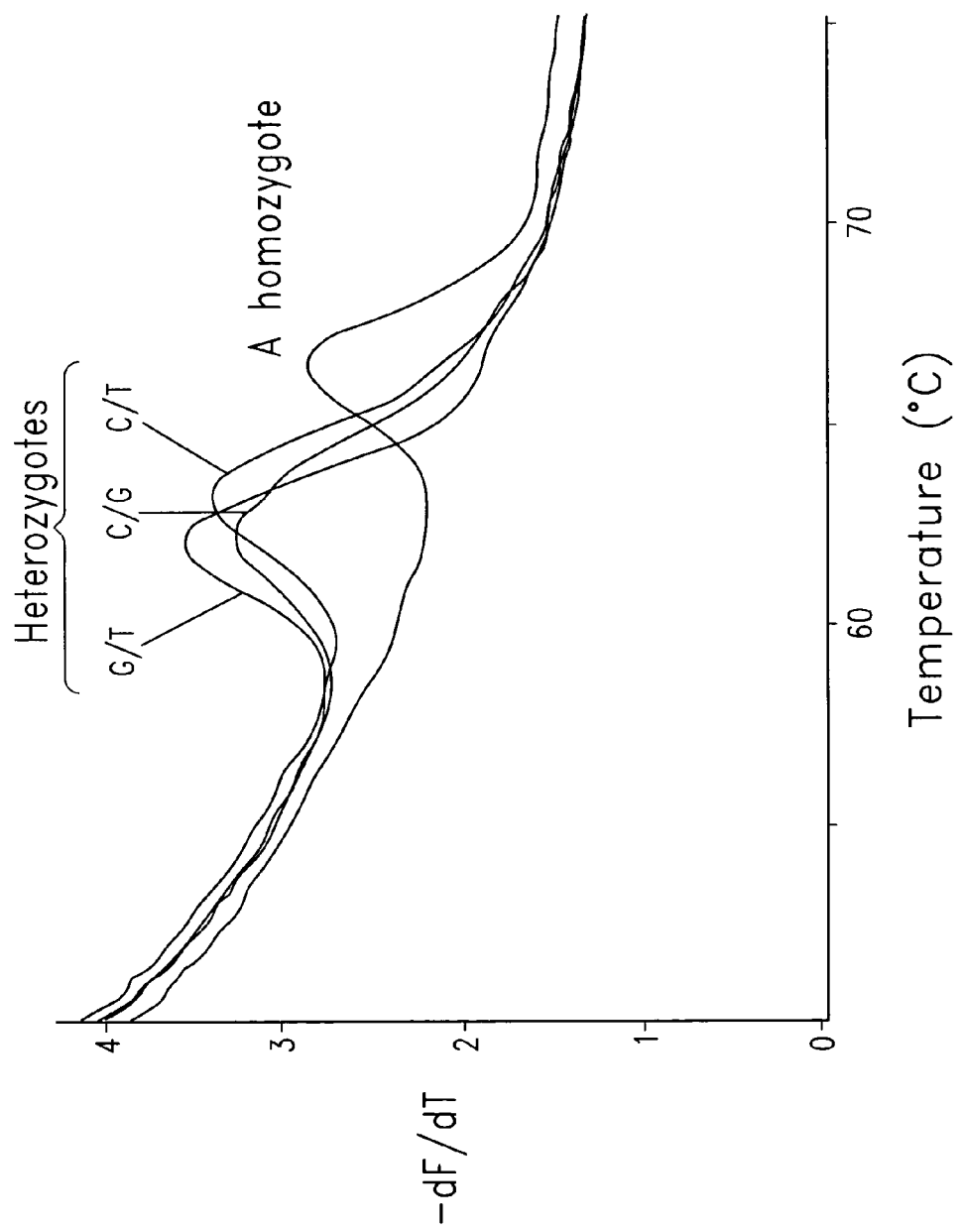

SNP typing was demonstrated with 28-base probes and templates that are either homozygous for A, C, G, and T at the alternative base position or are heterozygous for that position as follows: A/C, A/G, A/T, C/G, C/T, and G/T. FIGS. 21A-D show the melting curves generated by a probe that is fully complementary to the A homozygote (in this case the probe sequence is A and the sense strand is T). All homozygotes melted in a single transition (FIG. 3A). The A::T match is most stable with a Tm of 66.1° C. (predicted 64.0° C.), with the mismatches A::G (63.0° C., predicted 62.4° C.), A::A (61.9° C., predicted 60.7° C.) and A::C (61.4° C., predicted 60.8° C.) decreasing in order of stability. The Tm predictions did not account for the presence of the dye. As is the case with amplicon Tm (FIG. 10), the presence of dye usually increases probe Tm. Melting curves for all homozygotes are clearly separated and distinguishable (FIG. 21A). Heterozygous templates were separated into two groups: those in the first group had an allele fully complementary with the probe (A/T, A/C, A/G), and those in the other group did not (C/T, C/G, G/T). In the first group, the probe melting curve clearly displayed two peaks: the higher Tm peak matching with the homozygous A template, and the lower Tm peak characterizing the type of base mismatch (FIG. 21B). In the second group, melting curves showed only one melting peak, each of which was shifted to the left compared to the homozygous A template, and each of which is readily distinguishable from the others. (FIG. 21D). When the same test was done with SYBR Green I dye, the melting peaks of homozygous templates having a mismatch with the probe shifted to the left compared to the perfectly matched homozygous A template, but they were indistinguishable from each other. Heterozygous templates C/T, C/G, G/T were also shifted to the left, but not separated from each other. The melting curves of heterozygous templates A/C, A/G, and A/T could not be distinguished from the homozygous A template (FIG. 21C).

EXAMPLE 17

Cystic Fibrosis Genotyping with Unlabeled Probes and Saturating Dyes

Fragments of the CFTR gene exon 10 and 11 were amplified using samples obtained from Coriell Institute for Medical Research, and primers 5' ACATAGTTTCTTAC-CTCTTC (SEQ ID NO. 34, sense primer), and 5' ACT-TCTAATGATGATTATGGG (SEQ ID NO. 35, reverse primer) for exon 10, and primers 5' TGTGCCTTTCAAAT-TCAGATTG (SEQ ID NO. 36, sense primer) and 5' CAG-CAAATGCTTGCTAGACC (SEQ ID NO. 37, reverse primer) for exon 11. The probe for exon 10, which hybridizes over the F508del mutation, was 5' TAAAGAAAATAT-CATCTTTGGTGTTTCCTA (SEQ ID NO. 38). Two probes were used for the detection of the G542X mutation in exon 11 (5' CAATATAGTTCTTNGAGAAGGTGGAATC, SEQ ID NO. 39), where N is either G or T. All probes were phosphorylated at the 3' end. PCR was performed asymmetrically, using a primer ratio of 10:1 (0.5 μM sense; 0.05 μM reverse). Other reagents for PCR were essentially the same as in Example 16, except 50 ng of genomic DNA was used as template. Cycle conditions were 95° C. for 10 s and then 45 cycles of 95° C. for 0 s, 52° C. for 0 s and 72° C. for 10 s Melting curve analysis on the LightCycler® was performed as in Example 16. Table 6 lists the various deletions detected by the probes.

TABLE 6

| Mutation | Nucleotide position | Amino acid change | exon |
|---|---|---|---|
| I506V | A or G at 1648 | Ile or Val at 506 | 10 |
| I507 del | deletion of 3 bp between 1648 and 1653 | deletion of Ile506 or Ile507 | 10 |
| F508del | deletion of 3 bp between 1652 and 1655 | deletion of Phe at 508 | 10 |
| F508C | T or G at 1655 | Phe or Cys at 508 | 10 |
| G542X | G to T at 1756 | Gly to Stop at 542 | 11 |

Figure 22A:
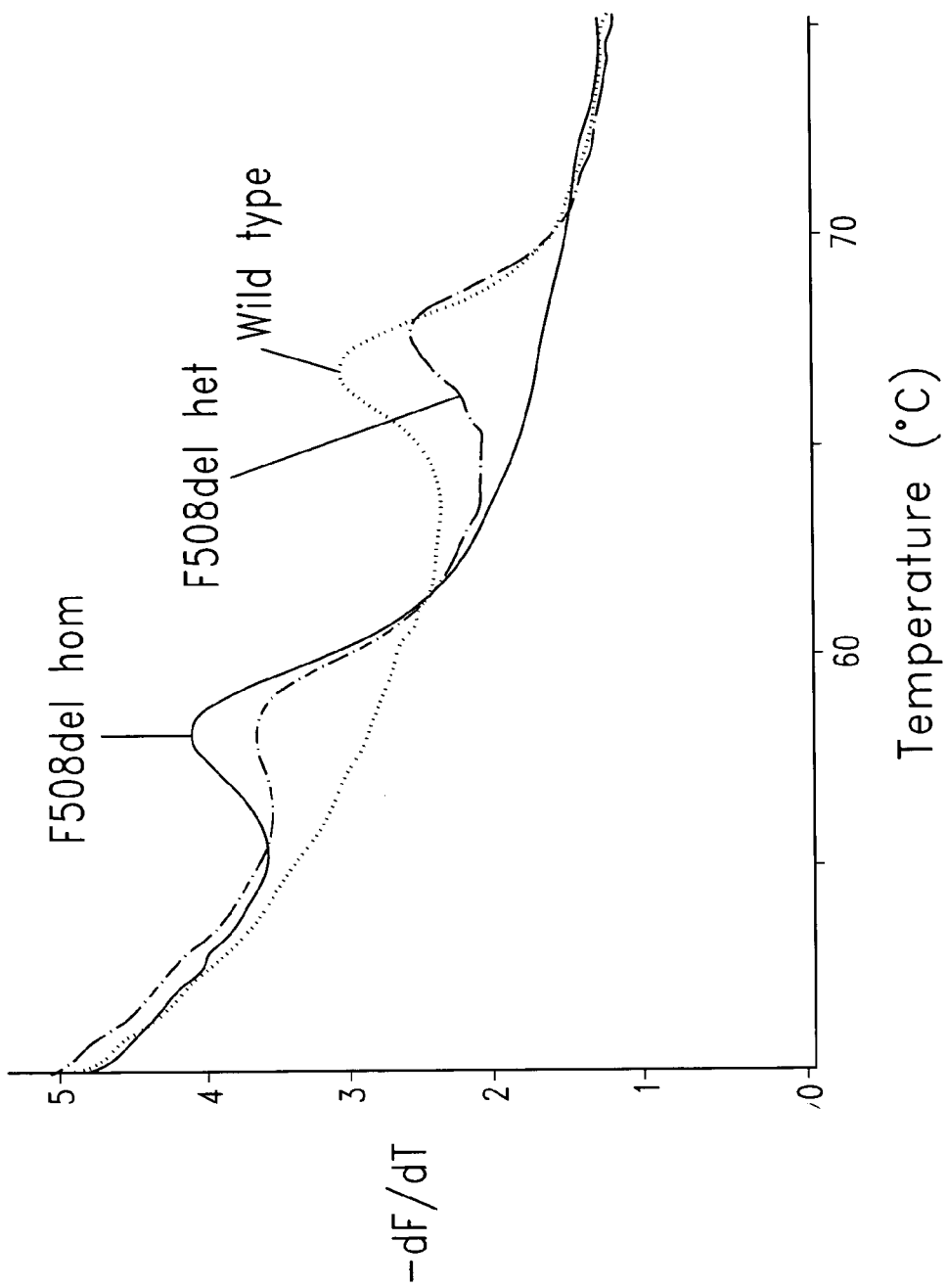
FIGS. 22A-B are derivative melting curves showing melting peaks for various cystic fibrosis mutations using an unlabeled probe.
Figure 22B:
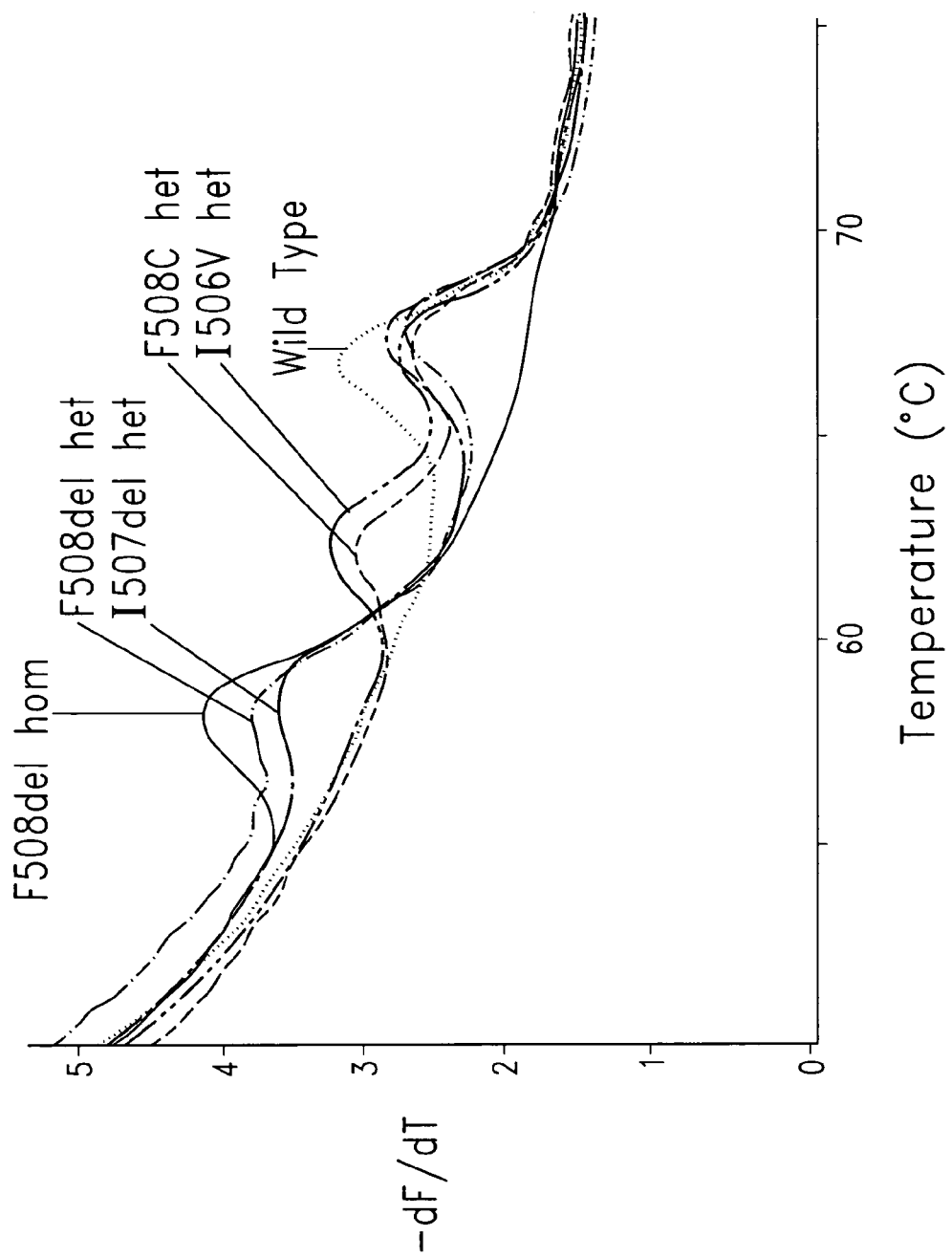

The F508del mutation was chosen as an example of a small (3 bp) deletion. The probe contained a 28 base wild type sequence. FIG. 22A shows that the Tm of the homozygous F508del shifted about 10° C. below the wild type. The melting curve of the heterozygous F508del showed two melting peaks: one at the same temperature as the wild type and the other the same as the homozygous F508del. FIG. 22B shows an overlay of three additional heterozygous mutations found in this locus, F508C, I506V, and I507 del.

Figure 23:
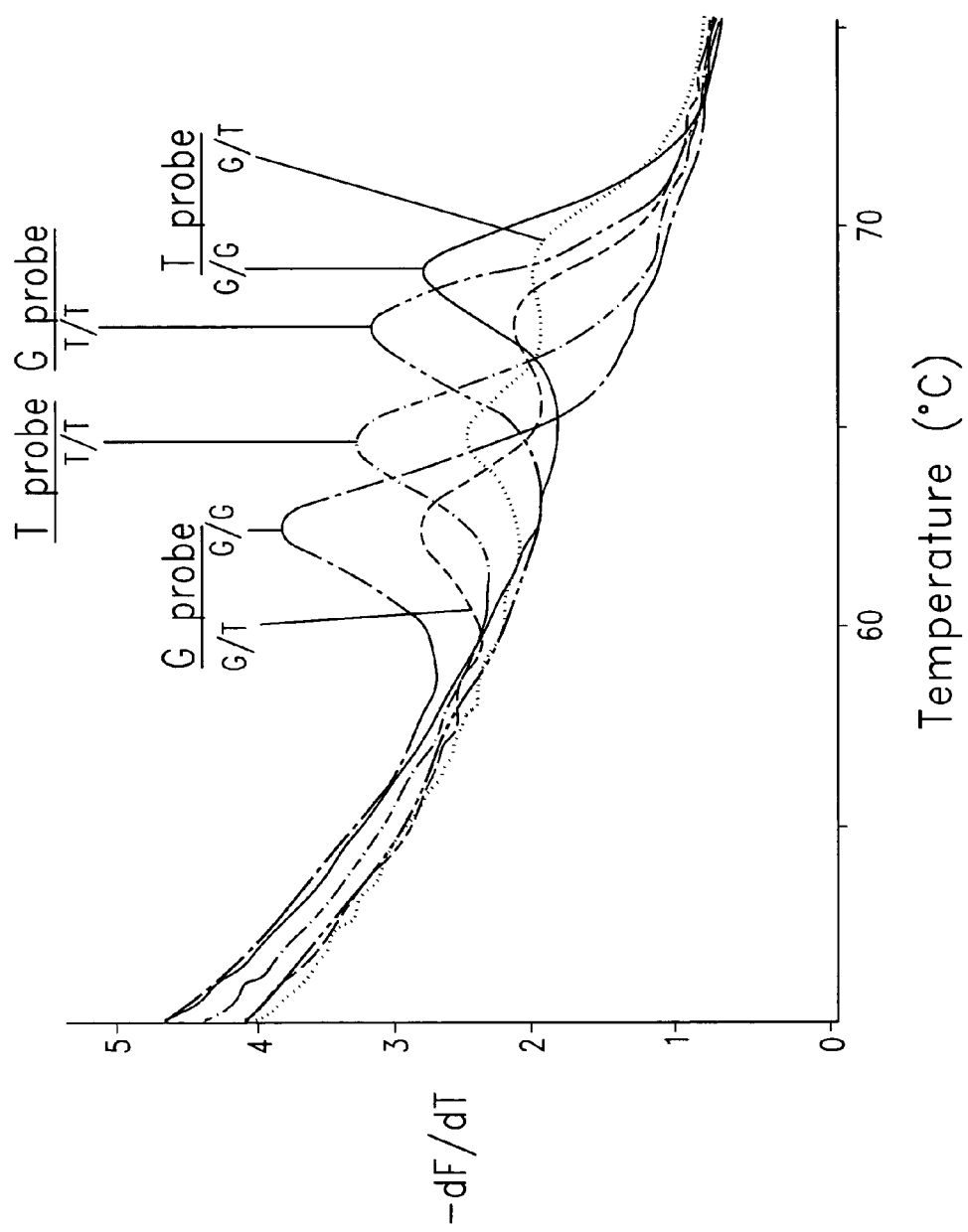
FIG. 23 is a derivative melting curve showing melting peaks for a cystic fibrosis SNP mutation using two different unlabeled probes.

The G542X mutation is a single base mutation in which the wild type G changes to T. The 28 base wild type probe G and mutation probe T were used to type G542X homozygous (T/T) and heterozygous (G/T) mutations without sequencing (FIG. 23).

EXAMPLE 18

Genotyping by Multiple Unlabeled Probes and a Saturating Dye

Figure 24:
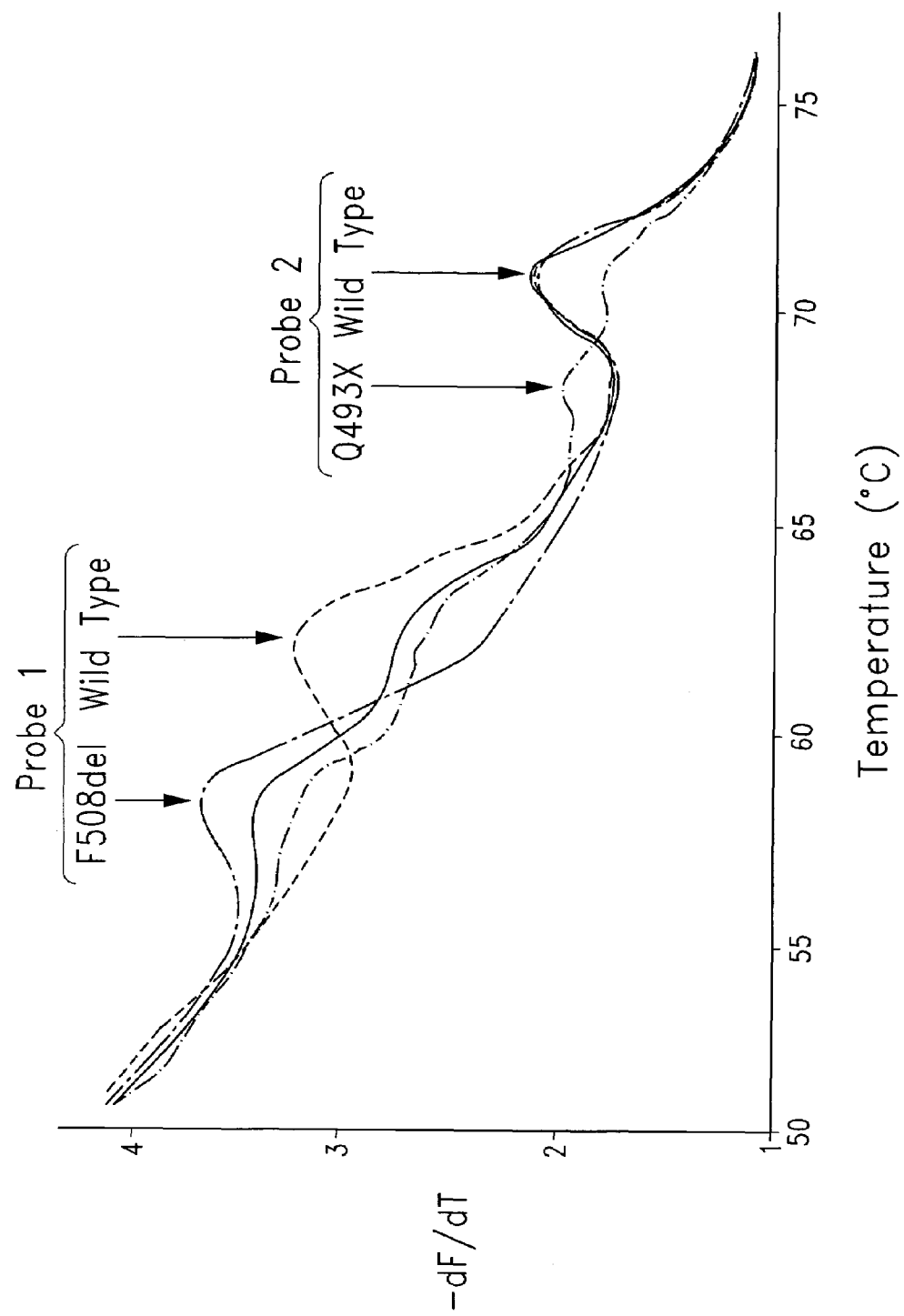
FIG. 24 is a derivative melting curve showing melting peaks for cystic fibrosis mutations F508del and Q493V using two unlabeled probes in the same reaction.

Melting analysis using an unlabeled probe with a saturating dye enables genotyping of one or more sequence variants under the probe. The use of multiple unlabeled probes enables simultaneous genotyping of sequence variants in multiple sequence segments. Probes can be designed to hybridize with multiple sequence segments on one DNA fragment, or with sequence segments on multiple DNA fragments. Illustratively, where multiple probes are used with a single target DNA fragment, the probes do not need to overlap to provide information on sequence variation. In an illustrative example, a 210 bp fragment of the cystic fibrosis gene was asymmetrically amplified in the presence of 20 µM of dye D6 or N7, using two primers described earlier (the sense primer SEQ ID NO. 34 and the reverse primer SEQ ID NO.35 at 0.5 µM and 0.05 µM, respectively). In this 210 bp fragment, the presence or absence of two mutations, F508 del and Q493V, were tested by two unlabeled probes: Probe 1: ATCTTTGGTGTTTCCTATGATG (SEQ ID NO. 48; underlined are the three bases that become deleted in the F508del mutation) and Probe 2: CTCAGTTTTCCTGGATTATGCCTGGC (SEQ ID NO. 49: underlined is the base that mutates into T in Q493V). The 3' ends of both probes were phosphorylated. The melting temperatures of the matched or mismatched probes were kept below 72° C. to allow sufficient separation from the amplicon melting signature. Melting analysis was conducted with the LightCycler®, HR-1, and modified LightTyper® instruments, as in Example 16. The melting data from all three instruments correctly genotyped four samples: wild type, F508del homozygote, F508del heterozygote, and F508del/Q493V compound heterozygote. FIG. 24 shows the melting profile with dye N7. Very similar results were obtained with dye D6.

EXAMPLE 19

Simultaneous Mutation Scanning and Genotyping

Testing for many genetic disorders can be difficult because the causative mutations are often scattered all over the gene. Simultaneous mutation scanning and genotyping can be used to detect these alterations. Illustratively, for any particular gene of interest, each exon is amplified using primers outside of common splice sites. If high frequency sequence variants are known, an unlabeled probe may be included to genotype the site, or an additional set of primers may be use to amplify this smaller locus. Mutation scanning and genotyping of specific sites can be performed in separate reactions, or when scanning is positive, the probe subsequently can be added to the tube and melting analysis repeated for genotyping. Preferably, scanning and genotyping are done simultaneously by analyzing both full-length amplicon and smaller locus duplexes in the same melting curve analysis. Because of the different sizes of the full-length amplicon and the smaller locus, it is expected that melting peaks for the full-length amplicon would be at higher temperatures than for the smaller locus.

The average gene covers about 27 kb, but only about 1,300 bases code for amino acids. On average, there are about 9 exons per gene with a mean length of about 150 bp. Of the sequence alterations that cause disease, about 70% are SNPs, with 49% missense, 11% nonsense, 9% splicing and <1% regulatory mutations. Small insertions/deletions make up 23% of disease-causing mutations. The remaining 7% are caused by large insertions or deletions, repeats, rearrangements, or compound sequence alterations. Some sequence alterations do not affect gene function, for example silent SNPs that result in the same amino acid sequence. Additional examples include SNPs and in-frame insertions or deletions that change the amino acid sequence but do not alter protein function. Most SNPs and repeats within introns do not cause disease, except for splicing and regulatory mutations. With the exception of large deletions and sequence alterations deep within introns, disease-causing mutations can be identified by PCR using primers within introns that flank each exon. The primers are placed outside of likely splice site mutations. If the sequence alteration is not amplified, it will not be detected by any method, including sequencing.

High-resolution melting analysis using the dyes of the present disclosure becomes more difficult as the amplicon size increases. Optionally, to maintain scanning sensitivity near 100%, exons greater than 400-500 bases can be scanned with more than one amplicon. Illustratively, common thermal cycling parameters are used so that all exons can be amplified at once.

Simultaneously with mutation scanning, common mutations and polymorphisms can be genotyped by including one or more unlabeled oligonucleotide probes or by selectively amplifying a smaller amplicon using one or more additional sets of primers. Amplification of both the larger and the smaller amplicon can be performed simultaneously, or by a biphasic PCR which amplifies the larger amplicon in the first phase, and the smaller amplicon(s) in the second phase. This biphasic PCR can be achieved by designing the Tm and amount of each of the primers in a way that, by adjusting the annealing temperatures of the two phases, preferentially amplification of the different amplicons occur. When the signal from the larger amplicon is expected to overwhelm or mask the signal from the shorter amplicon, this biphasic technique can be used to adjust the final amount of each of the amplicons to circumvent such a problem. When one or more oligonucleotide probes are used, amplification of the larger amplicon by mild asymmetric PCR can be used, illustratively having about a 10:1 primer ratio.

Figure 25A:
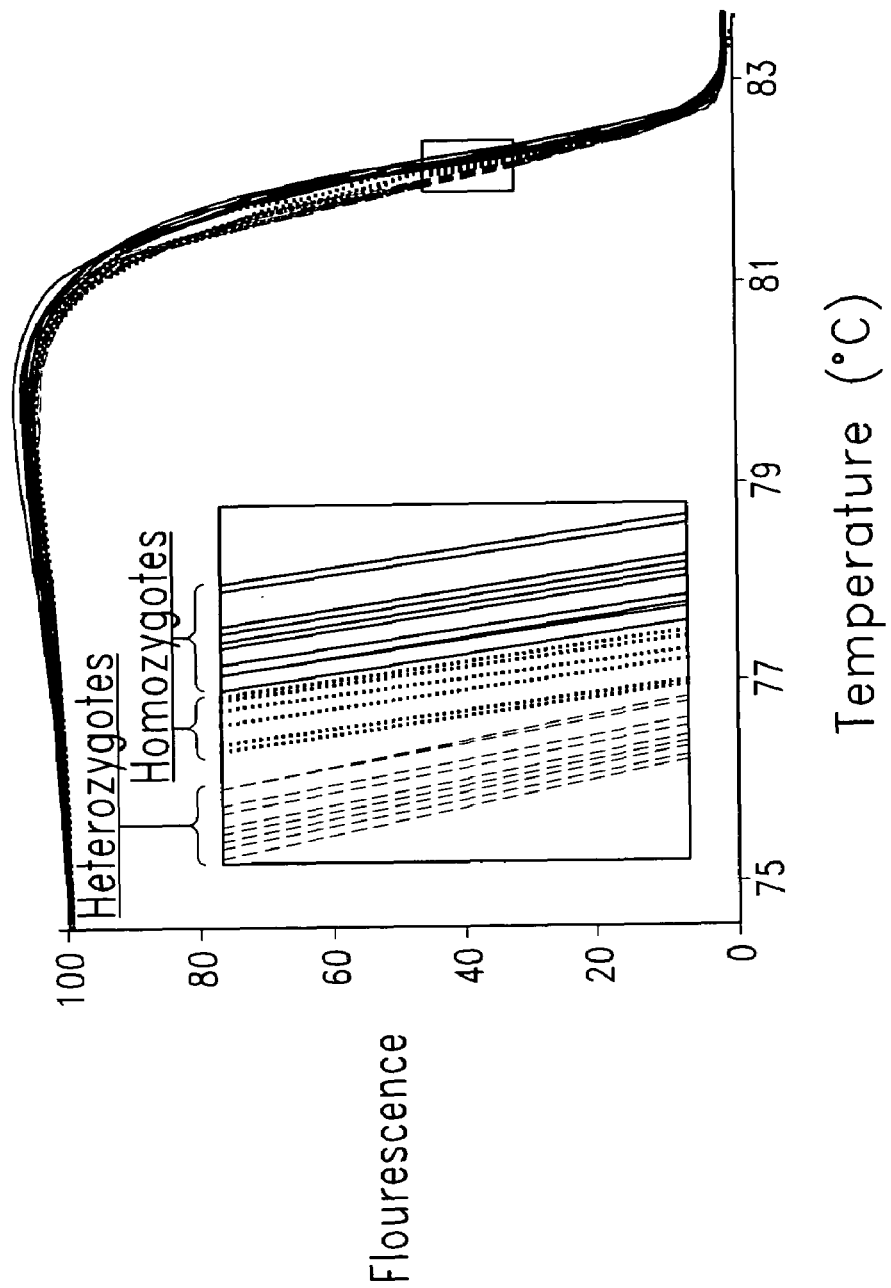
FIG. 25A shows a fluorescence versus temperature plot for data between 75° C. and 83° C. (the amplicon melting profile). The inset shows a magnified view of the portion of the curve indicated by the square.
Figure 25B:
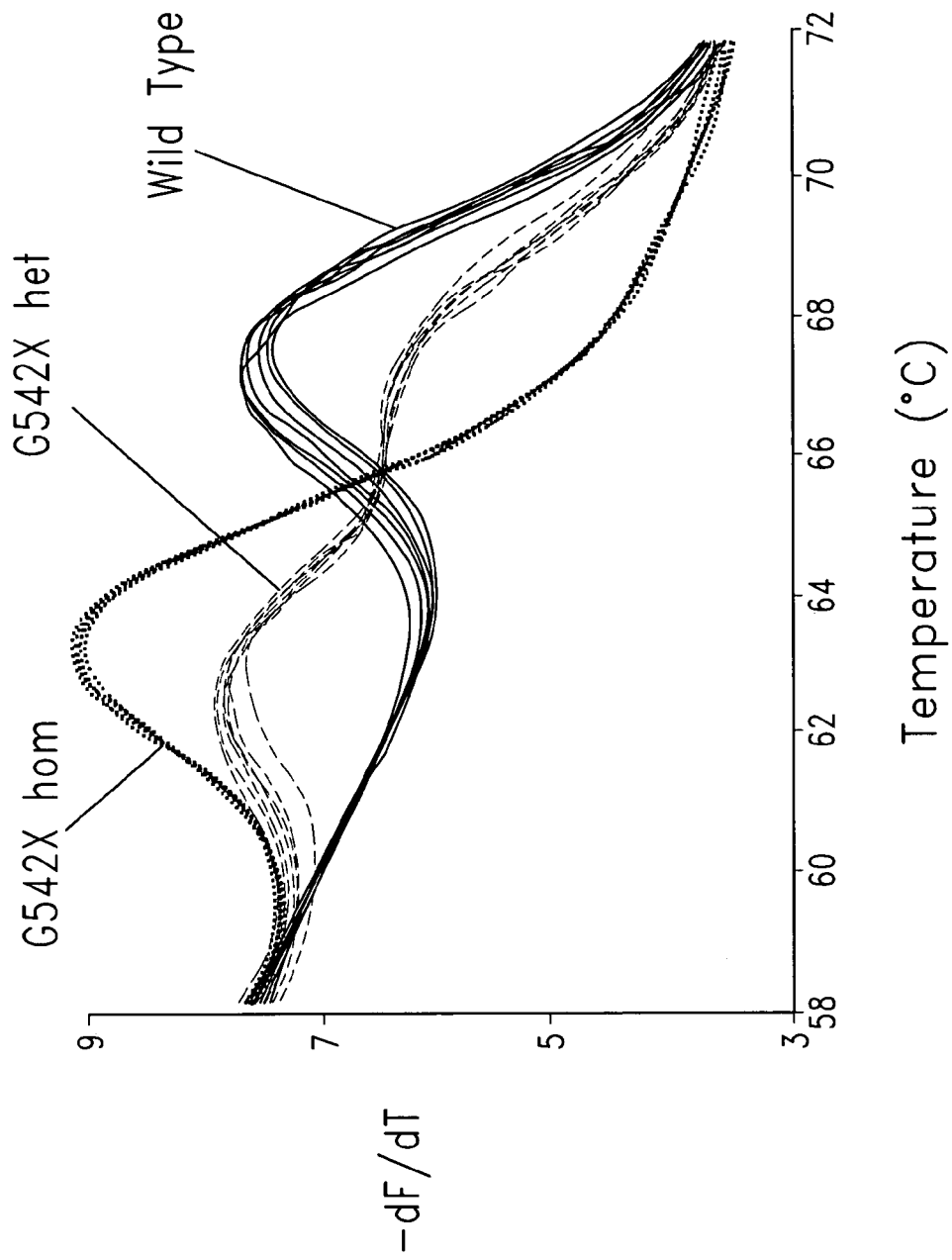
FIG. 25B shows a derivative plot of data between 58° C. and 72° C. (the probe melting profile), ___wild type; ...G542X homozygote; _._G542X heterozygote.

An illustrative example of using a single melting procedure for simultaneously scanning for mutations in the amplicon and genotyping by a probe was conducted as follows: The cystic fibrosis exon 11 fragment was amplified from ten wild type and twenty unknown specimens in the presence of the wild type probe G and dye D6 according to the method described in Example 17. The amplified samples were then melted on the modified LightTyper instrument (Example 16) using a ramp rate of 0.1° C./s between 40° C. and 90° C. FIG. 25A shows the amplicon portion of the melting curve (75-83° C.). Ten of the samples had slightly left-shifted curves that were clearly distinct from the ten wild type samples. These were suspected of carrying a heterozygous mutation somewhere in the amplicon. The rest of the curves followed the predicted shape of homozygous samples. However, the curves of the remaining ten unknown samples did not overlap with the wild type curves, and therefore, the majority of these were flagged as possible sequence variants as well. FIG. 25B shows the probe portion of the melting curve (58-72° C.) plotted as the negative derivative. Here, each of the thirty samples were unambiguously genotyped.

EXAMPLE 20

Monitoring Fluorescence During Amplification Using Unlabeled Probes

When fluorescence from a dsDNA-binding dye is monitored during PCR, it is possible to observe, cycle by cycle, the generation of a specific target nucleic acid sequence as defined by hybridization of the target nucleic acid to an unlabeled probe. The amount of target sequence at each PCR cycle depends on its initial amount in the original sample. Therefore, quantification is possible. As illustrated, the fluorescence signals from the amplicon and other dsDNA are separated from the probe-specific signal. This is achieved by monitoring fluorescence at a plurality of temperature points comprising before and within the probe melting transition, during at least two cycles in an amplification reaction.

Figure 26:
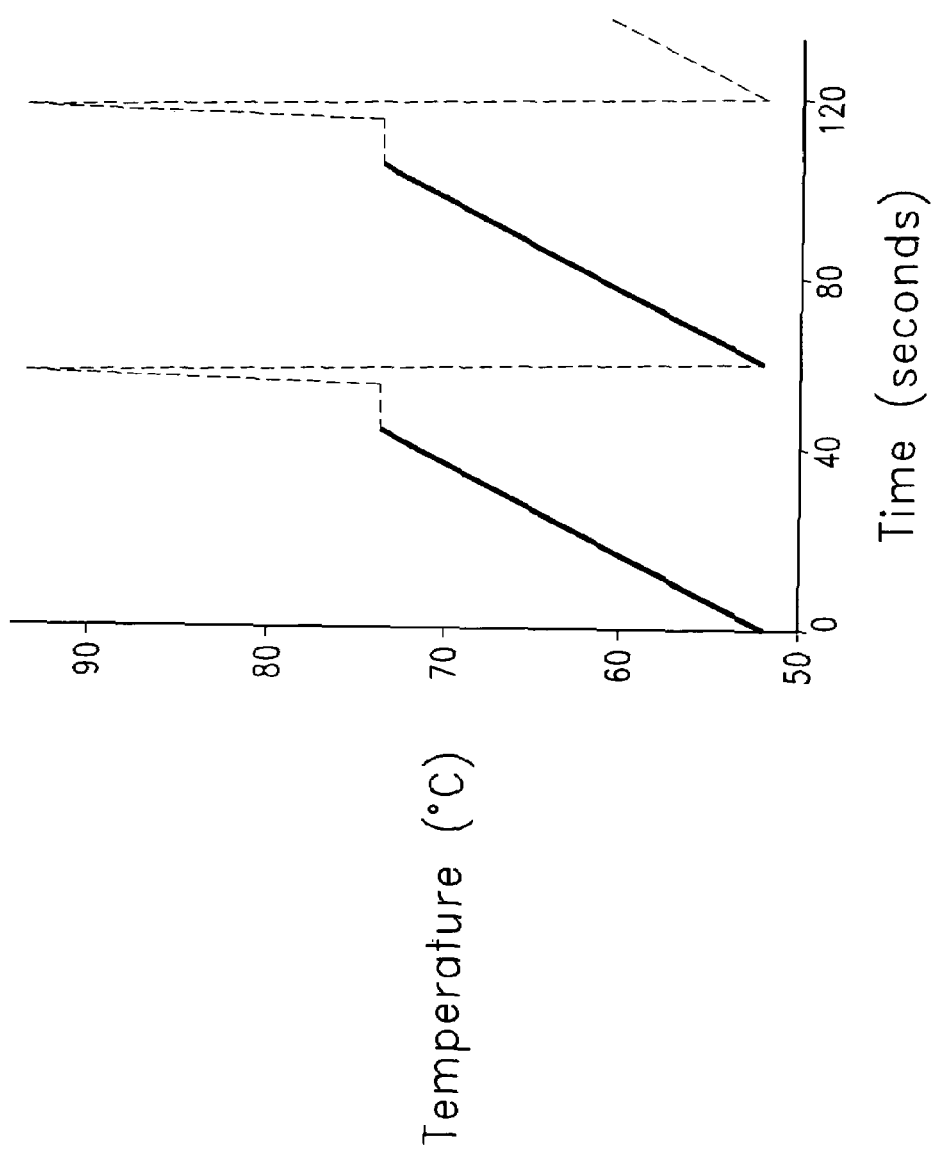
FIG. 26 illustrates PCR parameters programmed on the LightCycler for monitoring unlabeled probe/target duplex melting during each amplification cycle. Two PCR cycles are shown. Fluorescence was monitored continuously between annealing and extension (indicated by the solid line) for each cycle.
Figure 28A:
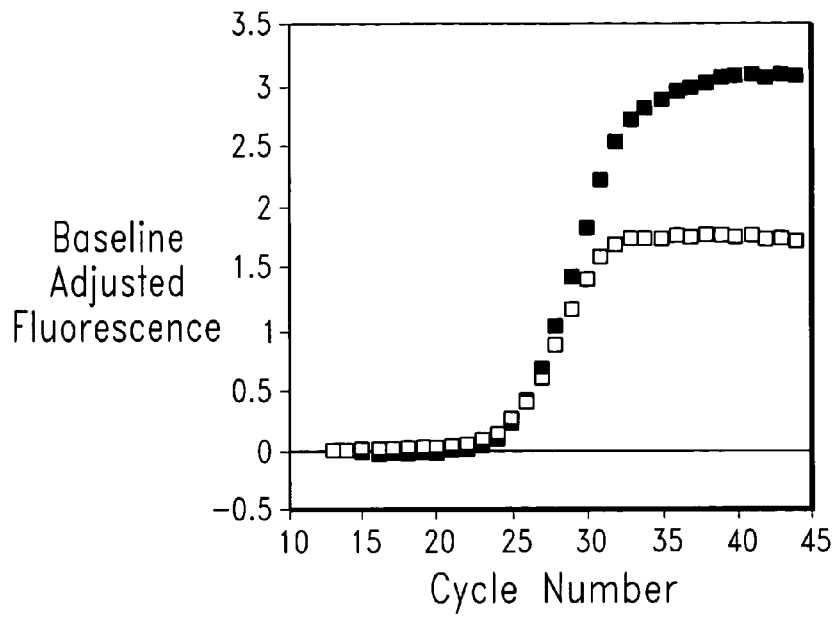
FIG. 28A shows the cycle number versus fluorescence plot of data acquired at 61° C. (reflecting the amount of total dsDNA in the reaction, ■) and at 73° C. (reflecting the amount of amplicon, □).

In an illustrative example, a 300 bp fragment of the DNA Toolbox plasmid (Example 5) was amplified in the presence of a 28-bp probe (Table 5, SEQ ID NO. 32) using reagents described in Example 16, except that the template DNA was $10^5$ copies/10 µl, unless otherwise stated, MgCl$_2$ was used at 2 mM, and dye N7 was used instead of D6. A primer ratio of 10:1 was used. The probe and the plasmid were matched in sequence (i.e. no mismatch under the probe). Amplification was performed in the LightCycler using the following programmed parameters for 45 cycles: 95° C. for 0 s, cooling at −20° C./s, 52° C. for 0 s, heating at 0.5° C./s, 74° C. for 8 s, heating at 20° C./s. Fluorescence was continuously monitored between 52° C. and 74° C. as shown in FIG. 26 during each cycle of PCR. The data files were then imported into a custom software, essentially as described in U.S. Pat. No. 6,174,670, herein incorporated by reference, to analyze the multiple fluorescence data obtained each cycle. The quality of amplification was assessed by the traditional method of plotting the fluorescence value at one temperature each cycle, such as 61° C. at which the amount of all dsDNA can be observed (FIG. 28A closed square), or 73° C. at which only the amount of double-stranded amplicon is observed (FIG. 28A open square).

When a temperature range specific for observing probe melting was selected for each cycle (in this case 62~72° C.), the resulting fluorescence curves (plotted as the negative derivative in FIG. 27) showed that with increasing cycle number, the melting peak of the probe grew larger. One method to express the correlation between cycle number and the amount of probe:target specific signal is to plot the difference in derivative value at the probe Tm (in this case at 66.5° C.) and just before the probe's melting transition (at 64° C.). The resulting plot is shown in FIG. 28B (open triangle) showing a positive correlation between probe: target signal and cycle number. The two temperature points can be predetermined, or chosen visually from the derivative curves, or obtained from the second derivative curves where the second derivative equals zero. It is contemplated that, once such plots are established, these plots can be used for quantification of initial template in a sample.

Figure 27:
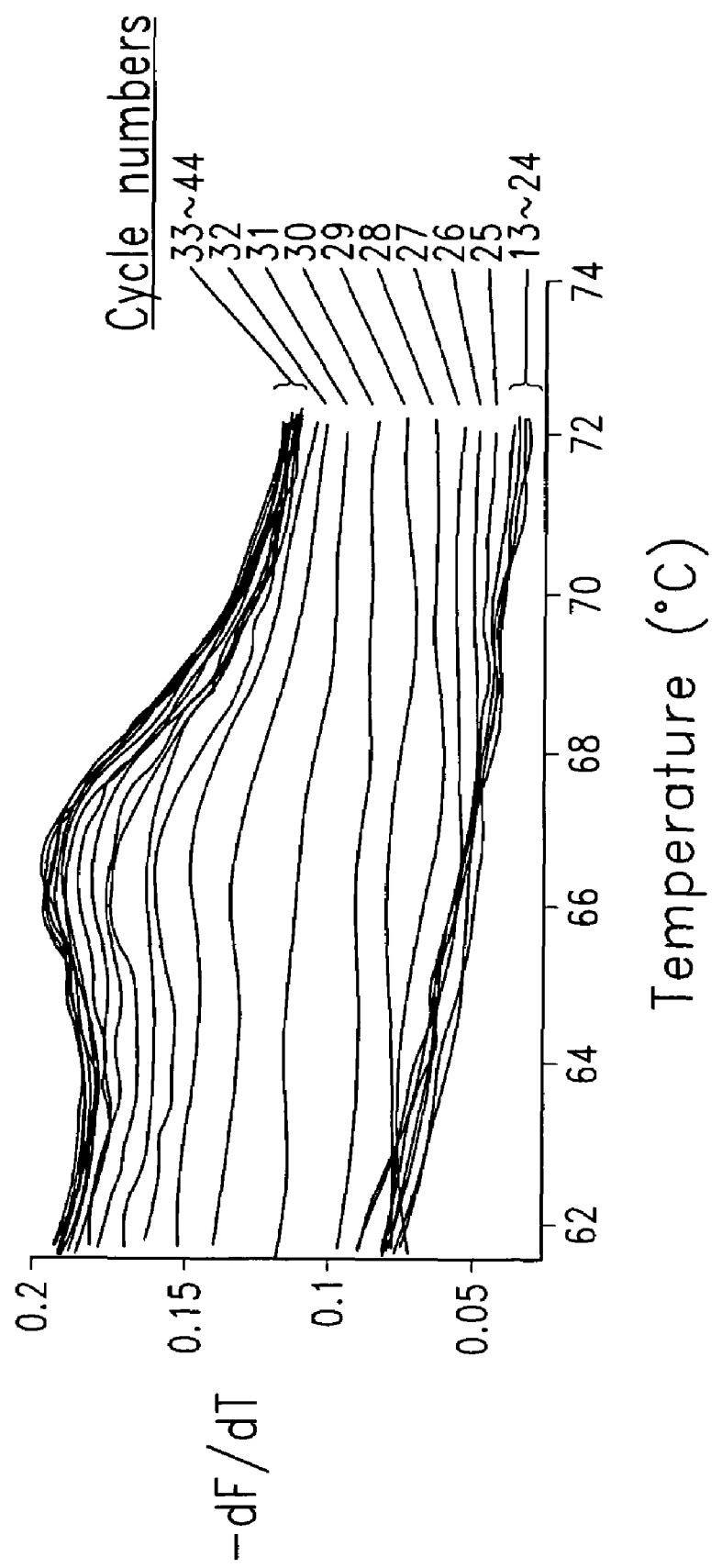
FIG. 27 shows derivative melting curves obtained during each cycle of PCR using an unlabeled probe and dye N7. The peak height increases with cycle number. The initial concentration of template DNA in this sample was $10^5$ copies/10 μl.
Figure 28B:
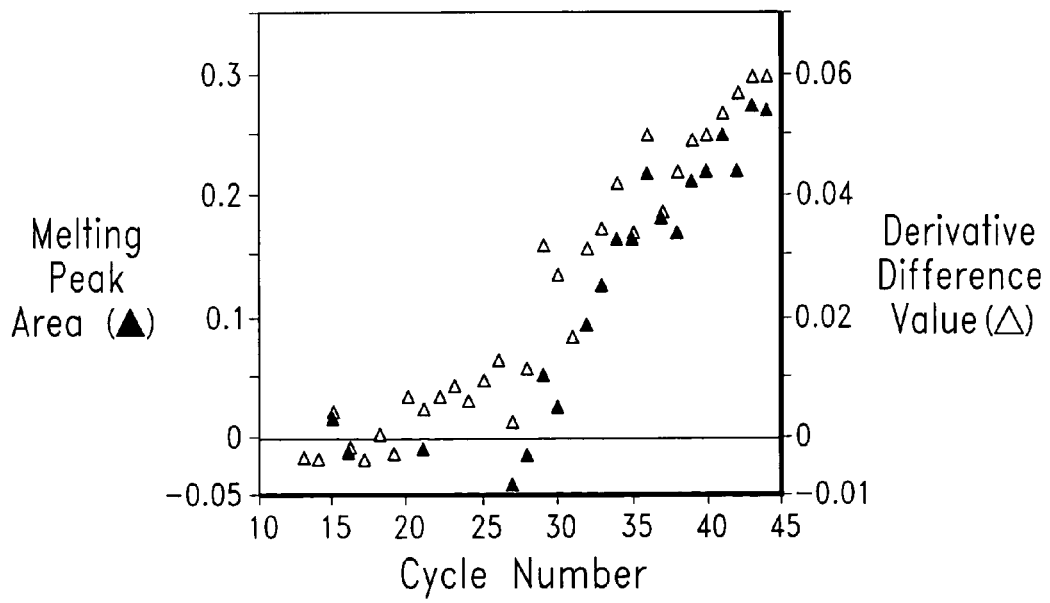
FIG. 28B shows the cycle number plotted against melting peak area (▲) and against the difference between the top of the melting peak and just before the melting transition calculated from the derivative data (Δ).
Figure 28C:
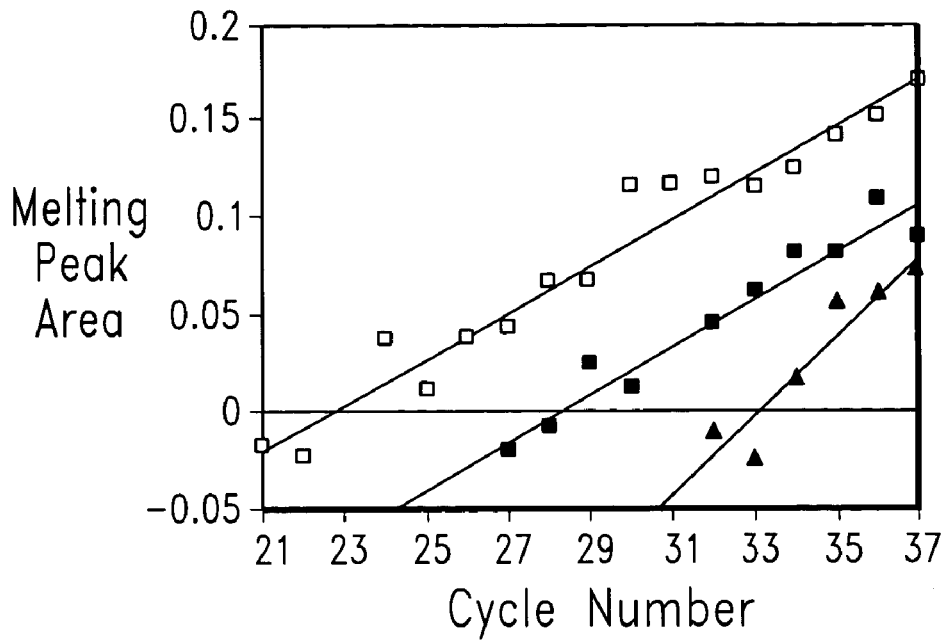
FIG. 28C shows cycle number versus melting peak area plot for three different initial template concentrations (▲- $10^4$ copies/10 μl; ■- $10^5$ copies/10 μl; □- $10^6$ copies/10 μl).
Figure 28D:
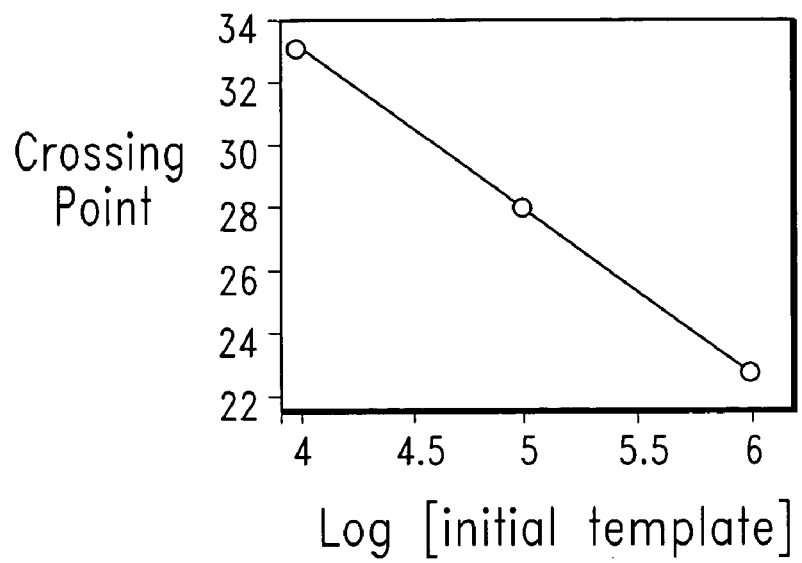
FIG. 28D shows the log of the initial template concentration plotted against the crossing point of each sample that was derived from FIG. 28C.
Figure 29:
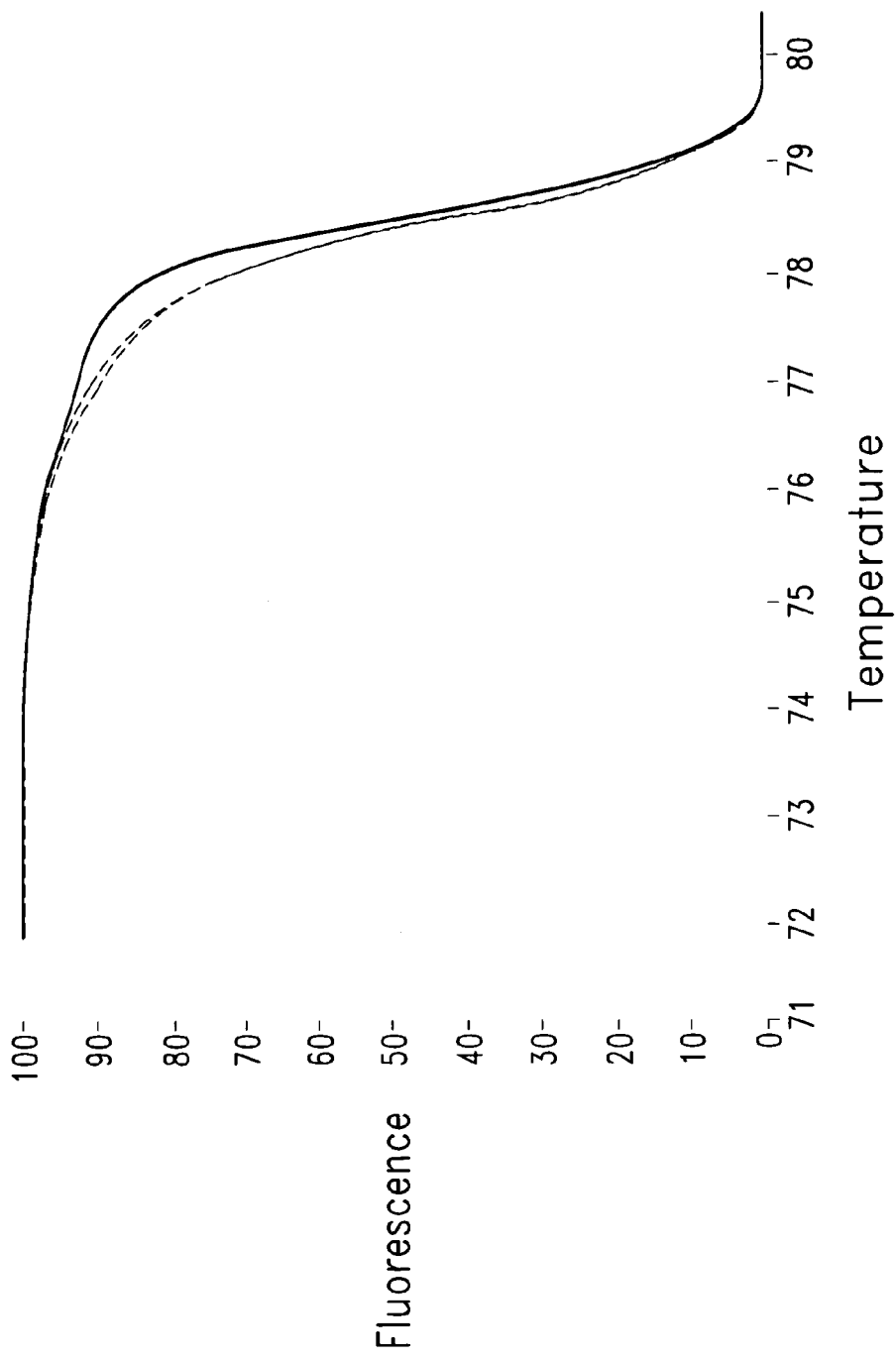
FIGS. 29-32 show melting curves for genotyping various gastrointestinal stromal tumor (GIST) mutations, each comparing to normal wild type amplicons.
Figure 30:
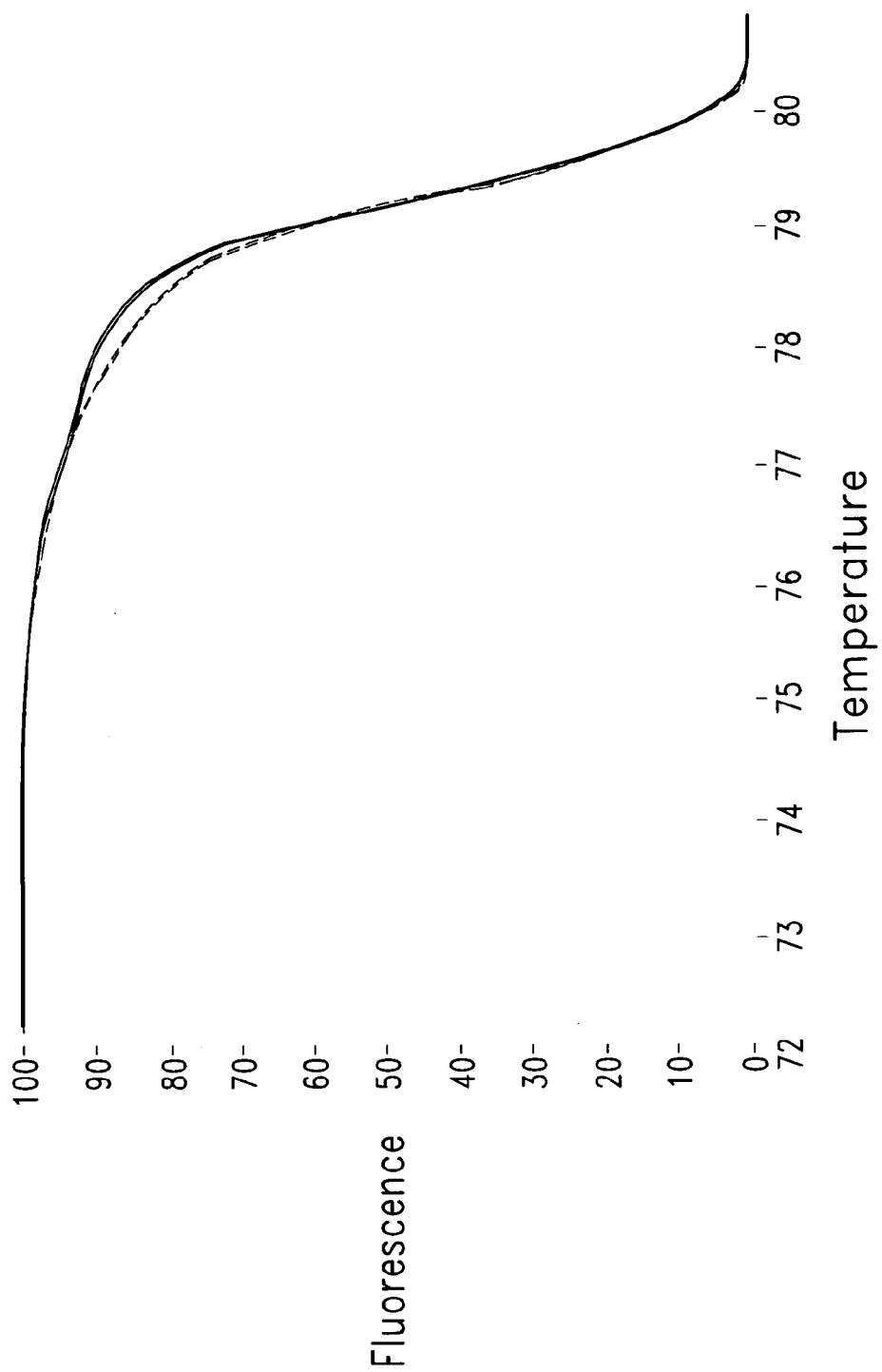
Figure 31:
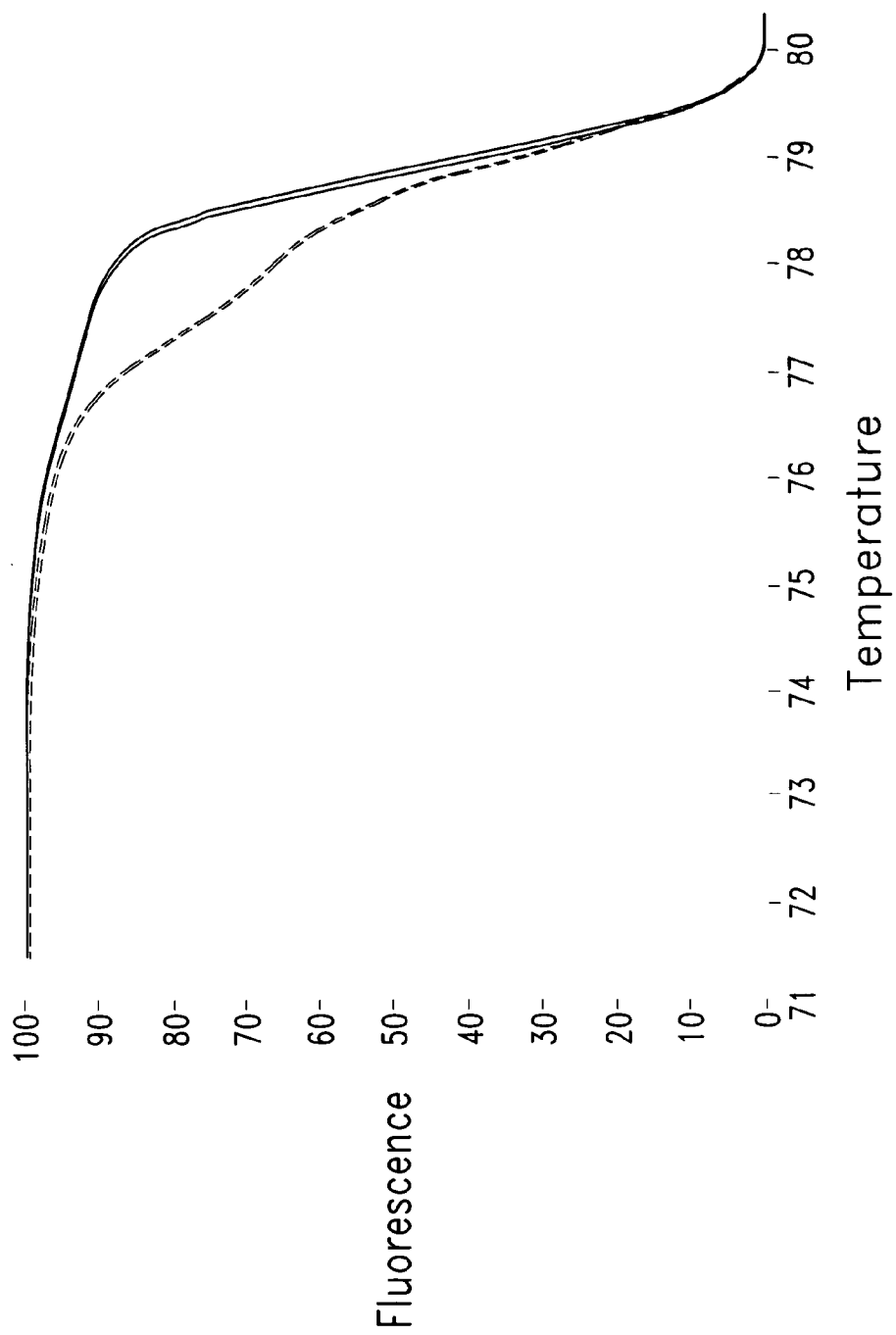
Figure 32:
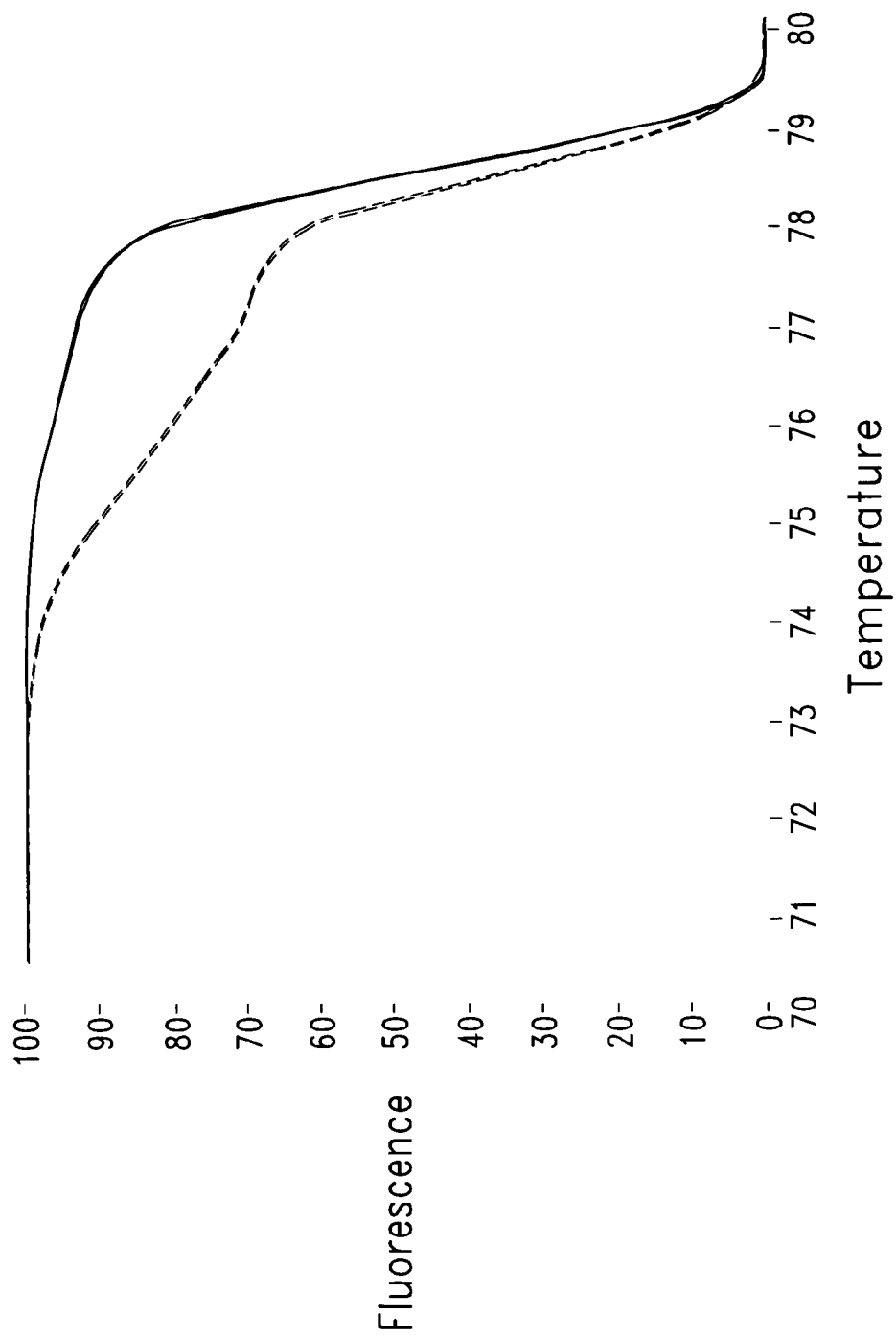

In another method, the curves in FIG. 27 were baseline subtracted and fit to a Gaussian (when possible) so that the area under the peaks can be calculated and plotted against cycle number as in FIG. 28B (closed triangle). In FIG. 28C this was further shown with samples of three different initial template concentrations, each fitted to a straight line indicating a positive and linear correlation between cycle number and specific amplification product as defined by the probe. Melting peak area values were negative during the few cycles prior to when they started to increase with cycle number. This provided the opportunity to set crossing points at zero peak area, although even if the peak area values did not cross zero, extrapolation to zero can be used. When these crossing points were plotted against the log of the initial template concentration, a linear relationship was found (FIG. 28D) indicating that it is possible to use melting of the unlabeled probe for quantification of the initial template by fluorescence monitoring during amplification.

While this and other examples use saturating dyes, it is understood that other dyes may be used with certain methods described herein, particularly with methods where detection of SNPs and other small changes is not necessary. For example, in the above method, the probe matched perfectly to the target sequence, and the method did not include detection of genetic variation. However, it is also understood that the above method can be used in combination with various other analyses, including genotyping.

EXAMPLE 21

Detection of Mutations in the c-kit Gene for the Diagnosis of GIST

The human c-kit protein is a transmembrane receptor tyrosine kinase which is activated through binding of its ligand. Activation of the tyrosine kinase leads to autophosphorylation of tyrosine residues which, in turn, leads to an intracellular signaling cascade resulting in cell proliferation. Mutations that cause activation of the c-kit protein independent of ligand binding have been observed in a variety of tumors including germ cell tumors, mast cell tumors and stromal tumors of the gastrointestinal tract (GISTs). These mutations are thought to be the driving force for neoplastic growth. One recent success in targeted molecular therapy is the development of the drug STI-571 (imatinib, gleevec) which inhibits the activated c-kit receptor in GISTs. This drug is a phenylaminopyrimidine derivative, and many GIST patients treated with STI-571 show partial responses and stabilization of disease. However, there is a need to provide an improved diagnosis for this class of neoplasm.

Historically, the diagnosis of stromal tumors in the gastrointestinal tract has been difficult. Currently, stromal tumors of the gastrointestinal tract are routinely immunostained for CD117 (c-kit). A positive immunostain suggests that the tumor is correctly identified as a GIST. However, sometimes the immunostain for c-kit is focal and/or equivocal and difficult to evaluate. Furthermore, the immunostain does not give information on the location, presence or absence, and type of an activating mutation, and commercially available CD-117 antibodies may cross-react with non c-kit molecules. High-resolution amplicon melting can be used as an improved method to rapidly screen for activating mutations in the c-kit gene. Sequence variants detected by high-resolution melting can optionally be further characterized by DNA sequencing.

An illustrative experiment for c-kit screening was performed as follows: A variety of GIST tissue specimens, including primary tumor, metastatic/recurrent tumor, neoplasms arising from the small and large intestine, stomach, peritoneum, and per-pancreatic soft tissue were obtained in paraffin blocks. DNA was isolated from sectioned paraffin-embedded tissue on glass slides by first de-paraffinizing and rehydrating the samples by successive washes in xylene, and then in 95%, 70%, 50% and 30% ethanol. After final rinsing in deionized $H_2O$, the slide was dried under an infra red lamp for 5 min. The appropriate area of tumor tissue was microdissected off the slide with a scalpel and incubated in 50 to 100 µl of 50 mM Tris-HCl (pH 8.0), 1 mM EDTA, 1% Tween 20, 1.0 mg/ml proteinase K overnight at 37° C. The sample was then incubated in a boiling $H_2O$ bath for 10 min to inactivate the proteinase K. After cooling on ice, the sample was diluted in 10 mM Tris-HCl (pH 7.5), 0.1 mM EDTA and subjected to polymerase chain reaction (PCR) with the exon-specific primers shown in Table 7.

TABLE 7

| Primer | Sequence (5'→3') | SEQ. ID. NO. |
|---|---|---|
| Exon 9 Forward | GATGCTCTGCTTCTGTACTG | SEQ ID NO.40 |
| Exon 9 Reverse | GCCTAAACATCCCCTTAAATTGG | SEQ ID NO.41 |
| Exon 11 Forward | CTCTCCAGAGTGCTCTAATGAC | SEQ ID NO.42 |
| Exon 11 Reverse | AGCCCCTGTTTCATACTGACC | SEQ ID NO.43 |
| Exon 13 Forward | CGGCCATGACTGTCGCTGTAA | SEQ ID NO.44 |
| Exon 13 Reverse | CTCCAATGGTGCAGGCTCCAA | SEQ ID NO.45 |
| Exon 17 Forward | TCTCCTCCAACCTAATAGTG | SEQ ID NO.46 |
| Exon 17 Reverse | GGACTGTCAAGCAGAGAAT | SEQ ID NO.47 |

PCR was performed in a total volume of 20 µl in a capillary cuvette. The reaction mixture contained 50 mM Tris-HCl (pH 8.5), 3 mM $MgCl_2$, 0.5 mg/ml BSA, 200 µM each of dATP, dGTP, and dCTP, 600 µM of dUTP, 0.5 µM primers, 1 µl of diluted Klentaq polymerase (1 µl of cold sensitive Klentaq polymerase incubated with 10 µl of enzyme diluent), 1 unit of uracil N-glycosylase (Amperase) and 20 µM dye D6. Polymerase chain reaction was performed on a LightCycler® (Roche Applied Systems, Indianapolis, Ind.) with an initial denaturation for 10 min at 95° C. (to denature the uracil glycosylase) followed by 45 cycles of 95° C. for 3 s, cooling at 20° C./s to 58° C. (exon 9 and 11), 62° C. (exon 13), or 55° C. (exon 17 for 10 s, followed by a heating 1° C./s to 75° C. for 0 s. Amplicon sizes were 235 bp (exon 9), 219 bp (exon 11), 227 bp (exon 13), 170 bp (exon 17). After PCR, the samples were momentarily heated to 95° C. and then cooled to 40° C. on the LightCycler®. The samples were then transferred to the high resolution DNA melting analysis instrument HR/1(Idaho Technology, Salt Lake City, Utah). Melting analysis was performed as described in Example 3. All samples were run in duplicate.

Illustrative results are shown in FIGS. 29-32 in which a heterozygous SNP (FIG. 29), a homozygous deletion of 12 bp juxtaposed to an SNP (FIG. 30), a heterozygous tandem duplication of 36 bp (FIG. 31), and a heterozygous deletion of 54 bp (FIG. 32) were detected by high-resolution amplicon melting analysis. Table 8, summarizes these and other mutations that were identified through high-resolution amplicon melting analysis and verified by DNA sequencing.

TABLE 8

| Sample number | Exon number with variance detected by high resolution melting | Base sequence changes established by DNA sequencing (het/hom) | Amino acid alteration |
|---|---|---|---|
| 1 | Exon 11 | missense SNP (het) | V559D |
| 2 | Exon 11 | *54 bp deletion (het) | DEL 557-574 |
| 5 | Exon 11 | 6 bp deletion (het) | DEL 558-559 |
| 6 | Exon 11 | *12 bp deletion +SNP (hom) | DEL 554-557; K558G |
| 7 | Exon 11 | *36 bp duplication (het) | DUP 574-585 |
| 8 | Exon 11 | *30 bp deletion +SNP (het) | DEL 548-557; K558Q |
| 9 | Exon 11 | *33 bp deletion +SNP (het) | DEL 547-557; K558Q |
| 13 | Exon 11 | *9 bp insertion (het) | INS 579-581 |
| 19 | Exon 11 | *6 bp deletion +SNP (het) | DEL 557-558; V559F |
| 20 | Exon 13 | missense SNP (het) | K642E |
| 26 | Exon 9 | 6 bp duplication (het) | DUP 502-503 |
| 25 | Exon 11 | *27 bp deletion +SNP (het) | DEL 565-573; T574P |
| 29 | Exon 11 | missense SNP (het) | W557R |
| Normal control | None | None | n/a |

*newly identified mutations
het: heterozygote
hom: homozygote

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All references cited herein are incorporated by reference as if fully set forth.

What is claimed is:

1. A PCR reaction mixture comprising
   a. a target nucleic acid,
   b. PCR reagents,
   c. a pair of oligonucleotide primers configured for amplifying a portion of the target nucleic acid to produce an amplicon, and
   d. a dsDNA binding dye having the formula:

wherein the moiety Y represents an optionally-substituted fused monocyclic or polycyclic aromatic ring or an optionally-substituted fused monocyclic or polycyclic nitrogen-containing heteroaromatic ring;

X is oxygen, sulfur, selenium, tellurium or a moiety selected from $C(CH_3)_2$ and $NR^1$, where $R^1$ is hydrogen or $C_{1-6}$alkyl;

$R^2$ is selected from the group consisting of $C_{1-6}$alkyl, $C_{3-8}$cycloalkyl, aryl, aryl($C_{1-3}$alkyl), hydroxyalkyl, alkoxyalkyl, aminoalkyl, mono and dialkylaminoalkyl, trialkylammoniumalkyl, alkylenecarboxylate, alkylenecarboxamide, alkylenesulfonate, optionally substituted cyclic heteroatom-containing moieties, and optionally substituted acyclic heteroatom-containing moieties;

t=0 or 1;

Z is a charge selected from 0 or 1;

$R^3$, $R^9$, and $R^{10}$ are each independently selected from the group consisting of hydrogen, $C_{1-6}$alkyl, and arylcarbonyl;

n=0,1, or 2; and

Q is an heterocycle selected from the group of structures consisting of:

wherein $R^5$, $R^6$, $R^7$, and $R^8$ are independently selected from the group consisting of hydrogen, halogen, alkyl, cycloalkyl, heteroalkyl, heterocycloalkyl, alkenyl, polyalkenyl, alkynyl, polyalkynyl, alkenylalkynyl, aryl, heteroaryl, alkoxy, alkylthio, arylthio, arylcarbonylthio, dialkylamino, cycloheteroalkylcarbonylthio, dialkylaminoalkylcarbonylthio, cycloalkylthio, cycloheteroalkylthio, trialkylanimoniumalkylthio, and nucleosidylthio, each of which may be optionally substituted; an acyclic heteroatom-containing moiety or a cyclic heteroatom-containing moiety, a BRIDGE-DYE, and a reactive group, each of which optionally includes a guaternary ammonium moiety, and $R^4$ is selected from the group consisting of arylcarbonylthio, cycloheteroalkylcarbonylthio, dialkylaminoalkylcarbonylthio, cycloalkylthio, cycloheteroalkylthio, trialkylammoniumalkylthio, and nucleosidylthio, each of which may be optionally substituted, wherein the dye is selected from the group consisting of F7, N7, O7, P7, Q7, R7, S7, T7, V7, W7, X7, T8, A9, C9, I9, J9, K9, L9, M9, N9, O9, P9 and R9 as presented in Table 2.

2. The PCR reaction mixture of claim 1, wherein the dsDNA binding dye has a percent saturation of at least 50%.

3. The PCR reaction mixture of claim 1, further comprising an unlabeled probe configured to hybridize to at least part of the amplicon.

4. The PCR reaction mixture of claim 1, further comprising a second pair of oligonucleotide primers configured for amplifying a second portion of the target nucleic acid to produce a second amplicon.

5. A kit for analyzing a target nucleic acid comprising:
an unlabeled probe, the unlabeled probe blocked at its 3'-end and configured to hybridize at least partially to the target nucleic acid, and
a dsDNA binding dye having a percent saturation of at least 50%, wherein the dye is selected from the group consisting of N7, R7, X7, T8, O7, P8, P7, Q7, T7, V7, W8, Z8, Z7, X8, G9, C9, A9, M9, N9, I9, J9, K9, L9, O9, and P9 as presented in Table 2.

6. The kit of claim 5, further comprising
a thermostable polymerase, and
oligonucleotide primers configured for amplifying the target nucleic acid.

7. The kit of claim 5, wherein the oligonucleotide primers comprise a first primer and a second primer, wherein the first primer is provided in a molar amount greater than the second primer.

8. A kit for analyzing a target nucleic acid comprising:
an unlabeled probe configured to hybridize at least partially to the target nucleic acid, and
a dsDNA binding dye selected from the group consisting of N7, R7, X7, T8, O7, P8, P7, Q7, T7, V7, W8, Z8, Z7, X8, G9, C9, A9, M9, N9, I9, J9, K9, L9, O9, and P9 as presented in Table 2.

9. A kit for analyzing a target nucleic acid sequence, the kit comprising:
i. a pair of primers configured for amplifying the target nucleic acid sequence, wherein the target nucleic acid sequence is a locus of a c-kit gene, wherein the pair of primers is CTCTCCAGAGTGCTCTAATGAC (SEQ ID NO. 42) and AGCCCCTGTTTCATACTGACC (SEQ ID NO. 43),
ii, a thermostable polymerase, and
iii, a dsDNA binding dye having a percent saturation of at least 50%.

* * * * *